(12) United States Patent
Franke et al.

(10) Patent No.: US 10,780,273 B2
(45) Date of Patent: Sep. 22, 2020

(54) STIMULATION DEVICES AND METHODS FOR TREATING DRY EYE

(71) Applicant: Oculeve, Inc., South San Francisco, CA (US)

(72) Inventors: Manfred Franke, Valencia, CA (US); James Donald Loudin, Alhambra, CA (US); John Wardle, San Clemente, CA (US); Mark Jeffrey Holdbrook, Sunnyvale, CA (US)

(73) Assignee: OCULEVE, INC., South San Francisco, CA (US)

( * ) Notice: Subject to any disclaimer, the term of this patent is extended or adjusted under 35 U.S.C. 154(b) by 44 days.

(21) Appl. No.: 16/137,464

(22) Filed: Sep. 20, 2018

(65) Prior Publication Data

US 2019/0022392 A1 Jan. 24, 2019

Related U.S. Application Data

(60) Continuation of application No. 15/676,910, filed on Aug. 14, 2017, now Pat. No. 10,112,048, which is a
(Continued)

(51) Int. Cl.
*A61N 1/36* (2006.01)
*A61N 1/375* (2006.01)
(Continued)

(52) U.S. Cl.
CPC ....... *A61N 1/36046* (2013.01); *A61N 1/0546* (2013.01); *A61N 1/3606* (2013.01);
(Continued)

(58) Field of Classification Search
None
See application file for complete search history.

(56) References Cited

U.S. PATENT DOCUMENTS 2,512,882 A 6/1950 Truesdale
2,525,381 A 10/1950 Tower
(Continued)

FOREIGN PATENT DOCUMENTS

CN 1488331 A 4/2004
CN 2693275 Y 4/2005
(Continued)

OTHER PUBLICATIONS

Ahmed, E. M. et al. (2013, e-published Jul. 18, 2013). "Hydrogel: Preparation, characterization, and applications: A review," Cairo University, Journal of Advanced Research (2015) 6, 105-121.
(Continued)

*Primary Examiner* — Brian T Gedeon
(74) *Attorney, Agent, or Firm* — Mintz Levin Cohn Ferris Glovsky and Popeo, P.C.

(57) ABSTRACT

Described herein are devices and methods of use thereof for treating dry eye, tired eye, or other forms of ocular discomfort such as from contact lenses. The methods generally include applying spatially and/or temporally patterned stimulation to one or more anatomical structures located in an ocular or nasal region. The electrical stimulation may elicit a reflex that activates the lacrimal gland or may directly activate the lacrimal gland or nerves innervating the lacrimal gland to produce tears. The devices may be implantable or handheld, and may be configured to deliver the spatially and/or temporally patterned stimulation patterns described.

19 Claims, 38 Drawing Sheets

Related U.S. Application Data division of application No. 14/920,860, filed on Oct. 22, 2015, now Pat. No. 9,737,712.

(60) Provisional application No. 62/067,416, filed on Oct. 22, 2014.

(51) Int. Cl.
*A61N 1/372* (2006.01)
*A61N 1/05* (2006.01)

(52) U.S. Cl.
CPC ....... *A61N 1/3758* (2013.01); *A61N 1/37205* (2013.01); *A61N 1/37247* (2013.01); *A61N 1/0526* (2013.01); *A61N 1/36146* (2013.01); *A61N 1/3756* (2013.01)

(56) References Cited

U.S. PATENT DOCUMENTS

| | | |
|---|---|---|
| 3,620,219 A | 11/1971 | Barker |
| 3,709,228 A | 1/1973 | Barker |
| 3,885,550 A | 5/1975 | MacLeod |
| D257,495 S | 11/1980 | Bros et al. |
| 4,495,676 A | 1/1985 | Hartmetz, II |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,352,445 A | 10/1994 | Lavaux |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,611,970 A | 3/1997 | Apollonio et al. |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry, Jr. et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,935,155 A | 8/1999 | Humayun et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,200,626 B1 | 3/2001 | Grobe, III et al. |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,389 B1 | 3/2008 | Newsome |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |

(56) References Cited

U.S. PATENT DOCUMENTS

| | | |
|---|---|---|
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,032 B1 | 2/2011 | Garito et al. |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,083,787 B2 | 12/2011 | Korb et al. |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,521,292 B2 | 8/2013 | Wei et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,717,627 B2 | 8/2017 | Kuzma et al. |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,821,159 B2 | 11/2017 | Ackermann et al. |
| 9,956,397 B2 | 5/2018 | Loudin et al. |
| D826,420 S | 8/2018 | Ackermann et al. |
| 10,143,846 B2 | 12/2018 | Ackermann et al. |
| D837,396 S | 1/2019 | Ackermann et al. |
| 10,207,108 B2 | 2/2019 | Franke et al. |
| 2001/0018918 A1 | 9/2001 | Burnside et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt |
| 2002/0188331 A1 | 12/2002 | Fang et al. |
| 2003/0014089 A1 | 1/2003 | Chow et al. |
| 2003/0045909 A1 | 3/2003 | Gross et al. |
| 2003/0045911 A1 | 3/2003 | Bruchmann et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0133877 A1 | 7/2003 | Levin |
| 2003/0139784 A1 | 7/2003 | Morimoto et al. |
| 2003/0176892 A1 | 9/2003 | Shalev |
| 2003/0176898 A1 | 9/2003 | Gross et al. |
| 2003/0192784 A1 | 10/2003 | Zhou |
| 2003/0229381 A1 | 12/2003 | Hochmair et al. |
| 2003/0233134 A1 | 12/2003 | Greenberg et al. |
| 2003/0233135 A1 | 12/2003 | Yee |
| 2004/0050392 A1 | 3/2004 | Tu et al. |
| 2004/0059466 A1 | 3/2004 | Block et al. |
| 2004/0092992 A1 | 5/2004 | Adams et al. |
| 2004/0098036 A1 | 5/2004 | Bergersen |
| 2004/0098067 A1 | 5/2004 | Ohta et al. |
| 2004/0127942 A1 | 7/2004 | Yomtov et al. |
| 2004/0138646 A1 | 7/2004 | Walla |
| 2004/0147973 A1 | 7/2004 | Hauser |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0004625 A1 | 1/2005 | Chow |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev |
| 2005/0197675 A1 | 9/2005 | David et al. |
| 2005/0251061 A1 | 11/2005 | Schuler et al. |
| 2005/0256570 A1 | 11/2005 | Azar |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0036296 A1 | 2/2006 | Greenberg et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0206162 A1 | 9/2006 | Wahlstrand et al. |
| 2006/0216317 A1 | 9/2006 | Reinhard et al. |
| 2006/0235430 A1 | 10/2006 | Le et al. |
| 2006/0239482 A1 | 10/2006 | Hatoum |
| 2006/0259098 A1 | 11/2006 | Erickson |
| 2006/0271024 A1 | 11/2006 | Gertner et al. |
| 2006/0271108 A1 | 11/2006 | Libbus et al. |
| 2006/0276738 A1 | 12/2006 | Becker |
| 2007/0031341 A1 | 2/2007 | DiMauro et al. |
| 2007/0038250 A1 | 2/2007 | He et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0255333 A1 | 11/2007 | Giftakis et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299420 A1 | 12/2007 | Peyman |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109046 A1 | 5/2008 | Lima et al. |
| 2008/0109054 A1 | 5/2008 | Hastings et al. |
| 2008/0114424 A1 | 5/2008 | Grenon et al. |
| 2008/0132933 A1 | 6/2008 | Gerber |
| 2008/0132969 A1 | 6/2008 | Bennett et al. |
| 2008/0140141 A1 | 6/2008 | Ben-David et al. |
| 2008/0183242 A1 | 7/2008 | Tano et al. |
| 2008/0183243 A1 | 7/2008 | Shodo |
| 2008/0208287 A1 | 8/2008 | Palermo et al. |
| 2008/0208335 A1 | 8/2008 | Blum et al. |

(56) References Cited

U.S. PATENT DOCUMENTS

| | | |
|---|---|---|
| 2008/0221642 A1 | 9/2008 | Humayun et al. |
| 2008/0269648 A1 | 10/2008 | Bock |
| 2008/0288036 A1 | 11/2008 | Greenberg et al. |
| 2008/0294066 A1 | 11/2008 | Hetling et al. |
| 2009/0005835 A1 | 1/2009 | Greenberg et al. |
| 2009/0012573 A1 | 1/2009 | Karell |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0239235 A1 | 9/2009 | DeMaria et al. |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2009/0312818 A1 | 12/2009 | Horsager et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0100165 A1 | 4/2010 | Swanson et al. |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0256609 A1 | 10/2010 | Hillis et al. |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0311688 A1 | 12/2010 | Chapin et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0076775 A1 | 3/2011 | Stewart et al. |
| 2011/0077551 A1 | 3/2011 | Videbaek |
| 2011/0077698 A1 | 3/2011 | Tsampazis et al. |
| 2011/0081333 A1 | 4/2011 | Shantha et al. |
| 2011/0082518 A1 | 4/2011 | Filippello |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0184490 A1 | 7/2011 | Horsager et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0270067 A1 | 11/2011 | Faraji et al. |
| 2011/0270348 A1 | 11/2011 | Goetz |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1 | 12/2011 | De Vos |
| 2011/0313488 A1 | 12/2011 | Hincapie Ordonez et al. |
| 2012/0053648 A1 | 3/2012 | Neher et al. |
| 2012/0112903 A1 | 5/2012 | Kaib et al. |
| 2012/0130398 A1 | 5/2012 | Ackermann et al. |
| 2012/0133887 A1 | 5/2012 | Huang |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson |
| 2012/0298105 A1 | 11/2012 | Osorio |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0072755 A1 | 3/2013 | Papania et al. |
| 2013/0085551 A1* | 4/2013 | Bachinski .......... A61N 1/36014 607/59 |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0197321 A1 | 8/2013 | Wilson |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1 | 10/2013 | Otto et al. |
| 2013/0274831 A1 | 10/2013 | Otto et al. |
| 2013/0304154 A1 | 11/2013 | Goodman et al. |
| 2013/0310887 A1 | 11/2013 | Curtis |
| 2013/0336557 A1 | 12/2013 | Cruzat et al. |
| 2014/0012182 A1 | 1/2014 | Shantha |
| 2014/0056815 A1 | 2/2014 | Peyman |
| 2014/0081353 A1 | 3/2014 | Cook et al. |
| 2014/0088463 A1* | 3/2014 | Wolf .................. A61B 18/1477 601/2 |
| 2014/0148872 A1 | 5/2014 | Goldwasser et al. |
| 2014/0156000 A1 | 6/2014 | Campin et al. |
| 2014/0163580 A1 | 6/2014 | Tischendorf et al. |
| 2014/0214115 A1 | 7/2014 | Greiner et al. |
| 2014/0214118 A1 | 7/2014 | Greiner et al. |
| 2014/0214120 A1 | 7/2014 | Simon et al. |
| 2014/0214124 A1 | 7/2014 | Greiner et al. |
| 2014/0214125 A1 | 7/2014 | Greiner et al. |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0324147 A1 | 10/2014 | Wagner |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0182145 A1 | 7/2015 | Gazdzinski |
| 2015/0238754 A1 | 8/2015 | Loudin et al. |
| 2015/0335900 A1 | 11/2015 | Ackermann et al. |
| 2015/0343202 A1 | 12/2015 | Picaud et al. |
| 2015/0362755 A1 | 12/2015 | Lee et al. |
| 2016/0022992 A1 | 1/2016 | Franke et al. |
| 2016/0058615 A1 | 3/2016 | Camras et al. |
| 2016/0080720 A1 | 3/2016 | Fullam |
| 2016/0114163 A1 | 4/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1 | 12/2016 | Kahook |

(56) References Cited

U.S. PATENT DOCUMENTS

| | | |
|---|---|---|
| 2017/0049619 A1 | 2/2017 | Kahook |
| 2017/0157401 A1 | 6/2017 | Loudin et al. |
| 2017/0188947 A1 | 7/2017 | Connor |
| 2017/0239459 A1 | 8/2017 | Loudin et al. |
| 2017/0252563 A1 | 9/2017 | Franke et al. |
| 2017/0312521 A1 | 11/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368333 A1 | 12/2017 | Loudin et al. |
| 2017/0368359 A1 | 12/2017 | Loudin et al. |
| 2018/0064940 A1 | 3/2018 | Ackermann et al. |
| 2018/0064941 A1 | 3/2018 | Ackermann et al. |
| 2018/0064942 A1 | 3/2018 | Franke et al. |
| 2018/0153394 A1 | 6/2018 | Franke et al. |
| 2018/0154137 A1 | 6/2018 | Ackermann et al. |
| 2018/0154161 A1 | 6/2018 | Ackermann et al. |
| 2018/0161579 A1 | 6/2018 | Franke et al. |
| 2018/0280688 A1 | 10/2018 | Loudin et al. |
| 2019/0022392 A1 | 1/2019 | Franke et al. |
| 2019/0167978 A1 | 6/2019 | Ackermann et al. |
| 2019/0217095 A1 | 7/2019 | Franke et al. |
| 2019/0282804 A1 | 9/2019 | Ackermann et al. |
| 2019/0290922 A1 | 9/2019 | Ackermann et al. |
| 2019/0308009 A1 | 10/2019 | Loudin et al. |
| 2019/0344077 A1 | 11/2019 | Ackermann et al. |
| 2020/0030615 A1 | 1/2020 | Loudin et al. |
| 2020/0038238 A1 | 2/2020 | Kuzma et al. |

FOREIGN PATENT DOCUMENTS

| | | |
|---|---|---|
| CN | 101087822 A | 12/2007 |
| CN | 101503491 A | 8/2009 |
| CN | 101589085 A | 11/2009 |
| CN | 101616663 A | 12/2009 |
| CN | 101829120 A | 9/2010 |
| CN | 101939043 A | 1/2011 |
| CN | 102266592 A | 12/2011 |
| CN | 103467652 A | 12/2013 |
| DE | 102006048819 A1 | 4/2008 |
| EM | 2102681 0001 | 10/2012 |
| EM | 2199000 0001 | 3/2013 |
| EP | 0109935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| EP | 3263175 A1 | 1/2018 |
| GB | 2 129 690 B | 3/1987 |
| GB | 2 456 002 A | 7/2009 |
| JP | S60500241 A | 2/1985 |
| JP | 2002-519138 A | 7/2002 |
| JP | 2002-325851 A | 11/2002 |
| JP | 2002-539859 A | 11/2002 |
| JP | 2004-508847 A | 3/2004 |
| JP | 2004-526510 A | 9/2004 |
| JP | 2005-502409 A | 1/2005 |
| JP | 2005-052461 A | 3/2005 |
| JP | 2005-144178 A | 6/2005 |
| JP | 2005-521489 A | 7/2005 |
| JP | 2005-528169 A | 9/2005 |
| JP | 2006-515900 A | 6/2006 |
| JP | 2006-311917 A | 11/2006 |
| JP | 2007 044323 A | 2/2007 |
| JP | 2007 528751 A | 10/2007 |
| JP | 2008-55000 A | 3/2008 |
| JP | 2008 183248 A | 8/2008 |
| JP | 2008 541850 A | 11/2008 |
| JP | 2009-523503 A | 6/2009 |
| JP | 2010 505563 A | 2/2010 |
| JP | 2010 051562 A | 3/2010 |
| JP | 2010506654 A | 3/2010 |
| JP | 2010 537777 A | 12/2010 |
| JP | 2011-030734 A | 2/2011 |
| JP | 2011-524780 A | 9/2011 |
| JP | 2012-100708 A | 5/2012 |
| JP | 2012-115545 A | 6/2012 |
| JP | 2012-200558 A | 10/2012 |
| JP | 2013-528416 A | 7/2013 |
| RU | 2338492 C1 | 11/2008 |
| WO | WO-00/01320 A2 | 1/2000 |
| WO | WO-00/56393 A1 | 9/2000 |
| WO | WO-00/62672 A1 | 10/2000 |
| WO | WO-01/05388 A2 | 1/2001 |
| WO | WO-01/85094 A2 | 11/2001 |
| WO | WO-02/078592 A2 | 10/2002 |
| WO | WO-03/023907 A1 | 3/2003 |
| WO | WO-03/082080 A2 | 10/2003 |
| WO | WO-03/087433 A1 | 10/2003 |
| WO | WO-03/101535 A1 | 12/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/028003 A2 | 3/2007 |
| WO | WO-2007/079543 A1 | 7/2007 |
| WO | WO-2008/048321 A1 | 4/2008 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/069317 A1 | 6/2010 |
| WO | WO-2010/076904 A1 | 7/2010 |
| WO | WO-2010/099818 A1 | 9/2010 |
| WO | WO-2010/123704 A2 | 10/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2012/174161 A1 | 12/2012 |
| WO | WO-2013/157320 A1 | 10/2013 |
| WO | WO-2013/162793 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/153218 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |
| WO | WO-2017/192572 A1 | 11/2017 |
| WO | WO-2013/055940 A2 | 4/2018 |
| WO | WO-2013/055940 A3 | 4/2018 |

OTHER PUBLICATIONS

"Vapor Pressure Data" for H2O (2012). Handbook of Chemistry and Physics, 73rd edition, 1 total page.

(56) References Cited

OTHER PUBLICATIONS

Acar, M. et al. (2013). "Ocular surface assessment in patients with obstructive sleep apnea-hypopnea syndrome," Sleep Breath 17(2):583-588. Published online: Jun. 5, 2012.
Amparo (2013). "Topical Interleukin 1 Receptor Antagonist for Treatment of Dry Eye Disease," JAMA Ophth. 131(6):715-723.
Anonymous (2007). "The epidemiology of dry eye disease: report of the Epidemiology Subcommittee of the International Dry Eye WorkShop (2007)," Ocul. Surf. 5(2):93-107.
Bajpai et al. (2012). "Preparation, Characterization and Water Uptake Behavior of Polysaccharide Based Nanoparticles," Prog. Nanotech. Nanomat. 1(1):9-17.
Baraniuk et al. (2007). "Nasonasal Reflexes, the Nasal Cycle, and Sneeze," Curr. Allergy and Asthma Reports 7:105-111.
Baroody et al. (Mar. 2008) "Nasal Ocular Reflexes and Eye Symptoms in Patients with Allergic Rhinitis", Annals of Allergy, Asthma & Immunology, 100:194-199.
Baroody et al. (Jun. 2009) "Fiuticasone Furoate Nasal Spray Reduces the Nasal-Ocular Reflex: a Mechanism for the Efficacy of Topical Steroids in Controlling Allergic Eye Symptoms", Journal of Allergy and Clinical Immunology, 123:1342-1348.
Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Calonge (2001). "The Treatment of Dry Eye," Survey Ophth. 45(2):S227-S239.
Cipriano et al. (2014). "Superabsorbent Hydrogels That Are Robust and Highly Stretchable," Am. Chem Soc. 47(13):4445-4452.
Dart et al. (2002). "Effects of 25% Propylene Glycol Hydrogel (Solugel) on Second Intention Wound Healing in Horses," Vet. Surg. 31(4):309-313.
Drummond (1995) "Lacrimation and Cutaneous Vasodilatation in the Face Induced by Painful Stimulation of the Nasal Ala and Upper Lip", Journal of the Autonomic Nervous System, 51:109-116.
Elsby et al. (1967). "Lacrimal Secretion in the Cat," Br. J. Pharm. Chemother. 29(1):1-7.
Eye Health (2014). "Watery eyes in cold weather," Oregon Eye Specialists, PC, located at http://www.oregoneyes.net/watery-eyes-in-cold-weather/, 3 total pages.
Friedman et al. (2016). "A nonrandomized, open-label study to evaluate the effect of nasal stimulation on tear production in subjects with dry eye disease," Clin. Ophthal. 10:795-804.
Friedman, N. J. (2010) "Impact of Dry Eye Disease and Impact on Quality of Life." Current Opinion in Ophthalmology. 21:310-316.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Galor, A. et al. (2014). "Environmental factors affect the risk of dry eye syndrome in a United States veteran population," Opth. 121:972-973.
Gupta et al. (1997) "Nasolacrimal Stimulation of Aqueous Tear Production", Cornea, 16(6):645-648.
Harvard Health Publishing (Nov. 2010) "Dry Eyes and What You Can Try", Harvard Medical School, 2 pages.
Heigle, et al., (1996) "Aqueous Tear Production in Patients with Neurotrophic Keratitis", Cornea, 15(2):135-138.
Holzer (1991) "Capsaicin: Cellular Targets, Mechanisms of Action, and Selectivity for Thin Sensory Neurons", Pharamalogical Reviews, 43(2):143-201.

Ikemura et al. (2008). "UV-VIS Spectra and Photoinitiation Behaviors of Acylphosphine Oxide and Bisacylphosphine Oxide Derivatives in unfilled, Light-Cured Dental Resins," Dent. Mat. J. 27:765-774.
Krupin et al. (Jan. 1977) "Decreased Basal Tear Production Associated with General Anesthesia", Archives of Ophthalmology, 95:107-108.
Lora et al. (2009). "Lacrimal Nerve Stimulation by a Neurostimulator for Tear Production," Invest. Ophth. Vis. Science 50(13):172.
Loth et al. (1994) "Effect of Nasal Anaesthesia on Lacrimal Function After Nasal Allergen Challenge", Clinical & Experimental Allergy, 24:375-376.
Mallepally et al. (2013). "Superabsorbent Alginate Aerogels," J. Supercritical Fluids 79:1-5.
McDonald et al. (2009) "Hydroxypropyl Cellulose Ophthalmic Inserts (Lacrisert) Reduce the Signs and Symptoms of Dry Eye Syndrome and Improve Patient Quality of Life", Transactions of the American Ophthalmological Society, 107:214-222.
Meng, I.D. et al. (2013). "The role of corneal afferent neurons in regulating tears under normal and dry eye conditions," Exp. Eye Res. 117:79-87.
Pasqui et al. (2012). "Polysaccharide-Based Hydrogels: The Key Role of Water in Affecting Mechanical Properties," Polymers 4(3):1517-1534.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
Philip et al. (Dec. 1994) "The Human Nasal Response to Capsaicin", Journal of Allergy and Clinical Immunology, 94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111(1):106-108.
Van Setten, G. et al. (2016). "Evidence of seasonality and effects of psychrometry in dry eye disease," Acta Opth. 94:499-506.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Yu, et al. (Apr. 2011) "The Economic Burden of Dry Eye Disease in the United States: a Decision Tree Analysis", Cornea, 30(4):379-387.
Zilstorff-Pedersen (1965). "Quantitative Measurements of the Nasolacrimal Reflex," Arch. Oto. 81:457-462.
Olsen et al. (1998) "Human Sclera: Thickness and Surface Area." American Journal of Ophthalmology. Feb. 1998, vol. 125, Issue 2, pp. 237-241.

* cited by examiner

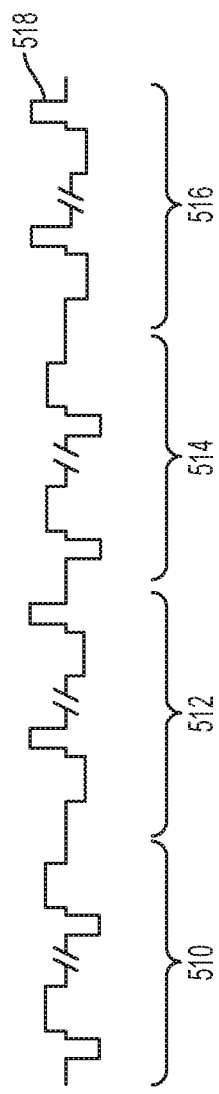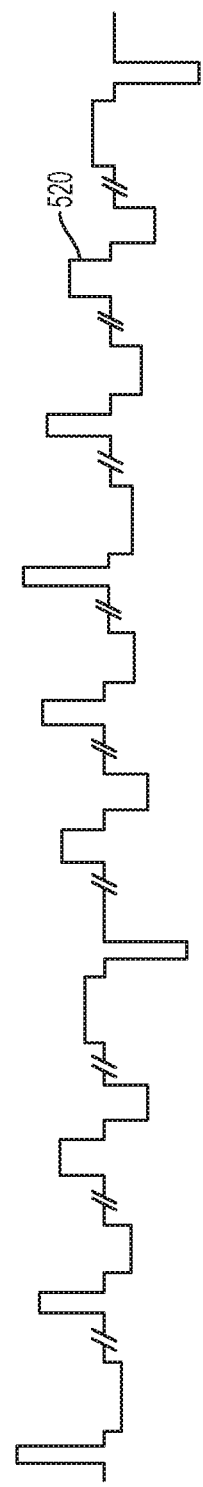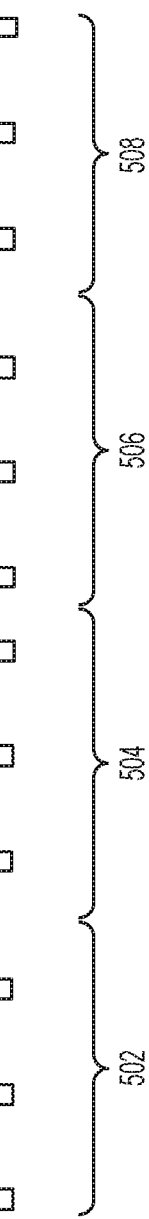

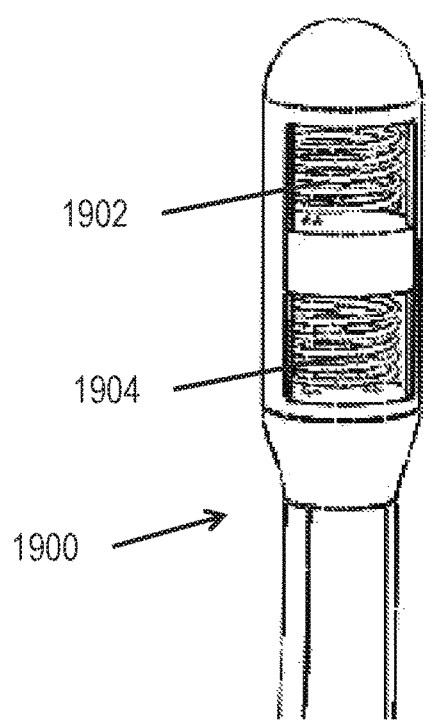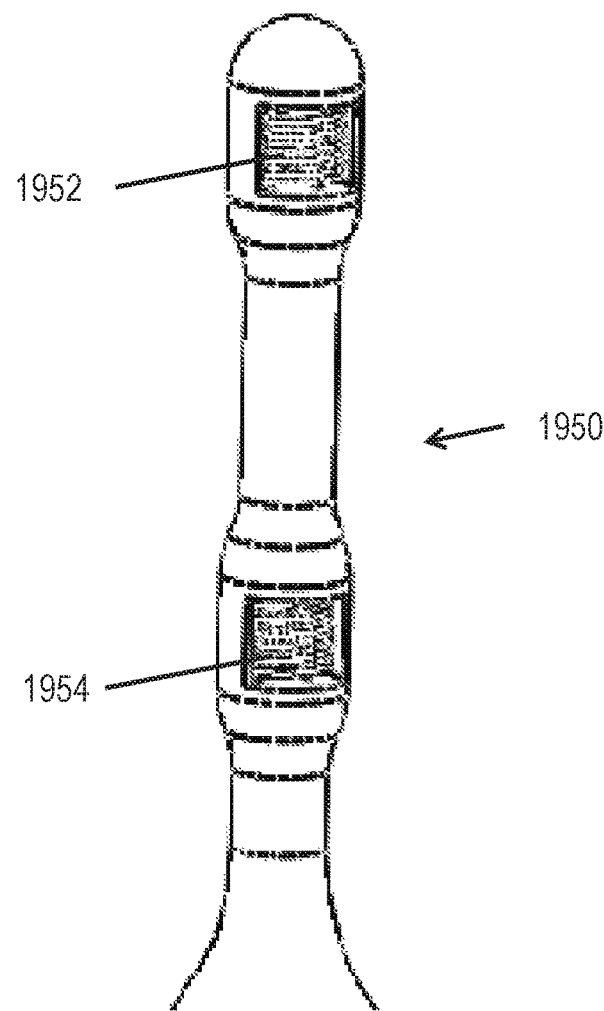
FIG. 19A
FIG. 19B

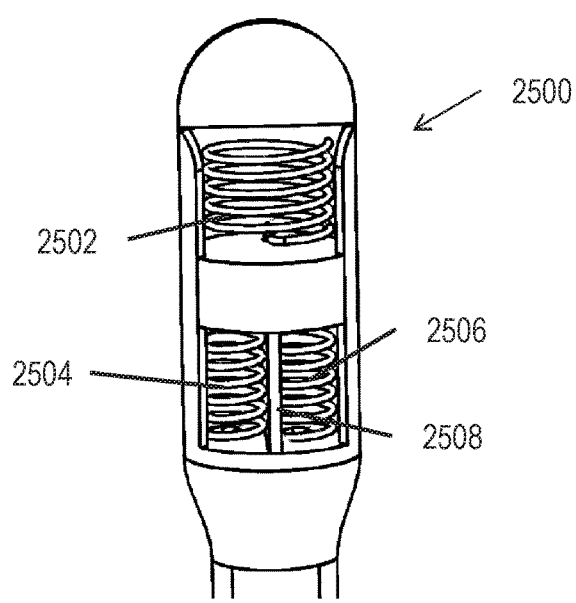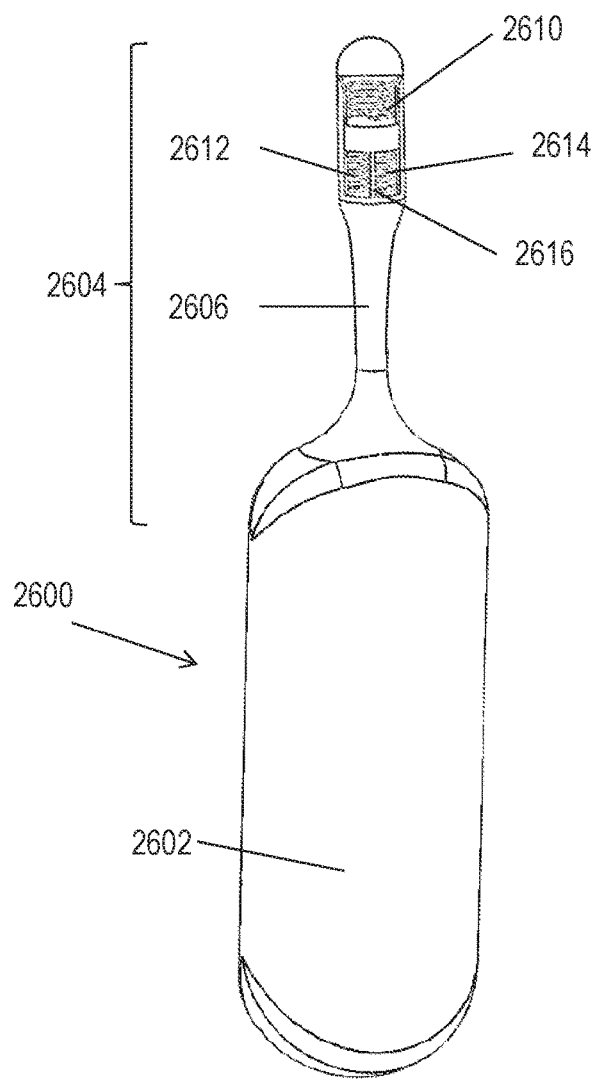
FIG. 25
FIG. 26

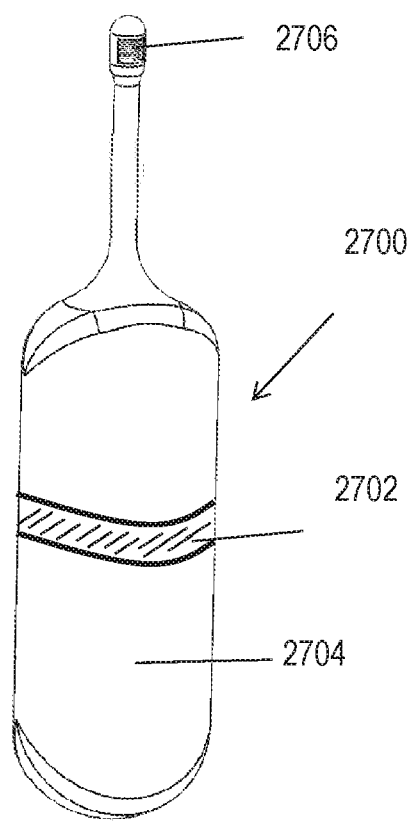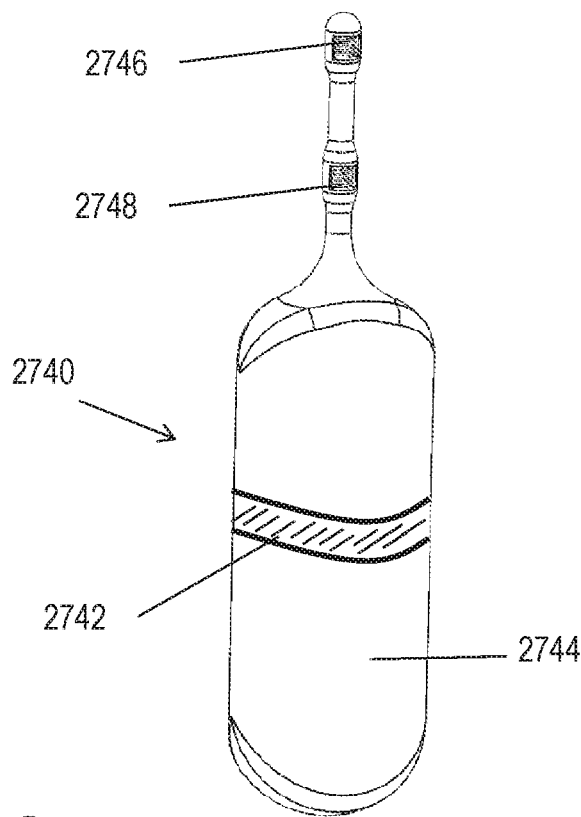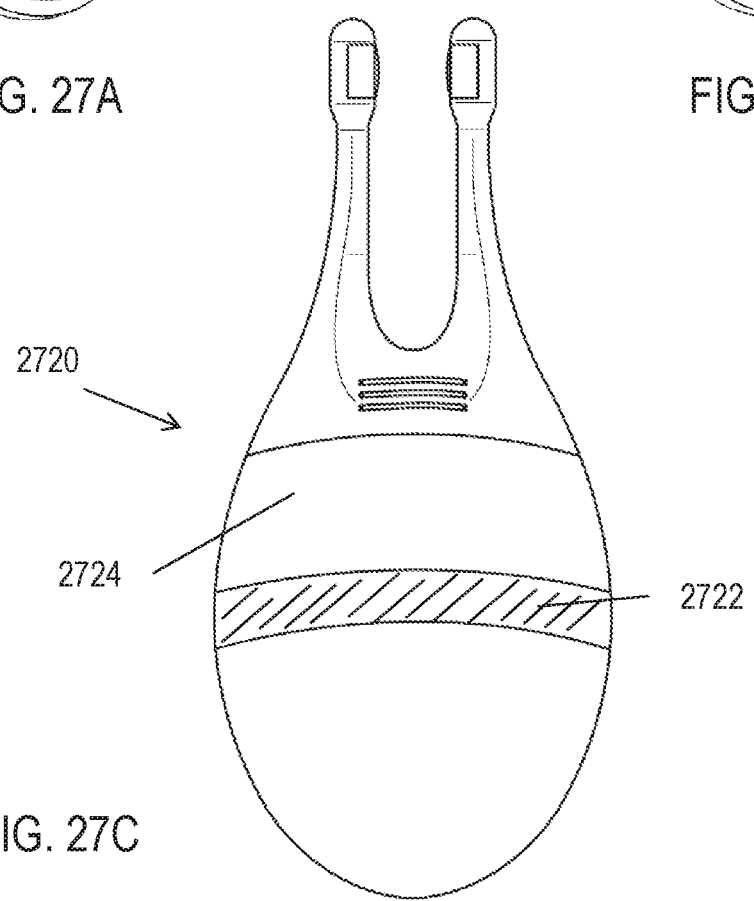
FIG. 27A
FIG. 27B
FIG. 27C

STIMULATION DEVICES AND METHODS FOR TREATING DRY EYE

CROSS-REFERENCE TO RELATED APPLICATIONS

This application is a continuation application of U.S. patent application Ser. No. 15/676,910, filed Aug. 14, 2017, which is a divisional of U.S. patent application Ser. No. 14/920,860 filed Oct. 22, 2015, which issued as U.S. Pat. No. 9,737,712 on Aug. 22, 2017, which claims priority to U.S. Provisional Patent Application No. 62/067,416, filed on Oct. 22, 2014, and titled "STIMULATION PATTERNS," each of which is hereby incorporated by reference herein in its entirety.

FIELD

Described herein are devices and methods of use thereof for treating dry eye or tiredness of the eye. The methods generally include applying spatially and/or temporally patterned stimulation to one or more anatomical structures located in an ocular or nasal region. The electrical stimulation may elicit a reflex that activates the lacrimal gland or may directly activate the lacrimal gland or nerves innervating the lacrimal gland to produce tears.

BACKGROUND

Dry Eye Disease ("DED") is a condition that affects millions of people worldwide. More than 40 million people in North America have some form of dry eye, and many millions more suffer worldwide. DED results from the disruption of the natural tear film on the surface of the eye, and can result in ocular discomfort, visual disturbance, and a reduction in vision-related quality of life. Activities of daily living such as driving, computer use, housework, and reading have also been shown to be negatively impacted by DED. Patients with severe cases of DED are at risk for serious ocular health deficiencies such as corneal ulceration and can experience a quality of life deficiency comparable to that of moderate-severe angina.

DED is progressive in nature, and generally results from insufficient tear coverage on the surface of the eye. This poor tear coverage prevents healthy gas exchange and nutrient transport for the ocular surface, promotes cellular desiccation, and creates a poor refractive surface for vision. Poor tear coverage typically results from: 1) insufficient aqueous tear production from the lacrimal glands (e.g., secondary to post-menopausal hormonal deficiency, autoimmune disease, LASIK surgery, etc.), and/or 2) excessive evaporation of aqueous tear resulting from dysfunction of the meibomian glands. In turn, low tear volume causes a hyperosmolar environment that induces inflammation of the ocular surface. This inflammatory response induces apoptosis of surface cells, which in turn prevents proper distribution of the tear film on the ocular surface so that any given tear volume is rendered less effective. A vicious cycle is initiated where more inflammation can ensue and cause further surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

There is a wide spectrum of treatments for DED, however, these treatments do not provide adequate treatment of the condition. Treatment options include: artificial tear substitutes, ointments, gels, warm compresses, environmental modification, topical cyclosporine, omega-3 fatty acid supplements, punctal plugs, and moisture chamber goggles. Patients with severe disease may further be treated with punctal cautery, systemic cholinergic agonists, systemic anti-inflammatory agents, mucolytic agents, autologous serum tears, PROSE scleral contact lenses, and tarsorrhaphy. Despite these treatment options, DED continues to be considered one of the most poorly treated diseases in ophthalmology. Accordingly, it would be desirable to have a more effective treatment for dry eye.

SUMMARY

Described here are methods for treating one or more conditions (such as dry eye, tired eyes, reducing discomfort from wearing contact lenses, etc.) by providing electrical stimulation to an anatomical structure located in an ocular region or a nasal region. Exemplary anatomical structures include nerves, muscles, mucosal tissues, cutaneous sensory structures such as Parcian corpuscles, Merkel cells, etc., within these regions. The electrical stimulation, when delivered to certain targets as described herein, is generally capable of initiating a reflex circuit that activates the lacrimal gland to produce tears. The reflex circuit may include stimulation of a nerve directly or a cutaneous sensory cell that in turn activates a nerve which then produces either sensory input to the brain, or motor input to a nerve that activates a muscle near, e.g., the eye, which in turn provides sensory input to the brain and initiation of the reflex to activate the lacrimal gland. The electrical stimulation may additionally or alternatively be capable, when delivered to other certain targets as described herein, of directly driving efferent fibers innervating the lacrimal gland to produce tears.

More specifically, methods of generating lacrimation (tear production) by spatially controlling the delivery of electrical stimuli and/or by modifying parameters of electrical waveforms to generate afferent or efferent input are described. These methods generally direct current flow through particular pathways and/or modify the current pathways over time. The methods may also optimize waveforms for a sensed paresthesia, e.g., a sensation of tickle, twitch, and/or vibration in the eyelid and/or vicinity of the eyelid, eyebrow, as well as the temporal and frontal area of the head. Experimentation by the inventors has found that these sensations are strongly associated with lacrimation.

Using the stimuli disclosed herein, it is believed that sensory nerves are activated to send input to the brain to produce lacrimation. Additionally or alternatively, the stimuli may activate motor nerves that cause muscles in the vicinity of the orbit, the nose, the mouth, and/or the frontal or temporal face to vibrate in order to generate the sensation of tingle or twitch or vibration as the effect, which initiates the reflex pathway and thereby leads to lacrimation.

Implantable or hand-held devices may be employed when applying the electrical stimulation. In some handheld variations, the devices may comprise a stimulator body and a stimulator probe. The stimulator probe may be releasably connected to the stimulator body, and in some instances, the stimulator body is reusable and the stimulator probe is disposable. In some variations, the device further comprises a user interface. The user interface may comprise one or more operating mechanisms to adjust one or more parameters of the stimulus. Additionally or alternatively, the user interface may comprise one or more feedback elements.

In handheld variations comprising a stimulator probe, the stimulator probe may comprise one or more nasal insertion prongs, and the stimulator body may comprise a control subsystem to control a stimulus to be delivered to the patient via the stimulator probe. In some of these variations, the stimulator probe comprises a single nasal insertion prong, while in other variations the stimulator probe comprises at least two nasal insertion prongs. The stimulator probe may comprise at least one electrode, and may comprise a plurality of electrodes. The electrode may comprise a hydrogel, or in other variations, the electrode comprises one or more of platinum, platinum-iridium, gold, or stainless steel. Some variations of device may comprise return contacts not located on a nasal insertion prong, such as return contacts on the stimulator body or the stimulator probe.

The electrical stimulation applied to the anatomical structures generally includes a plurality of waveform parameters that define a waveform. Delivery of the electrical stimulus may help to treat DED by inducing an increase in lacrimation, or modifying the components of lacrimated tears, and may generate a paresthesia sensed by a patient. These waveforms may be capable of increasing tear output as well as patient comfort during and/or after application of the stimulation. In some variations, the stimulus is a biphasic pulse waveform, which may but need not be symmetrical. The frequency of the biphasic pulse waveform may in some variations be between 30 Hz and 80 Hz.

In other variations, the devices may include an implantable microstimulator and an external controller. Exemplary implantable devices that may be used to apply the electrical stimulation described herein are disclosed in U.S. patent application Ser. No. 13/441,806, filed Apr. 6, 2012, and titled "Stimulation Devices and Methods," which is hereby incorporated by reference in its entirety. Exemplary hand-held devices, as well as additional exemplary implantable devices, that may be used to apply the electrical stimulation described herein are disclosed in U.S. patent application Ser. No. 14/256,915, filed Apr. 18, 2014, and titled "Nasal Stimulation Devices and Methods," which is hereby incorporated by reference in its entirety.

In general, the methods disclosed herein include applying electrical stimulation to an anatomical structure in an ocular region or a nasal region to activate the lacrimal gland, where the electrical stimulation is defined by a plurality of waveform parameters, and increasing tear production using the electrical stimulation. In some instances, the methods may comprise spatially controlling the stimulus delivery to target particular anatomical structure(s) and/or to modify the current pathways over time. The method may further include confirming activation of the lacrimal gland by evaluating a paresthesia sensed in the ocular region or the nasal region.

The anatomical structure that is stimulated may be a nerve, cutaneous sensory cells (Parcian corpuscles, Merkel cells etc.), muscle, or tissue such as mucosa or sub-mucosa, in the ocular region or nasal region. For example, the anatomical structure may be the nasociliary nerve, the anterior or posterior ethmoid nerve, or the infra-trochlear nerve. In some variations, the anatomical structure is a muscle in the ocular region or the nasal region. In some variations, the anatomical structure comprises a mucosal or sub-mucosal surface in the ocular region or the nasal region. In some instances, the anatomical structure may be cutaneous sensory cells in the nasal or ocular glabrous skin, which naturally sense mechanical input such as pressure, vibration, tingle, temperature, or pain.

As further described herein, the flow of current for stimulation may be spatially controlled. Current may be driven between particular contacts and thus through particular pathways through tissue, and may be driven via different pathways through tissue over time to spatially pattern the stimulus. Current steering and/or temporal patterning of waveform parameters may be optimized for a particular patient to activate the lacrimal gland to produce tears and elicit a paresthesia in that patient. Current steering and/or temporal patterning, where at least one of the waveform parameters is modulated over time, may also be determined based on other factors such as clinical markers, including but not limited to growth factor levels and/or osmolarity.

The plurality of waveform parameters that define the stimulation waveforms may be selected from the group consisting of on/off duration, frequency, pulse width, amplitude, and shape. Other suitable waveform parameters may also be used. For example, charge injection, which can be calculated by multiplying amplitude and pulse width, may be used as a waveform parameter. In some variations, the plurality of waveform parameters are selected from the group consisting of on/off duration, frequency, pulse width, amplitude, and shape. In some of these variations, the on/off duration ranges from about 0.1 to 5.0 seconds on, and about 0.1 to 5.0 seconds off. In some of these variations, the on/off duration is 1.0 second on, and 1.0 second off. In some of these variations, the on/off duration is 5.0 seconds on, and 5.0 seconds off. In some of these variations, the frequency ranges from about 10 to 200 Hz. In some of these variations, the frequency ranges from about 30 to 150 Hz. In some of these variations, the frequency ranges from about 50 to 80 Hz. In some variations, the frequency is 30 Hz. In some variations, the frequency is 70 Hz. In some variations, the amplitude ranges from about 0.1 to 10 mA. In some of these variations, the maximum amplitude ranges from about 1 to 3 mA. In some variations, the pulse width and amplitude generate a waveform having a triangular, rectangular, or square shape. In some variations, the electrical stimulation is continuously applied. In other variations, the electrical stimulation has on and off periods.

A particular combination of current steering and/or spatial or temporal patterning may be applied using a stimulator comprising a plurality of combinations stored in memory. Selection of the stored combinations may be random, predetermined, or controlled by a user. In some instances, the stored combinations may be patient-optimized waveforms.

Methods for treating dry eye in a patient in need thereof are described herein. In one variation, the method may comprise contacting nasal mucosa of the patient with an electrode, and delivering current from the electrode through tissue of the patient to a return contact, where the electrode is located on a nasal insertion prong of a stimulator probe of a stimulator, and the return contact is located on a stimulator body of the stimulator, and the stimulator probe is reversibly attachable to the stimulator body. The method may further comprise delivering current from the electrode through tissue of the patient to a second electrode. The second electrode may be located on the nasal insertion prong. In some instances, the current is delivered simultaneously from the electrode to the return contact and to the second electrode; in others, the current is delivered sequentially from the electrode to the return contact and to the second electrode. The electrode may contact the nasal mucosa in the anterior nasal cavity, and in some instances may contact the nasal mucosa at a location anterior to a middle or inferior turbinate of the nasal cavity.

Also described here are methods for treating a patient having dry eye using a stimulator comprising a stimulator body and a stimulator probe, wherein the stimulator probe comprises a nasal insertion prong comprising a first electrode and a second electrode. The method may comprise inserting the nasal insertion prong into a nostril of the patient, placing the first electrode and the second electrode in contact with nasal mucosa on a first side of a septum of the patient, placing a return contact in contact with tissue of the patient, and delivering an electrical stimulation waveform from the first electrode to the second electrode, and from the first electrode to the return contact. The first and second electrodes may be spaced longitudinally along the length of the nasal insertion prong, or they may be spaced radially around a circumference of the nasal insertion prong. In some variations of the method, no electrodes are placed in contact with nasal mucosa on a second side of the septum of the patient, and delivering the electrical stimulation waveform results in bilateral lacrimation.

Methods for increasing tear production in a patient are also described here. The methods may comprise delivering an electrical stimulus to tissue of a patient using a device comprising at least three electrical contacts, wherein the electrical stimulus takes one or more pathways between the at least three electrical contacts during delivery, and wherein the one or more pathways of the electrical stimulus change over time during delivery. The electrical stimulus may take two pathways between the at least three electrical contacts, such that a first amount of current takes the first pathway and a second amount of current takes the second pathway. In some instances, the ratio of the first amount to the second amount changes over time during delivery. The ratio may in some cases be changed by the patient using a user interface of the device. The device may be implantable, or it may be handheld. Some variations of the device have a single nasal insertion prong, which may comprise one electrode, two electrodes, or more. Some variations of the device comprise a stimulator body comprising an electrical contact configured to deliver current or act as a return contact.

In some variations the methods described herein comprise applying patterned electrical stimulation to an anatomical structure in an ocular region or a nasal region to activate the lacrimal gland, and increasing tear production using the patterned electrical stimulation, wherein the patterned electrical stimulation comprises a biphasic waveform having cathodic and anodic pulse pairs. In some variations, a subset of the pulse pairs have a leading cathodic pulse and a subset of the pulse pairs have a leading anodic pulse. In some variations, each pulse has a duration and amplitude, wherein the ratio of duration to amplitude for each pulse is variable over time. In some variations, the biphasic waveform is charge balanced. In some of these variations, the ratio of duration to amplitude for the cathodic pulse varies over time according to a function having a phase of exponential increase and a phase of exponential decrease. In some of these variations, the ratio of duration to amplitude for the cathodic pulse varies over time according to a sawtooth function. In some of these variations, the ratio of duration to amplitude for the cathodic pulse varies over time according to a sinusoidal function.

In some variations the methods described herein comprise implanting a stimulation device in an ocular region or a nasal region of a subject to activate the lacrimal gland, applying patterned electrical stimulation from the stimulation device, and increasing tear production using the patterned electrical stimulation, wherein tear production is bilateral. In some variations, the tear production is approximately equal in both eyes of the subject. Some variations of the methods described herein comprise delivering a stimulus to an ocular region or a nasal region of a subject to activate the lacrimal gland, wherein the stimulus is an electrical waveform, and increasing tear production using the patterned electrical stimulation, wherein tear production is bilateral. In some variations, the stimulus is delivered unilaterally.

The frequency, peak-to-peak amplitude, and pulse width of the waveforms may be constant, but in some variations the stimulator may be configured to vary the frequency, amplitude, and/or pulse width of the waveform. This variation may occur according to a pre-determined plan, or may be configured to occur randomly within given parameters. For example, in some variations the waveform may be configured such that the peak-to-peak amplitude of the waveform varies over time (e.g., according to a sinusoidal function having a beat frequency, a sawtoothed function, or an exponential function); in some variations the waveform may be configured such that the frequency of the waveform varies over time (e.g., according to a sinusoidal function, a sawtoothed function, or an exponential function); or in some variations the waveform may be configured such that the pulse width of the waveform varies over time (e.g., according to a sinusoidal function, a sawtoothed function, or an exponential function). In some variations, rectangular stimulation pulses of a variable fundamental frequency are employed. In other variations, triangular stimulation pulses may be used and modulated as described for rectangular stimulation pulses.

In some variations, the methods described herein comprise a method for inducing lacrimation. In some variations the method comprises delivering an electrical stimulus to a patient having dry eye, wherein the electrical stimulus is delivered from a handheld stimulator, and wherein the electrical stimulus comprises a waveform having a pulse width that varies during delivery. In some variations the method comprises delivering an electrical stimulus to a patient having dry eye using a handheld stimulator, wherein the electrical stimulus can be one of a plurality of preset waveforms comprising at least a first preset waveform and a second preset waveform, and changing the electrical stimulus from the first preset waveform to the second preset waveform while delivering the electrical stimulus. The electrical stimulus may be changed from the first preset waveform to the second preset waveform by the patient.

In some variations, the methods described herein comprise providing a device to a patient having dry eye, wherein the device is configured to deliver a plurality of electrical waveforms to an anatomical target in a patient, and instructing the patient to select one or more of the plurality of waveforms based on an amount of sensed paresthesia felt during delivery of the waveform. In some of these variations, the anatomical target may be the nasal mucosa. In some of these variations, the anatomical target may be the anterior ethmoidal nerve. In others of these variations, the anatomical target may be in an ocular region. In some of these variations, at least one of the plurality of waveforms may have a pulse width that varies over time. In some of these variations, the pulse width may vary over time according to an exponential function.

In some variations the methods described herein comprise methods of reducing patient accommodation to electrical stimuli in an ocular, orbital, or nasal region by using patterned waveforms.

In some variations the methods described herein comprise methods of preferentially activating different anatomical structures, comprising implanting a stimulation device, delivering a waveform having a biphasic pulse, and activating a different anatomical structure by modifying the waveform. In some variations, the waveform is modified by adjusting an amplitude of the biphasic pulse. In some variations, the waveform is modified by adjusting the order of a cathodic pulse and an anodic pulse of the biphasic pulse.

Devices for delivering an electrical stimulus to nasal mucosa of a patient are also described here. A device may comprise a stimulator probe comprising a nasal insertion prong, wherein a distal portion of the nasal insertion prong comprises first and second electrodes. The first electrode may be configured to deliver current. The device may also comprise a return contact located on the stimulator probe at the base of the nasal insertion prong, and may also comprise a user interface configured to allow the patient to adjust an amount of current delivered between the first and second electrodes and between the first electrode and the return contact. The first electrode, second electrode, and/or return contact may comprise a hydrogel. In some variations, the return contact has an annular shape. The return contact may be configured to contact tissue at or near a nostril.

A device for delivering an electrical stimulus to nasal mucosa of a patient having dry eye may also comprise a first nasal insertion prong, a second nasal insertion prong, and a user interface. The first nasal insertion prong may be configured to be inserted into a first nostril and may comprise a first electrode. The second nasal insertion prong may be configured to be inserted into a second nostril, and may comprise a second electrode. The device may be configured to deliver a biphasic charge-balanced pulsed waveform, where the user interface is configured to allow the patient to adjust an amplitude:duration aspect ratio of the waveform.

Systems for generating and applying the electrical stimulation waveforms are further disclosed herein. The systems may generally include one or more electrodes and a controller, wherein the controller comprises a programmable memory configured to store a plurality of patterned stimulation waveforms. The stimulation waveforms may or may not be associated with a sensed paresthesia. The controller may also be configured to execute a program that cycles through a plurality of stimulus options. A user interface may be included and configured in a manner that allows the patient to select one or more of the stored plurality of stimuli.

In some variations, the stimulators are configured for implantation in an ocular region or a nasal region. In some of these variations, the stimulators are configured for placement on a mucosal surface or within sub-mucosal tissue. The stimulators, which may for example comprise one, two, three, or more active electrodes, may also be configured for placement within a nasal cavity or a sinus cavity. In other variations, the controller is configured for placement external to the ocular region or the nasal region. In some variations, the electrical stimulation is applied by an electrode disposed within a nasal cavity or a sinus cavity. In some variations, the patterned electrical stimulation is applied by an electrode implanted near the lacrimal gland. In some of variations, the systems are configured for activating cutaneous sensors or nerve fibers innervating cutaneous sensors in the mucosal surface or within sub-mucosal tissue. In some variations, the systems are configured for activating cutaneous sensors or nerve fibers innervating cutaneous sensors in tissue such as skin and muscles of the ocular region, the forehead, or the temple area of the head.

In some variations, the patterned electrical stimulation is applied by a stimulator comprising a plurality of patterned stimulation waveforms stored in memory. In some of these variations, the applied patterned stimulation is randomly selected from the plurality of stored patterned stimulation waveforms. In some of these variations, the plurality of stored patterned stimulation waveforms are patient-optimized waveforms. In some variations, the applied patterned stimulation is stored in memory as a patient-optimized waveform.

In some variations the systems described herein comprise one or more stimulation electrodes and a controller, wherein the controller comprises a programmable memory configured to store a plurality of patterned stimulation waveforms associated with a sensed paresthesia. In some variations, the one or more stimulation electrodes are configured for implantation in an ocular region or a nasal region. In some of these variations, the controller is configured for placement external to the ocular region or the nasal region. In some variations, the one or more stimulation electrodes are configured for placement on a mucosal surface or within sub-mucosal tissue. In some variations, the one or more stimulation electrodes are configured for placement within a nasal cavity or a sinus cavity.

In some variations, the programmable memory is capable of storing up to 10 patterned stimulation waveforms. In some variations the system further comprises a user interface for selecting one or more of the stored plurality of patterned waveforms. In some variations, the controller is configured to execute a program that cycles through a plurality of waveform parameter options.

In some variations, the devices described herein comprise a handheld stimulator comprising a stimulator body comprising a user interface, and a stimulator probe comprising a nasal insertion prong comprising an electrode. The stimulator may be configured to deliver a plurality of electrical waveforms, and the user interface may be configured for selection of one of the plurality of electrical waveforms. Each of the waveforms may have at least one of a pulse shape, maximum amplitude, pulse width, or frequency that is modulated over time. In some of these variations, each of the waveforms has at least two of a pulse shape, maximum amplitude, pulse width, or frequency that is modulated over time. In some variations, each of the waveforms has a pulse shape that is modulated over time. In some variations, the waveform comprises a first period comprising a two-phase current-controlled waveform, and a second period comprising a current-controlled phase followed by a voltage-controlled phase.

BRIEF DESCRIPTION OF THE DRAWINGS

FIGS. 5A-5C show exemplary waveforms.

FIGS. 19A-19B illustrate distal portions of exemplary nasal insertion prongs.

FIG. 25 illustrates a distal portion of an exemplary nasal insertion prong.

FIG. 26 shows a perspective view of an exemplary handheld nasal stimulator having a single nasal insertion prong.

FIGS. 27A-27C, 28A-28B, and 29A-29B are perspective views of exemplary handheld nasal stimulators having return contacts.

DETAILED DESCRIPTION

Described herein are devices, systems, and methods for treating one or more conditions (such as dry eye, tired eyes, ocular discomfort from wearing contact lenses, etc.) by providing electrical stimulation to an anatomical structure located in an ocular region or a nasal region. Specifically, the methods disclosed herein generally include applying electrical stimulation to an anatomical structure in an ocular region or a nasal region to activate the lacrimal gland, where the electrical stimulation is defined by a plurality of waveform parameters. The electrical stimulation may result in effects such as increased tear production during or after delivery of the stimulus.

Figure 1:
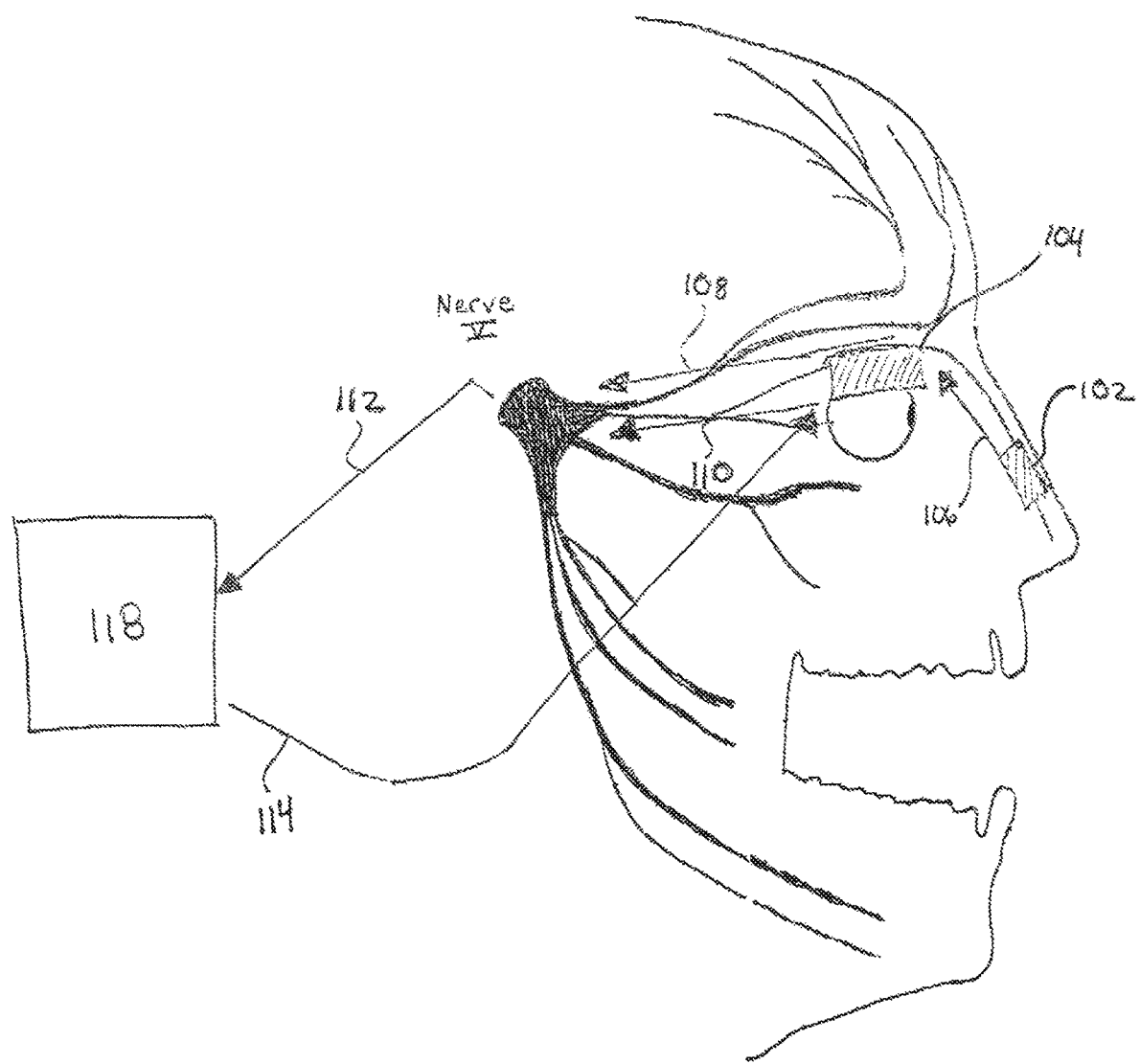
FIG. 1 illustrates a proposed pathway of action of sensory output processed in various ganglia of the peripheral nervous system and nuclei of the central nervous system.

In general, the methods disclosed herein include electrically stimulating nerves, muscles (thus indirectly nerves via muscle spindles and golgi-tendon receptors providing sensory information back to the central nervous system), and/or glands in the orbit of the eye or the nasal mucosa and sub-mucosa. With that approach, neural tissue may be activated in some manner. For example, referring to FIG. 1, the inventors hypothesize that the activation at an intra-nasal location 102 or at an ocular location 104 causes action potentials to run antidromically and orthodromically from the activation point if the electrode is activating the nerves directly, and orthodromically on afferent nerves if glands and muscles are activated to cause sensory input to the brain. Sensory input to the brain reaches the lacrimal nucleus in the pons, after passing several ganglia on the way, as shown by arrows 106, 108, 110, and 112. Here it is likely that neural computation and data reduction happens in each of the ganglia as well as in the nuclei in the pons before the information is further relayed to areas of the sensory cortex in the cerebrum. Accordingly, the activation of neural tissue, directly or indirectly, may cause circuitry in the central nervous system (e.g., brain, spinal cord, potentially the ganglia in the peripheral nervous system) to respond to the input. Output from the brainstem 118 may then send feedback, as shown by arrow 114, to the lacrimal gland.

Exemplary Stimulators

The stimulation waveforms described herein may be delivered via implanted or non-implanted (e.g., handheld) stimulators.

Exemplary Implantable Microstimulators

Figure 2A:
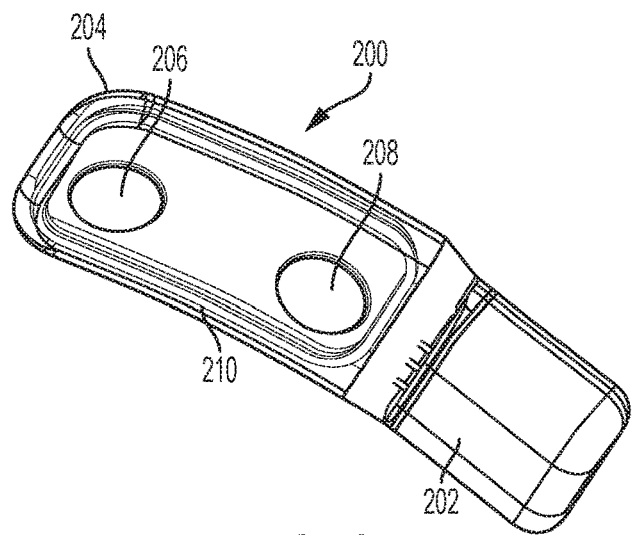
FIGS. 2A-2C depict an exemplary implantable microstimulator.
Figure 2B:
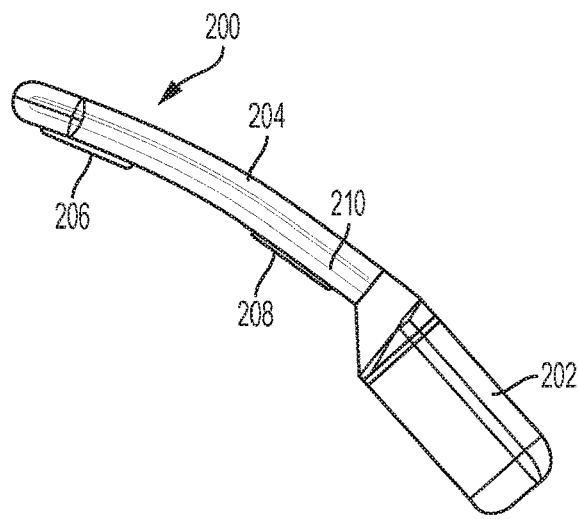
Figure 2C:
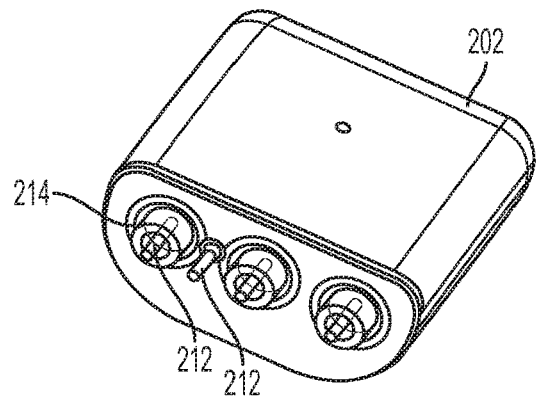

When the stimulation waveforms described herein are applied using an implantable stimulator, the stimulator may comprise a microstimulator comprising a housing and a corresponding and complementary flexible extension connected to the housing, forming a unitary microstimulator. An example is shown in FIGS. 2A-2C. As shown there, the microstimulator 200 may comprise a housing 202 and a flexible extension 204 connected to the housing 202. The housing 202 may be hermetically sealed, and may contain some or all of the stimulation circuitry therein. The microstimulator 200 may comprise any suitable stimulation circuits, such as those described in U.S. patent application Ser. No. 13/441,806, which was previously incorporated by reference in its entirety. The housing 202 may be formed from one or more metals (e.g., titanium) or other biocompatible materials.

The extension 204 may be formed from a flexible material such as silicone, and may comprise a first electrode 206, a second electrode 208, and a coil 210. While shown as having two electrodes, implantable stimulators may have fewer (e.g., one) or more (e.g., three, four, five, six, or more) electrodes. When the implantable stimulator comprises a plurality of electrodes, the current pathways through tissue may be controlled by delivering the current to/from various electrodes, which may be varied over time. In some variations, the extension 204 may be a molded component, such as molded silicone. The extension may have a corresponding and complementary shape to the housing, such that the extension and housing together have a unitary shape, as shown in FIGS. 2A-2B. The flexible extension 204 may conform to one or more portions of the anatomy (e.g., the orbit or the lacrimal gland) when implanted in tissue. FIG. 2B shows a side view of the microstimulator 200. As shown there, the thickness of the extension 204 may be less than that of the housing 202, and may increase to the thickness of housing 202. Additionally, the width of the extension 204 is shown in FIG. 2A as being greater than the width of the housing 202, and may decrease to the thickness of the housing 202.

The electrodes 206 and 208 and coil 210 may be connected to the microstimulator circuitry via one or more feedthroughs. For example, FIG. 2C shows a perspective view of the housing 202 with the extension 204 removed. As shown there, housing 202 may comprise a plurality of feedthroughs 212 that extend through the housing 202. One or more elements (e.g., one of the electrodes 206 or 208 or the coil 210) may be electrically connected to the hermetically-sealed stimulation circuitry by connection to the feedthroughs 212. Additionally, some of the feedthroughs 212 may comprise an insulating member 214 which may electrically isolate the feedthrough 212 from the housing 202. This and other implantable stimulators that may deliver the electrical stimuli described herein are described in U.S. patent application Ser. No. 13/441,806, which was previously incorporated by reference in its entirety; and in U.S. patent application Ser. No. 14/256,915, which was previously incorporated by reference in its entirety.

When the stimulator is an implantable microstimulator, the system may further comprise a controller, which may communicate with the microstimulator to transmit and/or receive power, information, or the like. For example, in variations in which a stimulation system comprises a microstimulator having a passive stimulation circuit (or a stimulation circuit that does not otherwise include a battery or internal power supply), the controller signal may power the stimulator via the output signal of the controller. The controller may communicate with the microstimulator wirelessly and/or via a wired connection. The controller may be configured for implantation within the body, or may be configured to remain external to the body. The controller may be disposable, may be reusable, or may be partially reusable. In some instances, the controller may be rechargeable.

Figure 3:
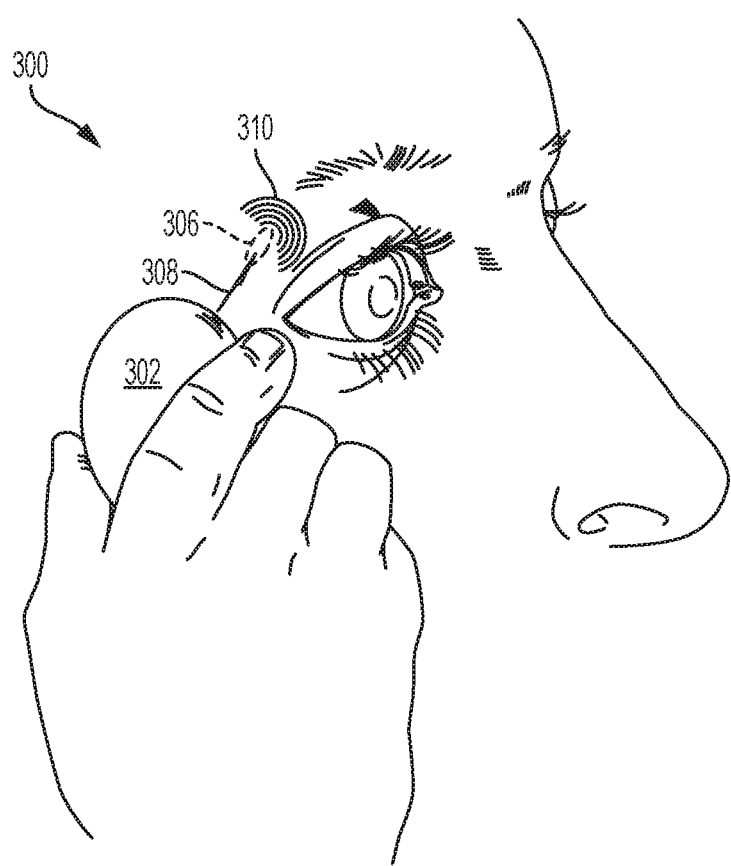
FIG. 3 depicts an exemplary external controller for an implantable microstimulator.

FIG. 3 depicts an exemplary external controller. As shown there, a stimulation system 300 includes a controller 302 comprising a hand-held device. The controller 302 may be brought into the vicinity of an implanted microstimulator 306, and may produce an output signal 308 received by the implanted microstimulator 306. The implanted microstimulator may in turn generate a stimulation signal 310 used to stimulate an anatomical target, as described in more detail herein. This and other controllers that may be used to deliver the electrical stimuli described herein are described in U.S. patent application Ser. No. 13/441,806, which was previously incorporated by reference in its entirety.

The length and width of the microstimulator may be selected to permit placement of a portion of the microstimulator on, partially within or about the lacrimal gland, or adjacent to a desired tissue, such as the lacrimal gland or a nerve desired to be stimulated, such as but not limited to the nasociliary nerve or anterior ethmoidal nerve. Some of these implantation locations are described in more detail in U.S. patent application Ser. No. 13/441,806, which was previously incorporated by reference in its entirety; in U.S. patent application Ser. No. 14/256,915, which was previously incorporated by reference in its entirety; and in U.S. patent application Ser. No. 14/207,072, filed Mar. 12, 2014, and titled "Implant Delivery Devices, Systems, and Methods," which is hereby incorporated by reference in its entirety.

The microstimulator may be injectable into a patient using a delivery system. The delivery system may comprise an insertion device (such as conduit, a shaft to which the microstimulator is removably attachable, or the like) and/or a dissection tool. In some variations, the insertion device is a 12 or larger gauge needle. In other variations, the insertion device comprises a cannula. In some variations, the insertion device may comprise a piston assembly, which in some variations may be spring-powered. The microstimulator may be loaded into the insertion device, and the insertion device may be inserted into an insertion pathway. In some variations in which the microstimulator is implanted into an ocular region, using an anatomical landmark at the corner of the eye, a delivery device (e.g., a needle) may be positioned in proximity to the lacrimal gland, and the microstimulator may be deployed using the delivery device. Anatomical landmarks include, but are not limited to, the lateral canthis, an eyelid margin, a palpebral lobe of the lacrimal gland, the orbital rim, a bony protuberance on the superior-lateral aspect of the orbit, the vascular bed, or the like. In some variations, a microstimulator may be implanted by lifting the eyelid, forming an insertion pathway through the conjunctiva under the eyelid, and advancing the microstimulator into the insertion pathway. The insertion pathway may be formed using a dissection tool. In some variations, the insertion pathway may be formed using a dissection element of an insertion tool. In some variations, the insertion pathway may be formed between the periosteum and the orbital bone. In other variations, the insertion pathway may be formed between the periosteum and the lacrimal gland. The microstimulator may have one or more features to facilitate minimally invasive retrieval. U.S. patent application Ser. No. 14/207,072, which was previously incorporated by reference in its entirely, describes other variations of insertion devices that may be used to implant microstimulators described herein.

Exemplary Handheld Stimulators

The stimulator described here may also be handheld. The handheld stimulators may comprise a stimulator body and a stimulator probe. The stimulator probe may comprise at least one nasal insertion prong configured to be inserted into a nostril of a subject. The stimulator body may be configured to generate a stimulus, which may be delivered to the subject via the nasal insertion prong. The stimulator body may comprise a control subsystem and a power source, which together may generate and control the stimulus.

Figure 4A:
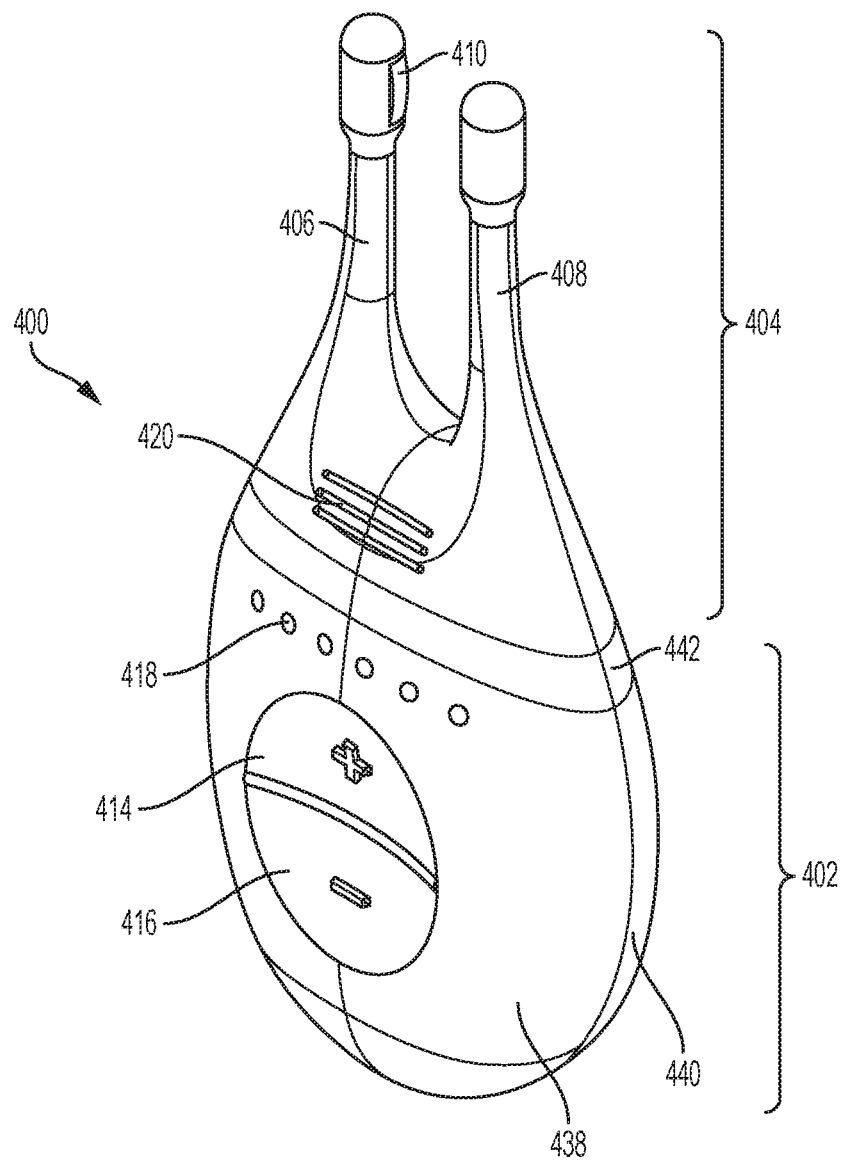
FIGS. 4A-4C depict an exemplary handheld stimulator.
Figure 4C:
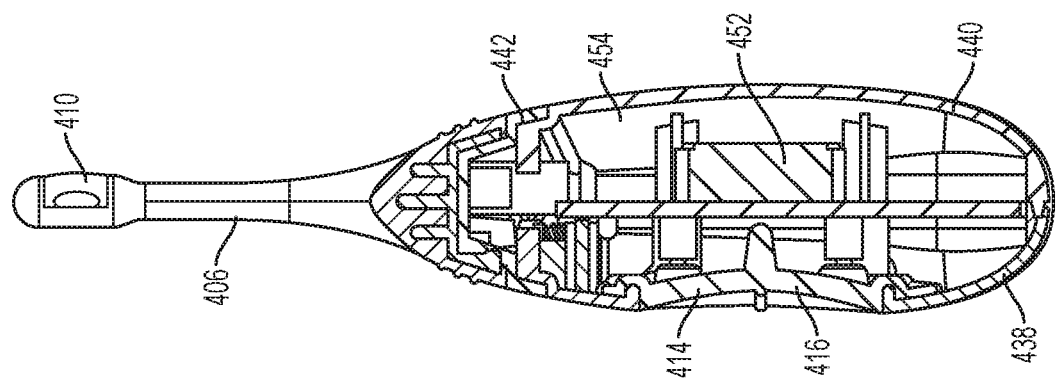
Figure 4B:
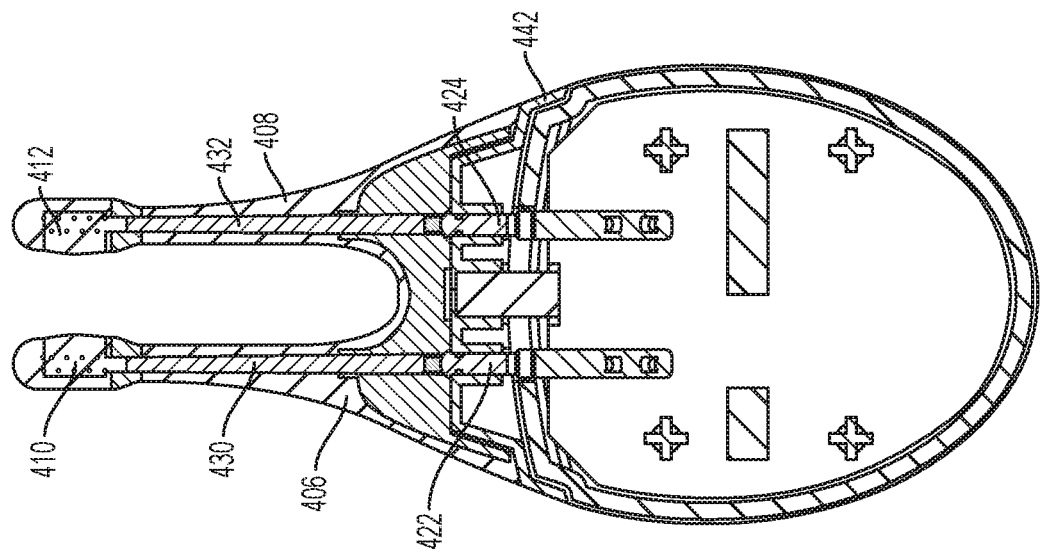

One variation of a handheld stimulator is shown in FIGS. 4A-4C. These figures show perspective, cut-away back, and cut-away side views, respectively, of a handheld stimulator 400, respectively. The stimulator 400 comprises a stimulator body 402 and a stimulator probe 404. The stimulator body 402 may comprise a front housing 438, back housing 440, and proximal housing 442, which may fit together to define a body cavity 454. The body cavity 454 may contain a control subsystem and a power source 452.

The stimulator body may comprise a user interface comprising one or more operating mechanisms to adjust one or more parameters of the stimulus, as described in more detail below. The operating mechanisms may provide information to the control subsystem, which may comprise a processor, memory, and/or stimulation subsystem. In some variations, the operating mechanisms may comprise first and second buttons, as illustrated for example in FIGS. 4A and 4C as 414 and 416. In some variations, pressing the first button may turn on the stimulator and/or change the stimulus waveform, while pressing the second button may turn off the stimulator and/or change the stimulus waveform. Additionally or alternatively, the user interface may comprise one or more feedback elements (e.g., based on light, sound, vibration, or the like). As shown in FIG. 4A, the user feedback elements may comprise light-based indicators, shown there as indicators 418, which may provide information to the user. It should be appreciated these features may be present in each of the handheld stimulator devices comprises herein.

For each handheld stimulator described herein, in some variations the stimulator body and stimulator probe may be reversibly attachable. Some or all of the stimulator may be disposable, and some or all of the stimulator may be reusable. For example, in variations where the stimulator probe is releasably connected to the stimulator body, the stimulator body may be reusable, and the stimulator probe may be disposable and periodically replaced. In some of these variations, the device comprises a disabling mechanism that prevents stimulus delivery to the subject when the stimulator probe is reconnected to the stimulator body after being disconnected from the stimulator body. Additionally or alternatively, the device may comprise a lockout mechanism that prevents the stimulator probe from being reconnected to the stimulator body after being disconnected from the stimulator body. In some variations, the device further comprises a detachable protective cap. The stimulators described herein may have additional features as described in more detail in U.S. patent application Ser. No. 14/256, 915, which was previously incorporated by reference in its entirety.

For each handheld stimulator described herein, the stimulator probe may comprise at least one nasal insertion prong. In the handheld stimulator variation shown in FIGS. 4A-4C, for example, the stimulator probe 404 may comprise two nasal insertion prongs 406 and 408. The nasal insertion prongs may be self-aligning when inserted into the nostrils of the patient. The stimulator probe 404 may further comprise ridges 420, which may allow the patient to more easily grip the probe 404. The nasal insertion prong may be configured to be at least partially inserted into the nasal cavity of a patient. A nasal insertion prong may extend from a base member of the stimulator probe and may comprise an elongate portion having at its distal end a distal portion. The length of a nasal insertion prongs is desirably long enough such that the prongs can reach the desired stimulation location (e.g., the nasal mucosa superior to the columella, such as near the interface between the nasal bone and the upper lateral cartilage) in a range of patients. A nasal insertion prong may comprise a flexible material (e.g., a flexible polymer, such as a thermoplastic elastomer (e.g., a thermoplastic elastomer alloy (e.g., Versaflex™), thermoplastic polyurethane, or the like), silicone, or the like) in order to allow the nasal insertion prong to self-align to the desired stimulation location when inserted into a user's nasal cavities and/or to be atraumatic to the nasal tissue during regular use and insertion, and/or during a sudden movement (e.g., a sneeze). This may also improve comfort for the user. In some variations, the desired hardness of the material may be between about 40 D and about 90 D, between about 50 D and about 80 D, between about 60 D and about 70 D, or about 65 D. In addition to having material properties that may be atraumatic to nasal tissue, it may be desirable for the distal tip of the nasal insertion prong to have rounded edges to help minimize the risk of tissue damage during advancement of the prong into the nose.

In some variations, the distal portion may have a diameter (or greatest cross-sectional dimension) that is larger than the diameter (or greatest cross-sectional dimension) of the elongate portion of the prong proximal to the distal portion. This may allow a portion of the distal portion (e.g., one or more electrodes, described below) to be brought into contact with a subject's tissue, while the elongate portion is not in contact with the subject's tissue. For example, the diameter of the nasal insertion prong at the distal portion may in some instances be between about 3 mm and about 7 mm, while the diameter of the elongate portion may be between about 1 mm and about 6 mm proximal to the distal portion. More specifically, in some variations the diameter of the nasal insertion prong may be about 5 mm, and the diameter of the elongate portion may be about 3 mm. The proximal portion of the elongate portion may flare outward (i.e., have an increasing diameter or greatest cross-sectional dimension) toward a base member of the stimulator probe, which may in some variations act as a stop to limit the distance that the nasal insertion prong may be advanced into the nose of a user.

Each nasal insertion prong may comprise at least one electrode. Each electrode may be connected to a lead, which may be directly or indirectly connected to a control subsystem and power source, such that an electrical stimulus may travel from the control subsystem, through the leads, and through the electrodes, as described in more detail in U.S. patent application Ser. No. 14/256,915, which was previously incorporated by reference in its entirety.

An electrode may have any suitable design. For example, an electrode may comprise an arc of a cylindrical surface, may be ellipsoid, spherical, ovoid, or the like. An electrode may have any suitable length, such as between about 1 mm and about 10 mm, between about 3 mm and about 7 mm, about 5 mm, or more than about 10 mm. An electrode may be positioned on any suitable longitudinal portion of a nasal insertion prong, and for nasal insertion prongs comprising a plurality of electrodes, may be spaced along the nasal insertion prong. The position of the electrode along the prong may at least partially determine the placement of the electrode relative to tissue when the stimulator probe is advanced into the nose. In some variations, an electrode may be located at an intermediate position along a prong. The electrode may be located any suitable distance from the distal tip of the prong, such as between about 0.1 mm and about 4 mm, about 4 mm and about 8 mm, or more than 8 mm from the distal dip of the prong (e.g., 1 cm from the distal tip). In some variations, an electrode may be located about 2.5 mm from the distal tip of the prong. In some variations in which an electrode is configured to deliver current, the electrode may be located such that when inserted into the nasal cavity, the electrode is capable of reaching the nasal mucosa or other area desired to be stimulated. In some variations, the distance from the base member of the stimulator probe to the longitudinal center of an electrode configured to deliver current (i.e., the farthest the center of the electrode could be inserted into the nasal cavity) may be between about 25 mm and about 45 mm. In other variations, the distance from the base member of the stimulator probe to the longitudinal center of at least one electrode may be between about 30 mm and about 40 mm. For example, in some variations the distance from the base member of the stimulator probe to the longitudinal center of at least one electrode may be about 32.5 mm. However, it should be appreciated that an electrode may be located at other positions, especially when the electrode is configured to be a return electrode. An electrode may also be connected to a distal end of a nasal insertion prong. Generally, when an electrode is positioned at the distal end of a prong, it may be desirable that the electrode have no edges, or rounded edges, to help minimize the risk of tissue damage during advancement of the electrode into the nose.

In some variations, the electrode comprises a hydrogel, which is described in more detail in U.S. patent application Ser. No. 14/630,471, filed Feb. 24, 2015, and titled "Polymer Formulations for Nasolacrimal Stimulation," which is hereby incorporated by reference in its entirety. However, it should be appreciated that electrodes described herein may comprise other conductive materials, such as metals (e.g., stainless steel, titanium, tantalum, platinum or platinum-iridium, other alloys thereof, or the like), conductive ceramics (e.g., titanium nitride), liquids, gels, or the like. In some variations, the electrode may comprise one or more materials configured to promote electrical contact between electrodes of the stimulator probe and tissue (i.e., all of an electrode or a portion of the electrode, such as a covering). In some instances, the impedance provided by tissue may be at least partially dependent on the presence or absence of fluid-like materials (e.g., mucous) in the nasal cavity. The material(s) may help to minimize the impact of subject tissue impedance by providing a wet interface between the electrode and tissue, which may act to normalize the impedance experienced by the electrode. This may in turn normalize the output and sensation experienced by the user.

The stimulators described herein may comprise at least one lead configured to electrically connect the electrode(s) to the stimulator body circuitry. A lead may extend at least partially through a nasal insertion prong and may be formed from one or more conductive materials (e.g., stainless steel, titanium, platinum or platinum-iridium, other alloys thereof, or the like), conductive ceramics (e.g., titanium nitride), and may be positioned such that at least a portion of the lead contacts the electrode to provide a conduction pathway between the lead and the electrode. In some variations, a lead may comprise a spring, but it should be appreciated that a lead may also comprise a conductive loop, a post, or the like.

In the exemplary handheld stimulator 400 FIGS. 4A-4C, the probe 404 comprises a first electrode 410 on nasal insertion prong 406 and a second electrode 412 on nasal insertion prong 408. As shown in the cut-away view of the stimulator 400 in FIG. 4B, the electrodes 410 and 412 are connected to leads 430 and 432 located within prongs 406 and 408, respectively. The leads 430 and 432 are in turn connected to connectors 422 and 424, respectively. Connectors 422 and 424 extend through lumens 408 and 410 in the proximal housing 442, and may connect directly or indirectly to the control subsystem and power source 452. As such, the electrical stimulus may travel from the control subsystem through the connectors 422 and 424, through the leads 430 and 432, and through the electrodes 410 and 412.

Figure 20:
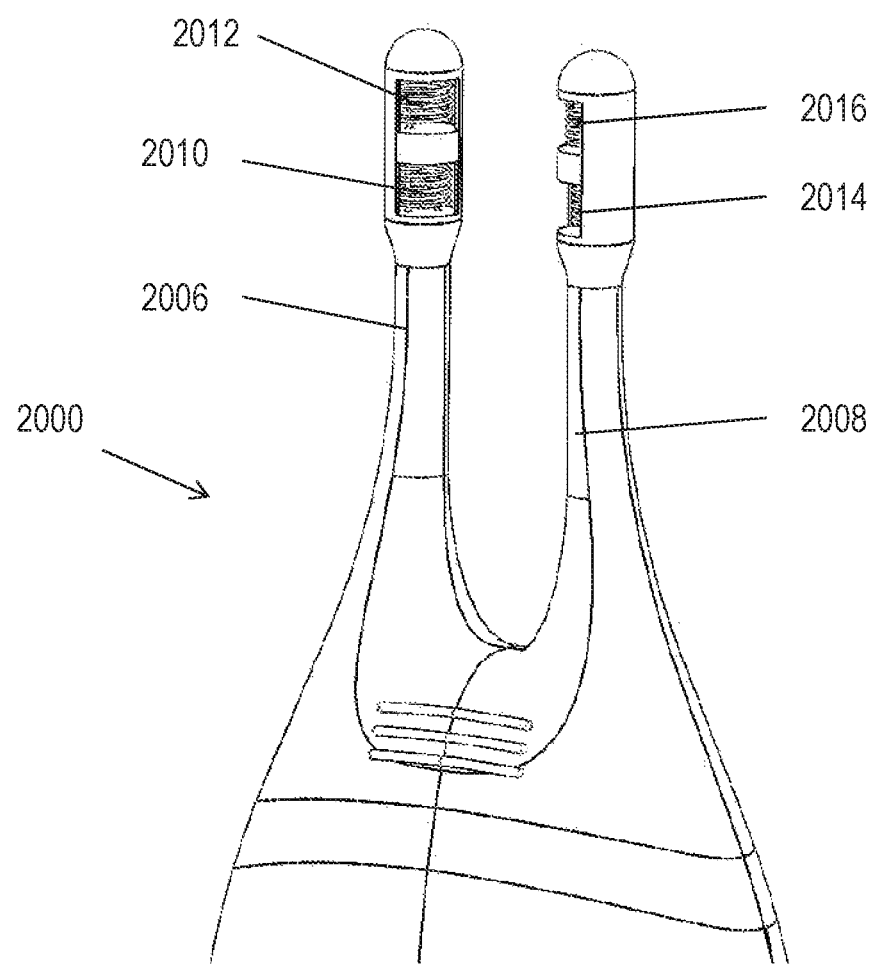
FIG. 20 shows a distal portion of an exemplary handheld nasal stimulator having two nasal insertion prongs.

While stimulator 400 is shown having two nasal insertion prongs, each comprising a single electrode, in other variations stimulators may comprise a single nasal insertion prong, and/or may comprise a plurality of electrodes on a nasal insertion prong. In some variations comprising a plurality of electrodes on a nasal insertion prong, the electrodes may be spaced longitudinally along the length of the nasal insertion prong, such that they are configured to contact nasal tissue at differing depths within the anterior nasal cavity when inserted into a nostril. FIG. 19A shows an example of the distal end of such a nasal insertion prong 1900, comprising a distal electrode 1902 and a proximal electrode 1904. As shown there, each electrode comprises a hydrogel contacted by a lead comprising a spring, but it should be appreciated that the electrodes and leads may have other configurations, as described herein. FIG. 20 shows a portion of an exemplary handheld stimulator 2000 comprising two nasal insertion prongs 2006 and 2008, which each comprise two such electrodes: first electrodes 2010 and 2014 located more proximally on the prong, and second electrodes 2012 and 2016 located more distally on the prong.

Figures 21A, 21B:
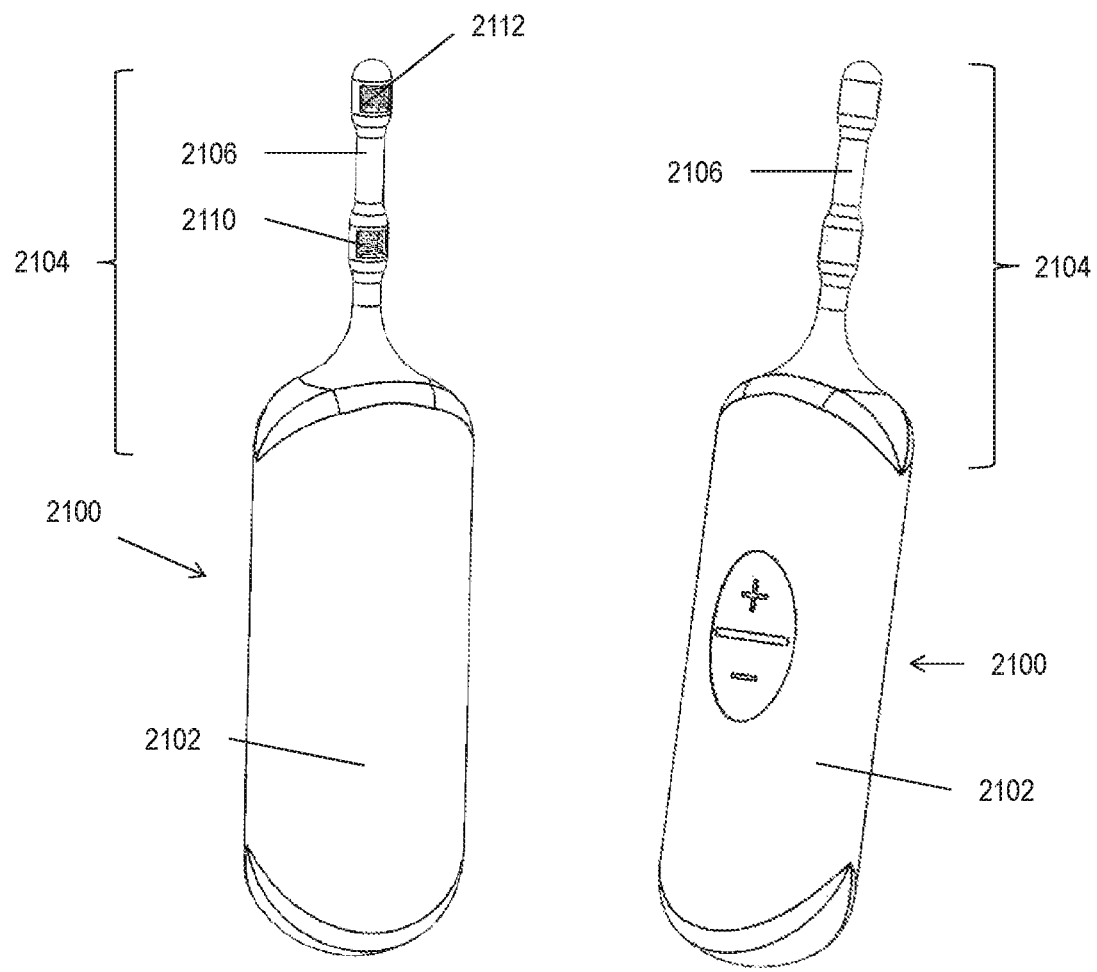
FIGS. 21A-21B depict perspective views of an exemplary handheld nasal stimulator having a single nasal insertion prong.

While FIGS. 19A and 20 show the distal and proximal electrodes as separated by a shorter distance than the length of each electrode, it should be appreciated that the electrodes may be longitudinally separated by any suitable distance. For example, FIG. 19B shows an example of a distal end of a nasal insertion prong 1950, comprising a distal electrode 1952 and proximal electrode 1954 separated by a larger distance than the length of each electrode. FIGS. 21A-21B show another exemplary stimulator 2100 comprising a stimulator body 2102 and a stimulator probe 2104 comprising a single nasal insertion prong 2106, where the nasal insertion prong comprises two electrodes spaced longitudinally along the prong. As shown in FIG. 21A, the nasal insertion prong 2106 may comprise a first electrode 2110 and a second electrode 2112, separated longitudinally along the nasal insertion prong by a larger distance than the length of the electrodes. As shown there, each electrode comprises a hydrogel contacted by a lead comprising a spring, but it should be appreciated that the electrodes and leads may have other configurations, as described herein.

Figure 22A:
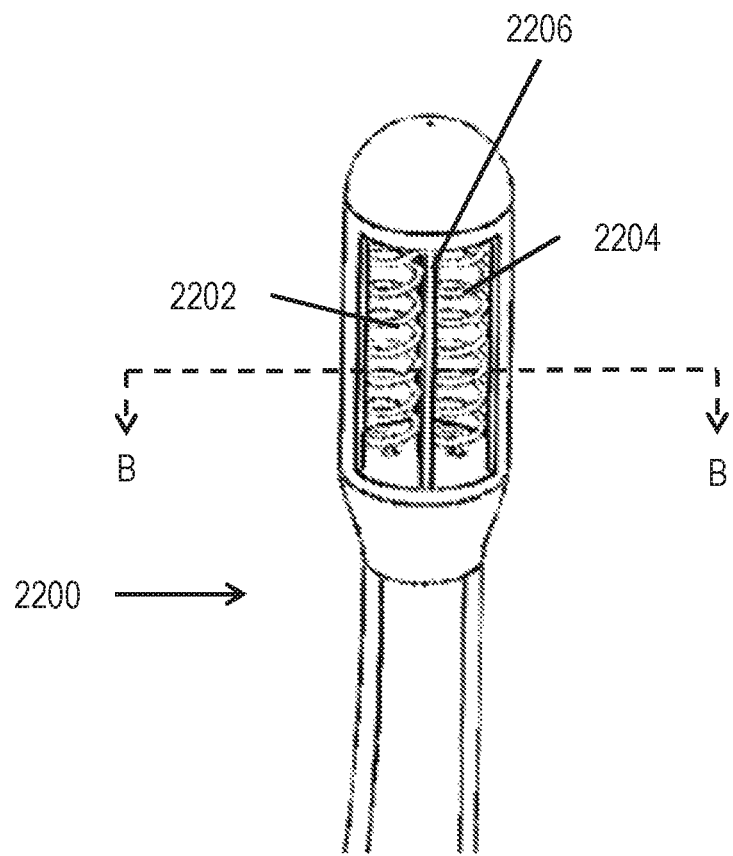
FIG. 22A shows a distal portion of an exemplary nasal insertion prong.
Figure 22B:
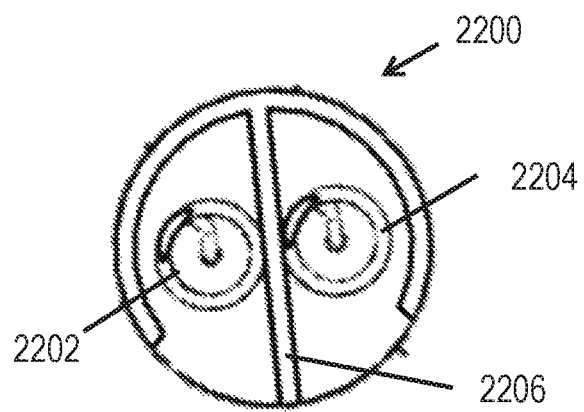
FIG. 22B shows a cross-sectional view of the nasal insertion prong of FIG. 22A.
Figure 23A:
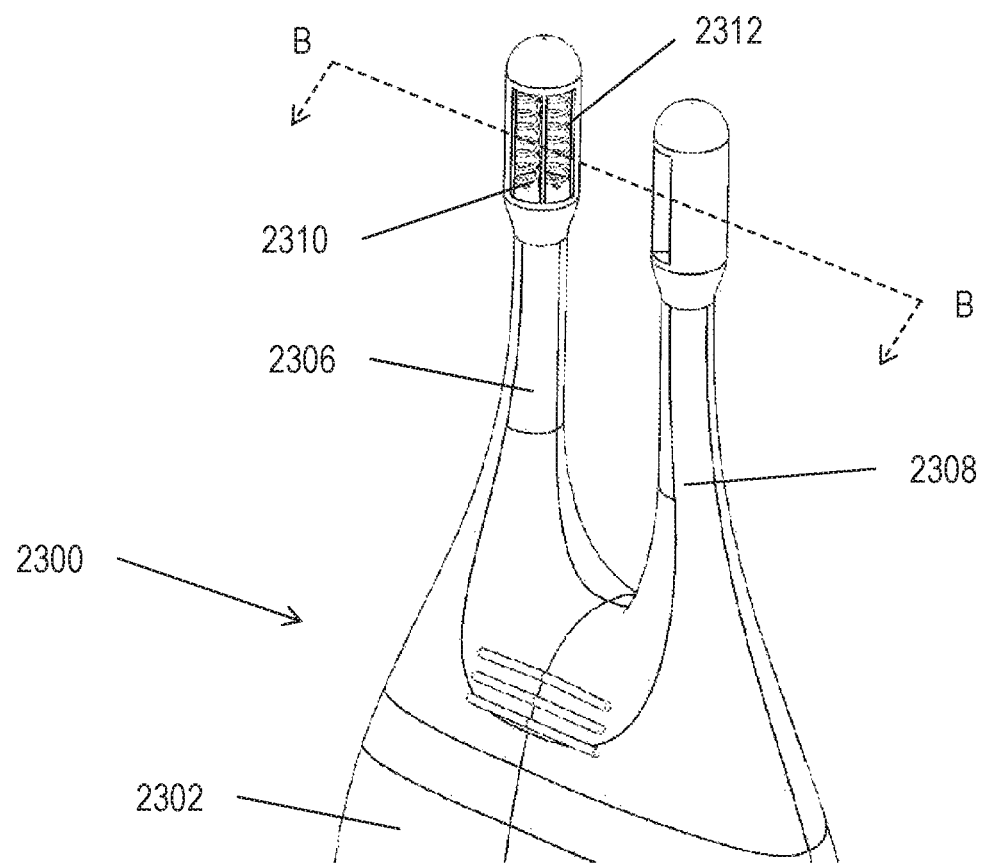
FIG. 23A shows a distal portion of an exemplary handheld nasal stimulator having two nasal insertion prongs.
Figure 23B:
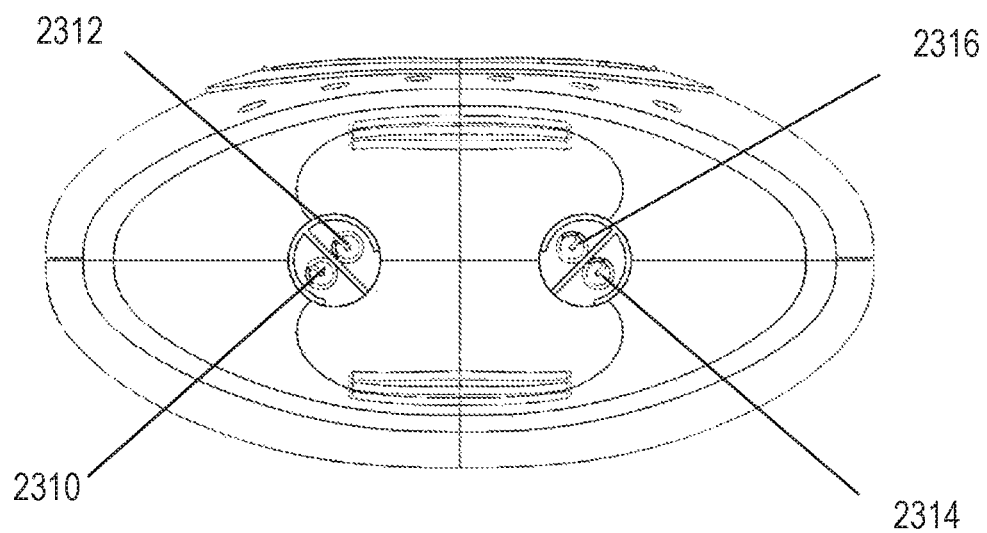
FIG. 23B shows a cut-away view of the handheld nasal stimulator of FIG. 23A.
Figure 24:
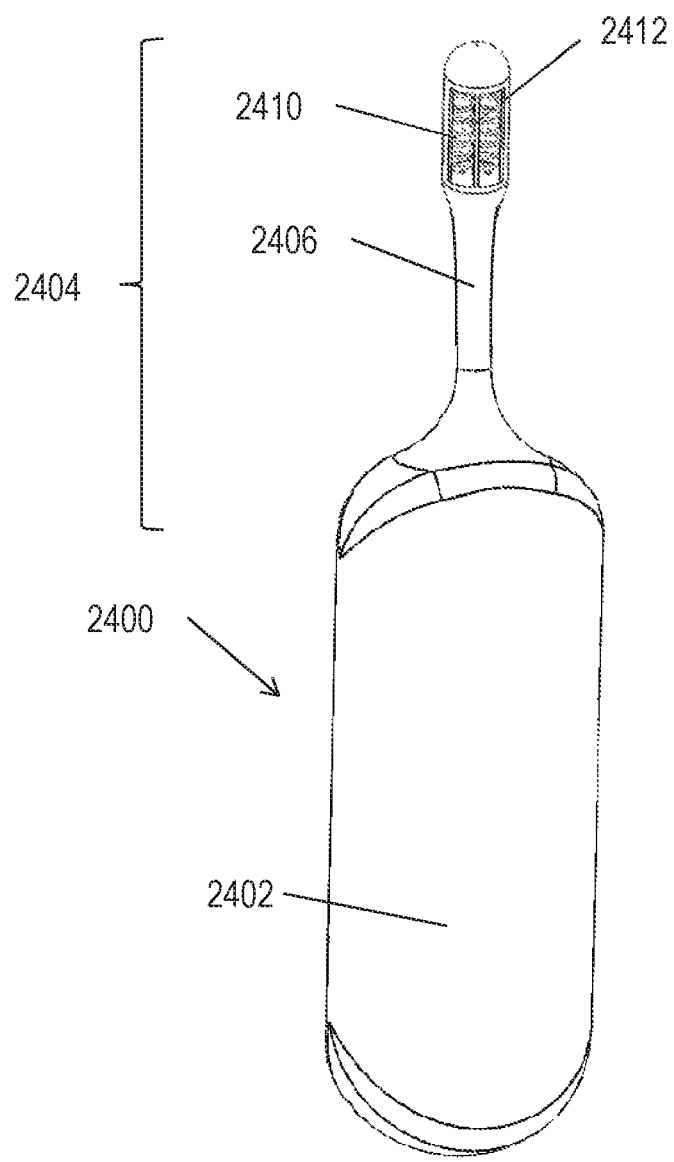
FIG. 24 depicts a perspective view of an exemplary handheld nasal stimulator having a single nasal insertion prong.

In other variations, more than one electrode may be located at the same longitudinal location along the length of the nasal insertion prong. In these variations, the electrodes may be at different locations around the circumference of a nasal insertion prong, i.e., spaced radially around the nasal insertion prong, such that they are configured to contact nasal tissue at different locations at the same depth within the anterior nasal cavity when the nasal insertion prong is inserted into a nostril. For example, when placed into a nostril, an electrode may face toward the front of the nose and another electrode may face toward the septum. In some instances, each electrode may comprise a partial cylinder (e.g., an arc of between about 10 degrees and 180 degrees). FIG. 22A shows an example of a distal end of such a nasal insertion prong 2200, comprising a first electrode 2202 and a second electrode 2204 separated by a vertical rib 2206. FIG. 22B shows a cross-sectional view of the nasal insertion prong 2200. FIGS. 23A and 23B show perspective and cut-away views, respectively, of a handheld stimulator 2300 comprising two nasal insertion prongs 2306 and 2308 each having first and second electrodes separated by a vertical rib. More specifically, each nasal insertion prong comprises a pair of electrodes, 2310, 2312 and 2314, 2316, respectively. Electrode pairs 2310, 2312 and 2314, 2316 are located at the same longitudinal location along the length of the nasal insertion prongs, spaced around the circumference. As another example, FIG. 24 shows an exemplary stimulator 2400 comprising a stimulator body 2402 and a stimulator probe 2404 comprising a single nasal insertion prong 2406, where the nasal insertion prong comprises first and second electrodes 2410 and 2412 spaced radially around the circumference of the nasal insertion prong. Although each electrode in FIGS. 22-24 is shown as comprising a hydrogel contacted by a lead comprising a spring, it should be appreciated that the electrodes and leads may have other configurations, as described herein.

In yet other variations, the electrodes may be spaced both longitudinally along the length of the nasal insertion prong and radially around the circumference of the nasal insertion prong. FIG. 25 shows an example of the distal end of such a nasal insertion prong 2500, comprising three electrodes: a distal electrode 2502 and first and second proximal electrodes 2504 and 2506 separated by a vertical rib 2508. As shown there, electrodes 2504 and 2506 have a common longitudinal location (i.e., are locate horizontally adjacent to each other) and are located proximally relative to electrode 2502. FIG. 26 shows an exemplary handheld stimulator 2600 comprising a stimulator body 2602 and a stimulator probe 2604 comprising a single nasal insertion prong 2606, where the nasal insertion prong comprises electrodes spaced both longitudinally along the length of the prong and radially around the circumference of the prong. Electrode 2610 is located distally to electrodes 2612 and 2614, which are spaced radially around the nasal insertion prong 2606 and separated by a vertical rib 2616. Although each electrode in FIGS. 25-26 is shown as comprising a hydrogel contacted by a lead comprising a spring, it should be appreciated that the electrodes and leads may have other configurations, as described herein.

It should be appreciated that although the examples described above comprise one, two, or three electrodes on the nasal insertion prongs, nasal insertion prongs may have more (e.g., four, five, six, or more) electrodes, which may be spaced longitudinally along and/or radially around a nasal insertion prong in any suitable arrangement. In some instances, each electrode may have a separate lead, while in others, one or more electrodes may have electrically connected leads (i.e., may be at the same potential).

Additionally or alternatively, some variations of handheld stimulators may comprise a return contact not located on a nasal insertion prong, which may provide an alternative or additional current pathway. For example, a handheld stimulator may comprise a return contact located on the base member of a stimulator probe or on a stimulator body. The return contact may be configured to be in contact with various anatomical locations, such as but not limited to a hand or an area of tissue near the opening of the nostril, the columella, the philtrum, or the upper lip. Further, it should be appreciate that in the configurations described herein, the return contacts may instead be configured to deliver current.

For example, FIGS. 27A-27B show exemplary handheld nasal stimulators each comprising a single prong and a return contact not located on the nasal insertion prong. Shown there are handheld nasal stimulators 2700 and 2740 each having return contacts 2702 and 2742 located on the stimulator bodies 2704 and 2744, respectively. As such, the return contacts may be configured to be in contact with the hand of a user, while the active electrodes 2706 and 2746, 2748 are configured to be in contact with the nasal mucosa. FIG. 27C shows a nasal stimulator 2720 comprising two nasal insertion prongs, each with an electrode, and comprising a return contact 2722 located on a stimulator body 2724. As shown in FIGS. 27A-27C, handheld stimulators comprising return contacts located on a stimulator body may have any suitable number of electrodes located on a nasal insertion prong, such as one per prong (FIGS. 27A and 27C), two (FIG. 27B), three, four, five, six, or more active electrodes.

The return contacts in FIGS. 27A-27C are shown as each comprising a band around the stimulator bodies, but return contacts configured to contact the hand of a user may have any suitable shape. For example, a return contact may comprise a plurality of intersecting bands to accommodate various ways in which a user might hold the stimulator, or a plurality of bands or surfaces at the same potential spaced around the stimulator body. It may be desirable that the total surface area of the return contact be great enough to reduce impedance to a point where current can be driven through the return contact without exceeding a maximum voltage. A return contact may comprise any suitable materials, such as but not limited to one or more conductive materials, such as metals (e.g., stainless steel, titanium, tantalum, platinum or platinum-iridium, other alloys thereof, or the like), conductive ceramics (e.g., titanium nitride), or hydrogels.

Figure 28A:
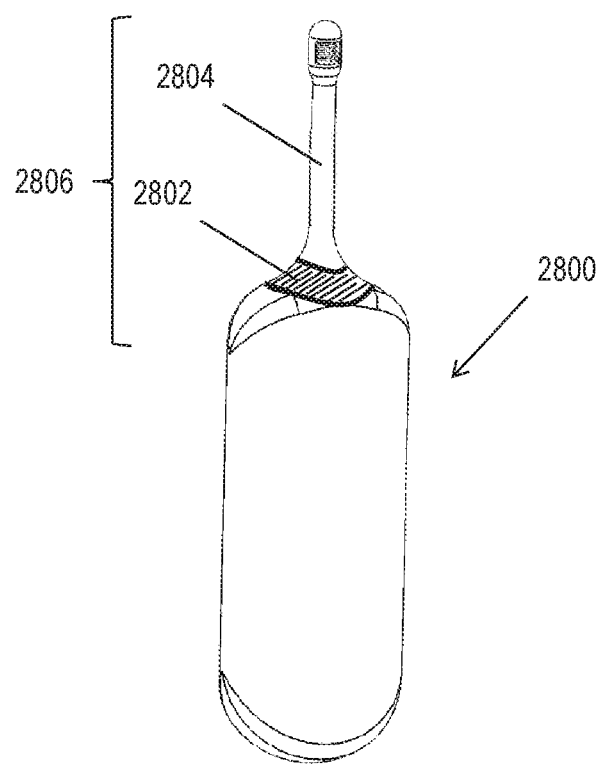
Figure 28B:
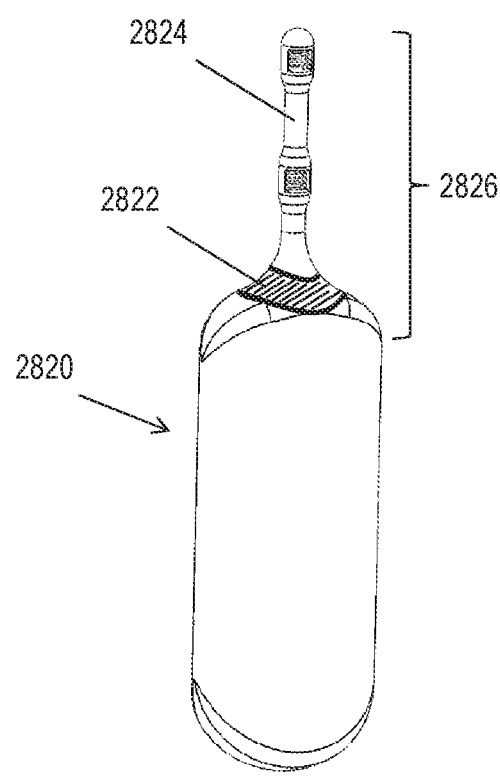

In other variations, a return contact may be located on the base member of a stimulator probe, near the base of a nasal insertion prong. For example, FIGS. 28A and 28B show nasal stimulators 2800 and 2820 each having return contacts 2802 and 2822 located on the stimulator probes 2806 and 2826, respectively, near the proximal end of the nasal insertion prongs 2804 and 2824. The return contacts 2802 and 2822 are shown as having an annular shape near the proximal end of the nasal insertion prongs, such that the return contacts are configured to contact an area of tissue near the opening of the nostril when the nasal insertion prong is inserted into a nasal cavity. By having a return contact located near the opening of the nostril, it may be possible to have current flow through a desired portion of the septum while having only a single nasal insertion prong (i.e., one or more electrodes on only one side of the septum, as opposed to at least one electrode on each side of the septum). It should be appreciated that in other variations, the return contacts may have other suitable shapes, such as a plurality of bands or contact points. As shown in FIGS. 28A-28B, handheld stimulators comprising return contacts located near a base of a nasal insertion prong may have any suitable number of electrodes located on the nasal insertion prong, such as one per prong (FIG. 28A), two (FIG. 28B), three, four, five, six, or more electrodes. It should be appreciated that although FIGS. 28A-28B show a return contact located near the proximal end of a nasal insertion prong of a stimulator comprising a single nasal insertion prong, return contacts may also be positioned near the proximal end of one or both nasal insertion prongs of a stimulator comprising two nasal insertion prongs.

Figures 29A, 29B:
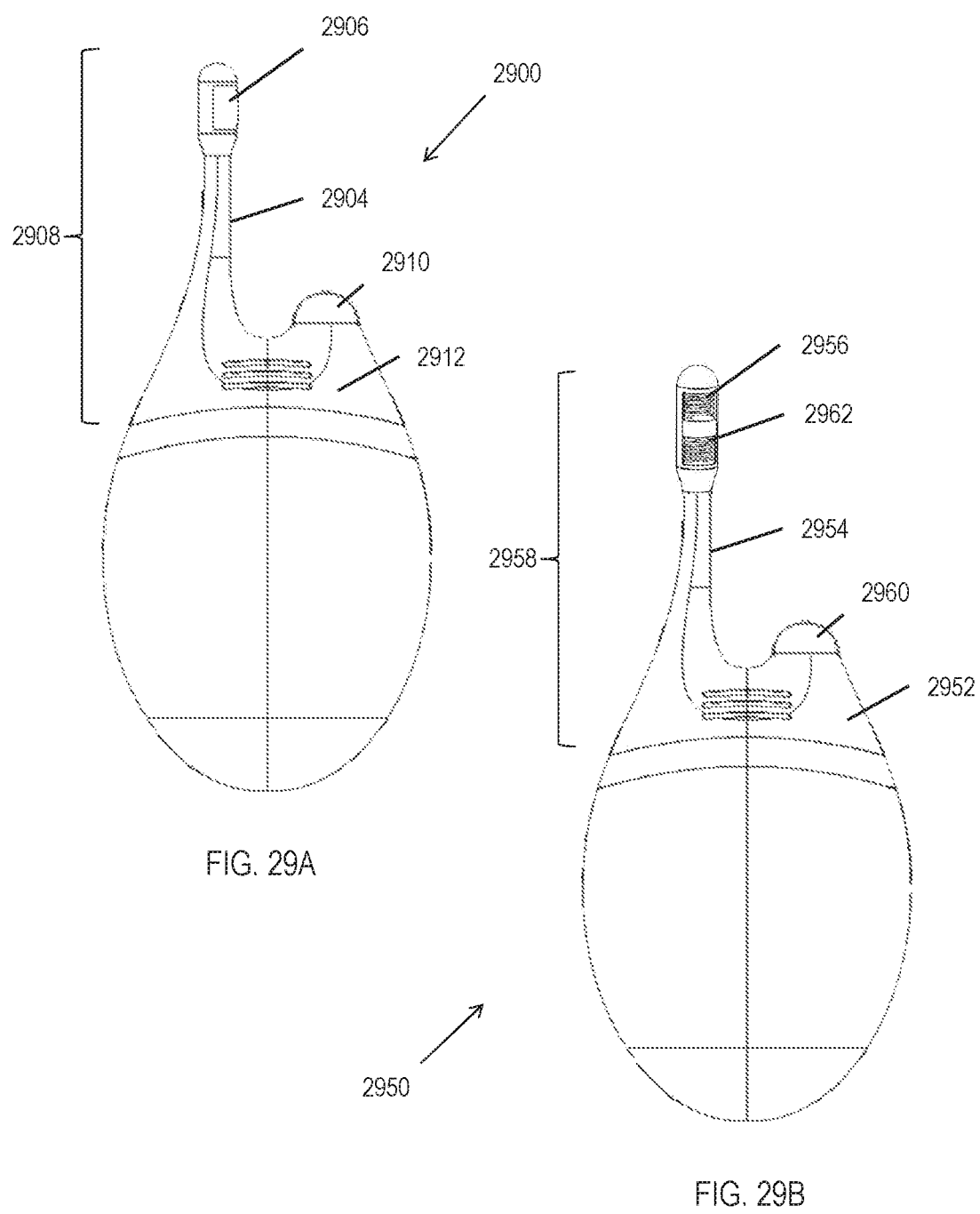

In yet other variations, a return contact may be located on the base member of a stimulator probe, away from the proximal end of a nasal insertion prong. For example, FIGS. 29A-29B show handheld stimulators comprising a single nasal insertion prong configured to be inserted into a first nostril, and a return contact configured to contact an area of tissue near the opening of a second nostril, against the skin and/or nasal mucosa. FIG. 29A depicts a handheld stimulator 2900 comprising a single stimulator probe 2908. The stimulator probe 2908 comprises a single nasal insertion prong 2904 having a single electrode 2906. The base member 2912 of the stimulator probe 2908 comprises a return contact 2910. The stimulator 2900 may be configured such that when the nasal insertion prong 2904 is inserted into a first nostril, the return contact 2910 is in contact with an area of tissue near the opening of a second nostril. FIG. 29B shows a similar handheld stimulator 2950 comprising a stimulator probe 2958 comprising a single nasal insertion prong 2954 comprising two electrodes 2956 and 2962, and a base member 2952 comprising a return contact 2960 configured to contact an area of tissue near the opening of a second nostril.

Figure 29C:
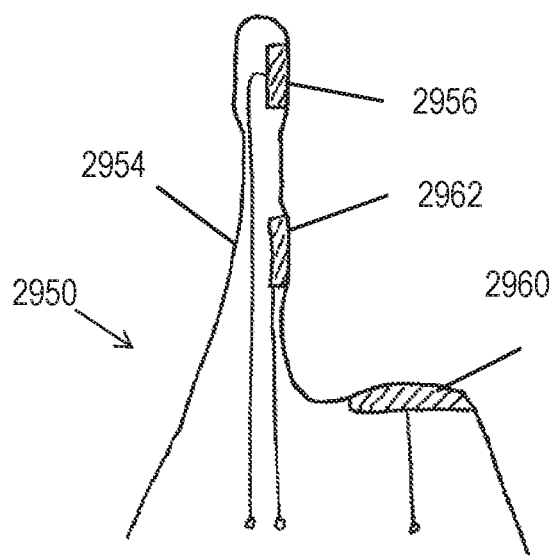
FIGS. 29C-29E show schematic illustrations of configurations of the handheld nasal stimulator of FIGS. 29A-29B.
Figure 29D:
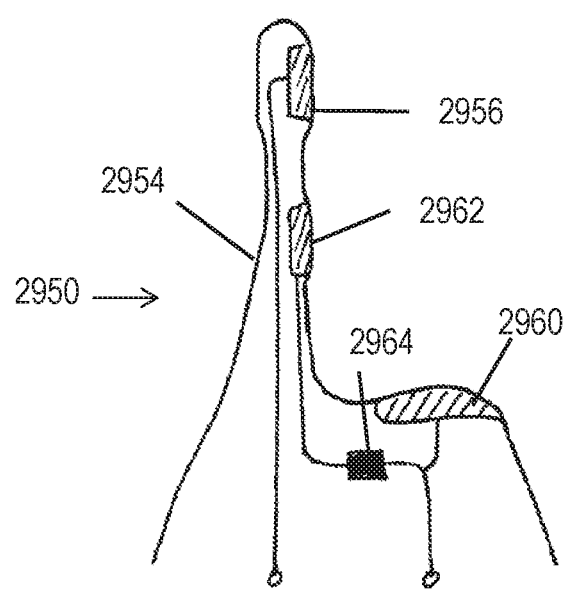
Figure 29E:
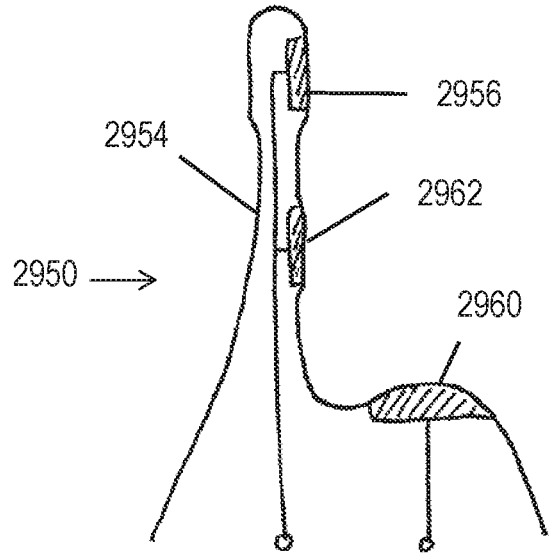

In the variation shown in FIG. 29B, the leads may have various arrangements, such that each electrode or return contact may be at a different potential, or two may be at the same potential. For example, the leads connected to each of the electrodes 2956, 2962, and the return contact 2960 may in some variations be separate, as schematically illustrated in FIG. 29C. In other variations, one of the two electrodes 2956, 2962 may have a common lead with the return contact 2960, as schematically illustrated in FIG. 29D, such that the electrode and the return contact are at the same potential. In yet other variations, the two electrodes 2956, 2962 may have a common lead, as shown in FIG. 29E. A resistor may optionally be located between an electrode and the return contact, or between the two electrodes, which may affect the distribution of current delivery. For example, FIG. 29C shows a resistor 2964 located between the electrode 2962 and the return contact 2960. These various arrangements may affect the spatial delivery of current, as described in more detail herein.

Spatial Control

The electrodes and return contacts described herein may allow stimulus delivery by the stimulators to be spatially controlled. That is, current steering may be achieved by driving current particular pathways between the electrodes or return contacts, and in some instances, the pathway(s) of current flow through tissue may change over time to achieve spatial patterning. The current being delivered by or to each electrode may in some instances be individually controlled in order to achieve these effects. For example, the same or different waveforms, or no waveform, may be delivered by each of the electrodes at any given time, and the stimulus delivery by each of the electrodes may vary over time. Current steering may allow both the current pathways and the quantity of current along each pathway to be controlled. Current steering may enable particular areas of tissue to be targeted by the stimuli, and spatial patterning may affect a subject's perception of the stimulus and may reduce accommodation. Spatial patterning may provide neural activation to varying tissue over time (e.g., to varying sets of nerve branches, such as of the anterior ethmoidal nerve within the nasal mucosa). In some instances, for example, this could be interpreted as similar to a physical movement of a system having a single fixed current pathway, thereby reducing the need for a user to move the electrode within the nose to activate varying sets of neural fibers.

In some variations, exemplary anatomical targets may include nerves, muscles, mucosal or sub-mucosal tissues (e.g., nasal or sinus mucosa or sub-mucosa), sensory cells in the glaborous and hairy skin, glands, or other structures of a patient involved in the process of lacrimation or glandular vasodilation that may be electrically stimulated. For example, the anatomical structures may include, but are not limited to, a lacrimal gland, one or more meibomian glands, lacrimal ducts, cutaneous receptors (mechanoreceptors, Meissner's corpuscles, neurotendinous spindles, golgi tendon organs, Ruffini's corpuscles, Stretch Receptors, Ruffini corpuscle end-organs, Pacinian corpuscle end-organs, hair follicle receptors, free nerve endings, thermoreceptors, bulboid or Krause corpuscles, nociceptors), parasympathetic nerves, fibers and neurites, sympathetic nerves, fibers and neurites, rami lacrimales, the lacrimal nerve, perivascular nerves of lacrimal artery and branches thereof, nerve fibers innervating the meibomian glands, myoepithelial cells of the lacrimal gland, acinar cells of the lacrimal gland, or ductal cells of the lacrimal gland. In yet a further variation, the anatomical structure is the infra-trochlear nerve. In other variations, the anatomical structure is a cutaneous receptor responsible for sensing changes in force or temperature over time or a set of cutaneous receptors in an area of the skin reporting changes in force applied to the skin directly or indirectly by moving hair growing in the skin, or the nerves innervating the cutaneous receptors reporting changes in force applied to the skin or hair in the skin, or temperature changes in the skin including the mucosa, the sub-mucosa in the nose, or the conjunctiva in the eye.

In some instances, it may be desirable to deliver the electrical stimuli described herein to one or more nerves that innervate the lacrimal gland tissue. In others, it may be desirable to deliver the electrical stimuli described herein to the nasal mucosa. This may cause lacrimation by activating the nasolacrimal reflex. In some instances, the targeted area may comprise tissue innervated by the anterior ethmoidal branch of the nasociliary nerve. In another variation, the anatomical structure is the posterior ethmoid nerve. In some instances, the targeted area of the nasal mucosa may be superior to the columella. It may in some instances be near the inferior end of the nasal bone (i.e., near the interface between the nasal bone and the upper lateral cartilage). As such, the stimulus may be delivered between about 20 mm and about 35 mm into the nasal cavity of the patient, in some cases via an electrode between about 25 mm and about 35 mm into the nasal cavity of the patient. In other instances, the targeted area may be the columella. It may be desirable that the stimulus be delivered in the anterior portion of the nasal cavity, within the nostrils and anterior to the turbinates, and in some instances, at a location anterior to the middle turbinate, or at a location anterior to the inferior turbinate. The stimulus may be delivered at least partially through tissue of or near the septum, and it may in some instances be desirable to direct stimulus such that a portion is directed toward the front of the nose. This may allow for selective activation of nerves in the front of the septum (e.g., the ophthalmic branch of the trigeminal nerve) while minimizing activation of nerves toward the rear of the nasal septum, which may reduce negative side effects that may occur from stimulation of nerves that innervate the teeth, and which may reduce rhinorrhea. It may also in some instances be desirable to direct the stimulus so as to reduce negative side effects that may occur from stimulation of the olfactory area.

One way to achieve stimulation of one or more of these target areas may be current steering. For example, current may be directed to flow in a pathway such that it is concentrated in areas where a target nerve (e.g., the anterior ethmoidal nerve) is located (e.g., certain portions of the septum) while avoiding stimulating areas that may cause discomfort or unnecessary unpleasant sensations (e.g., portions of the trigeminal nerve that innervate the teeth). By steering current in this way, preferential activation of particular nerves may be achieved with waveforms that might not otherwise be able to achieve preferential activation.

In handheld stimulation devices comprising one or more nasal insertion prongs, for example, current steering may be used to drive current between electrodes on the same prong and, additionally or alternatively, in devices comprising two nasal insertion prongs, between electrodes on different prongs. As described herein, handheld stimulation devices may also comprise one or more return contacts to provide additional possible current pathways. Spatial control may allow both the current pathways and the quantity of current along each pathway to be controlled, and may allow these to be changed over time. By controlling the current pathways, particular tissue areas can be targeted. In some variations, current steering may be used to adjust the location of stimulus delivery to a desired region of tissue without having to move an implanted or temporarily inserted stimulator.

In some cases, the current steering may be accomplished by having isolated circuits with separate current sources for each pathway, wherein each is floating without a common ground. In other cases, the current steering may be accomplished using a single current source based on the impedance values of multiple pathways. Current steering may also in some instances be carried out using a multiplexor, which may be located inside a waveform generator. In other instances it may be carried out using frequency selectivity, for example, by different electrodes being connected to receiver coils having different resonant frequencies, such that small changes in controller frequencies may allow for selective delivery of stimulus by the electrodes.

Figure 30A:
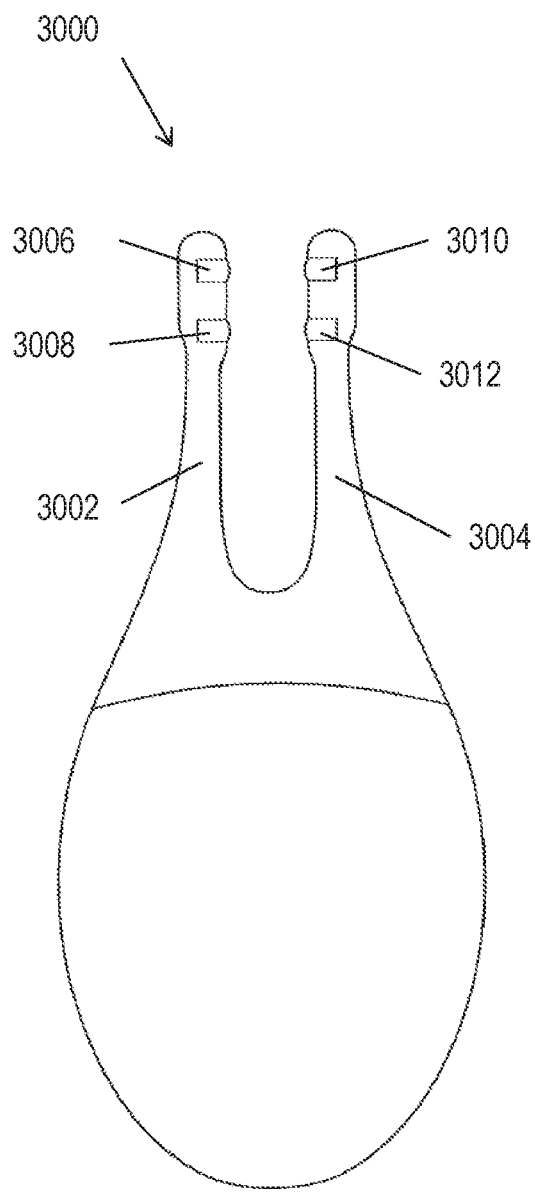
FIG. 30A depicts an exemplary handheld stimulator comprising two nasal insertion prongs.

As one example of spatial control, FIG. 30A depicts an illustrative stimulator 3000 comprising two nasal insertion prongs 3002 and 3004, each comprising two electrodes 3006, 3008 and 3010, 3012, respectively. Current steering may be used to drive current via various pathways between the four electrodes, including between the two nasal insertion prongs, between electrodes on the same nasal insertion prong, or both, which may result in stimulation of different anatomical targets.

Figure 30B:
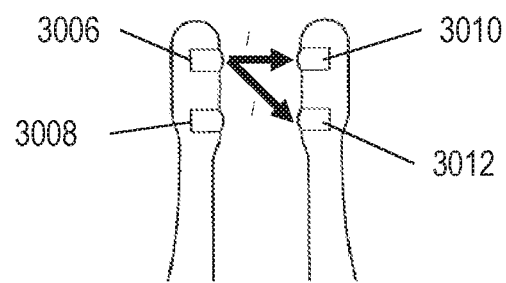
FIGS. 30B-30E depict variations of how current may be driven between the electrodes of the stimulator of FIG. 30A.
Figure 30C:
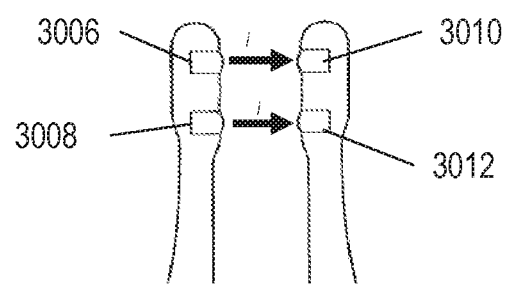
Figure 30D:
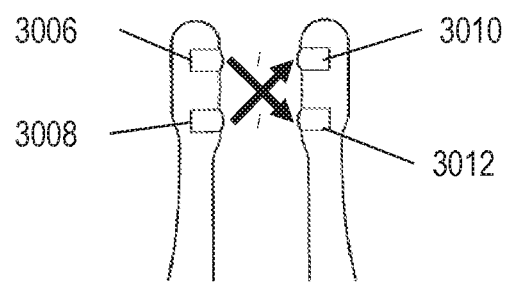
Figure 30E:
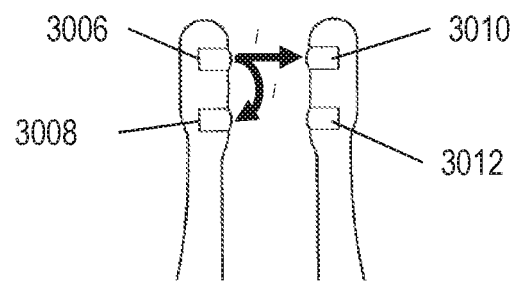

FIGS. 30B-30E show variations of how current may be directed between the electrodes. In some variations, the current may be directed to flow from one or more electrodes on prong 3002 to one or more electrodes on prong 3004. For example, in FIG. 30B, the current is delivered by electrode 3006, while electrode 3008 does not deliver any current. The current from electrode 3006 is steered toward electrodes 3010 and 3012, which function as return electrodes, such that a portion (e.g., 50%) of the current flows from electrode 3006 to electrode 3010, and a portion (e.g., 50%) of the current flows from electrode 3006 to electrode 3012. In FIG. 30C, current is also driven from one nasal insertion prong to the other, but in this configuration, electrodes 3006 and 3008 both deliver current, and electrodes 3010 and 3012 both act as return electrodes, such that a portion (e.g., 50%) of the total current flows from electrode 3006 to 3010, and a portion (e.g., 50%) of the total current flows from electrode 3008 to electrode 3012. In FIG. 30D, current is driven from one nasal insertion prong to the other, and electrodes 3006 and 3008 both deliver current, and electrodes 3010 and 3012 both act as return electrodes. However, in contrast to the example of FIG. 30C, a portion (e.g., 50%) of the total current flows from electrode 3006 to 3012, and a portion (e.g., 50%) of the total current flows from electrode 3008 to 3010. It should be appreciated that the current need not be divided evenly between pathways in these examples, and that more current may be directed through one of the two pathways.

Whereas in the examples of FIGS. 30B-30D the current is driven from an electrode on the first prong 3002 to an electrode on the second prong 3004, in other variations, the current may be directed between electrodes on the same prong. For example, in FIG. 30E, the current is delivered by electrode 3006, and electrode 3008 on the same prong and electrode 3010 on the other prong act as return electrodes. That is, a portion (e.g., 80%) of the current may travel from electrode 3006 on the first prong 3002 to electrode 3010 on the second prong 3004, while the remainder (e.g., 20%) may travel from electrode 3006 to electrode 3008, both located on the first prong 3002. In each arrangement illustrated in FIGS. 30B-30E, the described current steering may be accomplished, for example, by having isolated circuits with separate current sources for each pathway, where each is floating without a common ground. Each configuration of current steering in FIGS. 30B-30E may result in different anatomical targets near and within the septum being stimulated.

Current may also be steered between one or more electrodes located on a nasal insertion prong and one or more return contacts. Turning back to the handheld nasal stimulator of FIGS. 29A-29B, each of the electrical configurations of FIGS. 29C-29E may result in a different spatial configuration of current delivery, and thus the anatomical target stimulated. For example, FIG. 29C shows a resistor 2964 located between the electrode 2962 and the return contact 2960. In this configuration, if electrode 2956 delivers current, the presence of the resistor 2964 results in less current being driven from the electrode 2956 to electrode 2962 and more current being driven from the electrode 2956 to the return contact 2960, as compared to a configuration without the resistor 2964. As a result, when the nasal insertion prong 2954 is inserted into a nostril, such that the electrodes 2956 and 2962 are in contact with the nasal mucosa, more current may be driven through the septum, as compared to a configuration without the resistor 2964. In some variations, the resistor may be variable. It may be controllable by a use, such that the user can adjust the stimulation effect.

Figure 31:
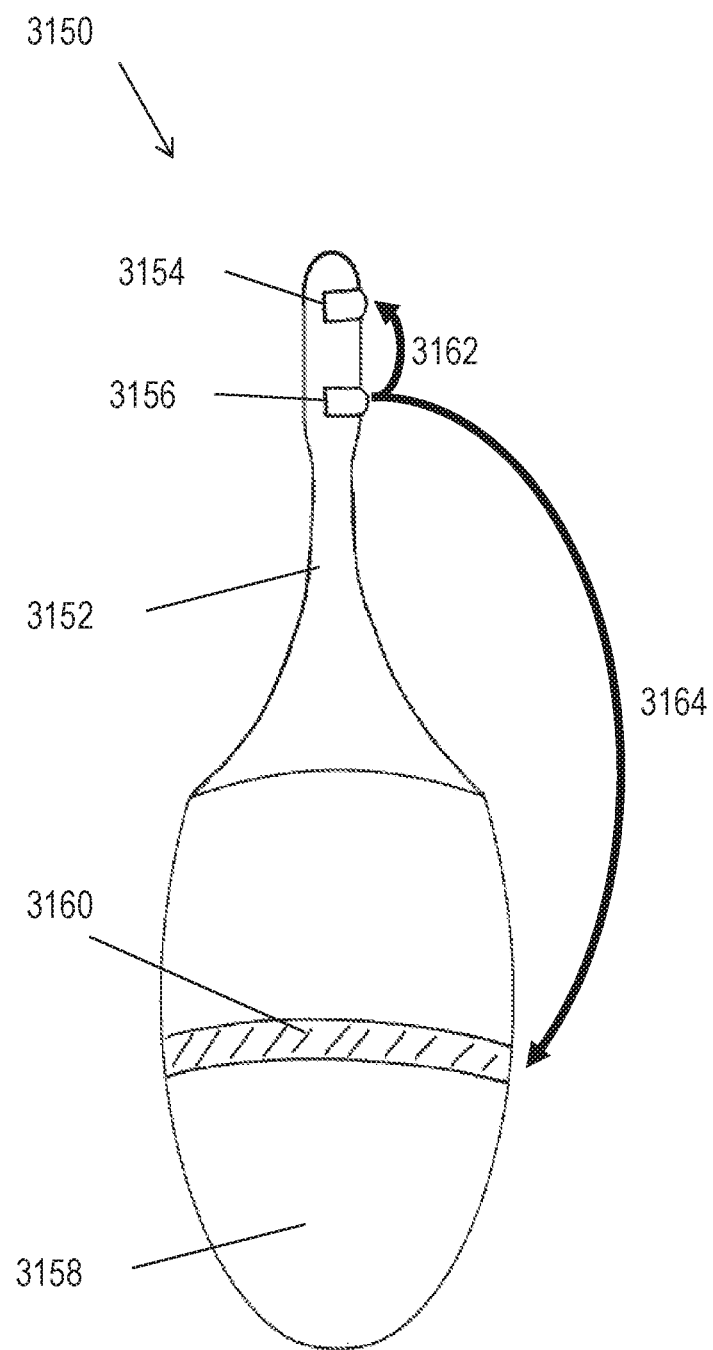
FIG. 31 depicts how current may be driven between electrodes and a return contact of an exemplary handheld stimulator having a single nasal insertion prong.

As another example, FIG. 31 illustrates current steering via multiple pathways using a handheld stimulator 3150 comprising a nasal insertion prong 3152 comprising first and second electrodes 3154 and 3156, as well as a return contact 3160 configured to be in contact with a user's hand while the first and second electrodes are in contact with a user's nasal mucosa. As illustrated, the current may be steered such that a portion (e.g., 70%) travels from electrode 3156 to electrode 3154 on the nasal insertion prong 3152, illustrated by the arrow 3162, while a portion (e.g., 30%) travels from electrode 3156 to the return contact 3160 on the stimulator body 3158, illustrated by the arrow 3164. As a result, there may be a higher current density, and thereby a higher voltage drop, across the area of a target nerve (e.g., the anterior ethmoidal nerve), while a lower current density would pass through other areas. It should be appreciated that arrows 3162, 3164, and the other arrows representing current pathways herein, are not intended to illustrate the exact physical path of current through tissue, but rather the origin and return of current with respect to the device. The actual path of the current through the tissue as it travels from the origin to the return will depend on the tissue shape and properties.

The paths through which current is steered may be changed over time to spatially pattern the stimulus delivery. That is, for example, during a first time period the current may be driven via a first set of pathway(s), and during a second time period the current may be driven via a second set of pathway(s). This may generate the sensation of a moving stimulus, which may reduce patient accommodation to the stimulus. For example, the handheld nasal stimulator 3000 may be configured to cycle, either in a predetermined fashion, randomly, or under user control, through the current steering patterns shown in FIGS. 30B-30E.

Figure 32A:
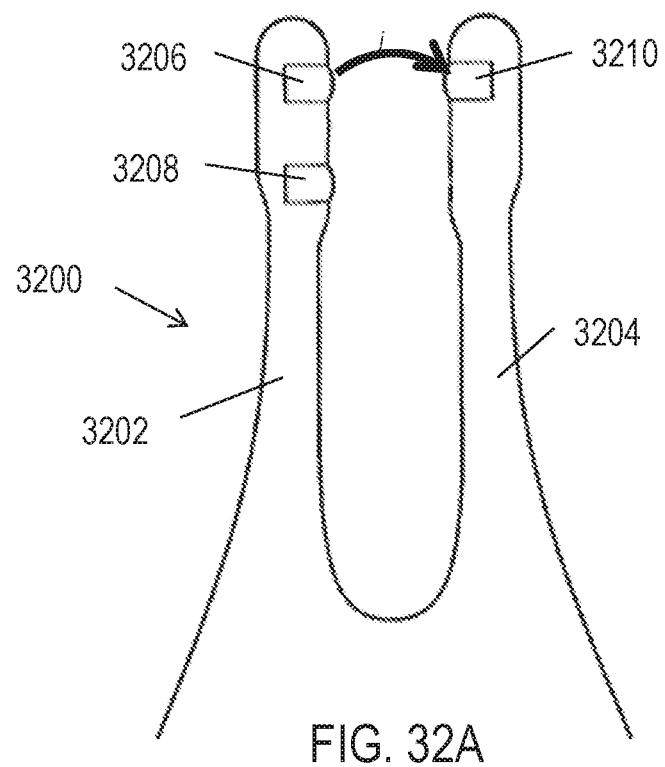
FIGS. 32A-32B illustrate how current may be driven between electrodes of an exemplary handheld stimulator having two nasal insertion prongs.
Figure 32B:
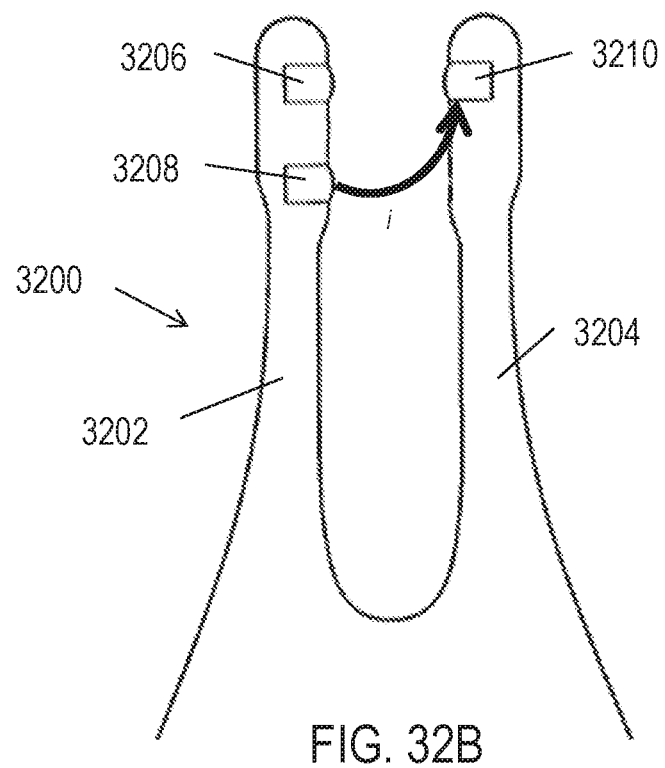
Figure 32C:
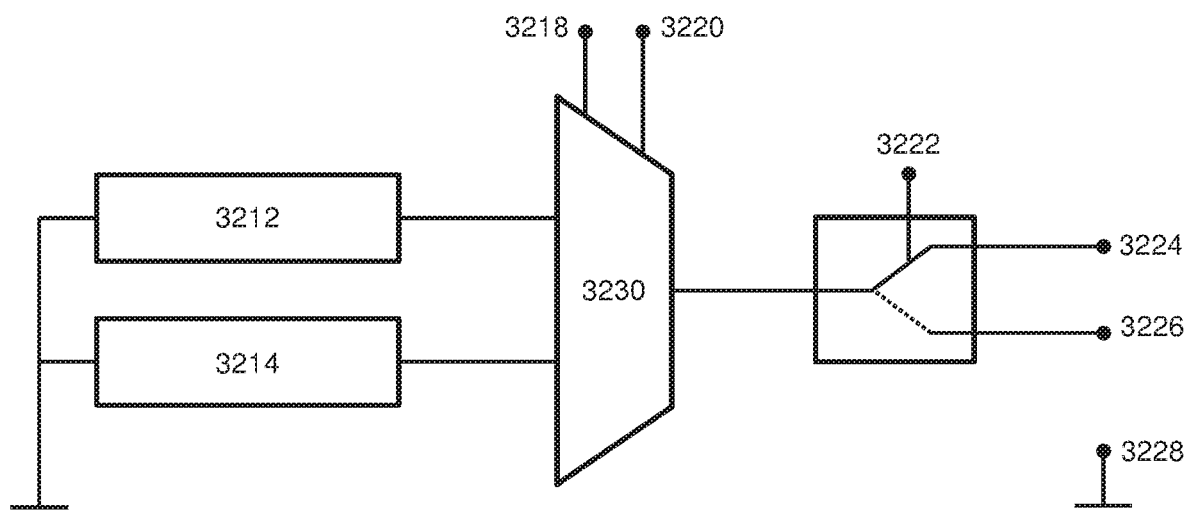
FIG. 32C shows a schematic illustration of a portion of the circuitry of the stimulator of FIGS. 32A-32B.
Figure 32D:
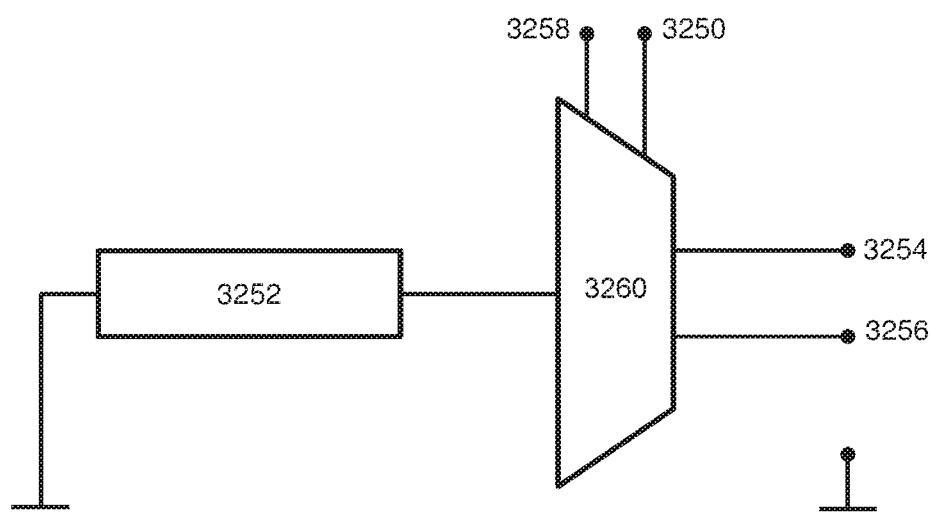
FIG. 32D shows a schematic illustration of a portion of an alternative configuration of circuitry for the stimulator of FIGS. 32A-32B.

As another example, FIGS. 32A-32B show a stimulator 3200 comprising a first nasal insertion prong 3202 and a second nasal insertion prong 3204. The first nasal insertion prong 3202 comprises a first electrode 3206 and a second electrode 3208, while the second nasal insertion prong 3204 comprises a single electrode 3210. The stimulator 3200 may have a first configuration (illustrated in FIG. 32A) in which current flows from electrode 3206 on the first nasal insertion prong 3202 to electrode 3210 on the second nasal insertion prong 3204, and a second configuration (illustrated in FIG. 32B) in which the current flows from electrode 3208 on the first nasal insertion prong 3202 to electrode 3210 on the second nasal insertion prong 3204. In order to switch between the first and second configurations, the stimulator 3200 may comprise a switch 3222, schematically illustrated in FIG. 32C, allowing selection of output 3224, which results in current delivery from electrode 3206, or selection of output 3226, which results in current delivery from electrode 3208. The variation shown in FIG. 32C also shows two signal generators 3212 and 3214, discussed in more detail below, but it should be appreciated the stimulator may comprise fewer or more signal generators. For example, FIG. 32D shows a schematic illustration of a portion of an alternative configuration of circuitry for the stimulator comprising a single signal generator 3252, the output from which can be directed via selector switches 3258 and 3250 of multiplexor 3260 to first output 3254 or second output 3256. Output 3254 may go to a first electrode (e.g., electrode 3206), and output 3256 may go to a second electrode (e.g., electrode 3208).

By switching between current delivery to be from different electrodes, the current pathway may be changed over time, which may allow stimulation of different tissue areas over time. This may in turn reduce accommodation and/or may allow particular anatomical areas to be targeted. In some instances, it may be desirable to temporarily target particular areas. For example, periodic partial activation of CN-V2 may reduce the sensation of needing to sneeze that may otherwise be perceived during stimulation of the anterior ethmoidal nerve.

Figure 33:
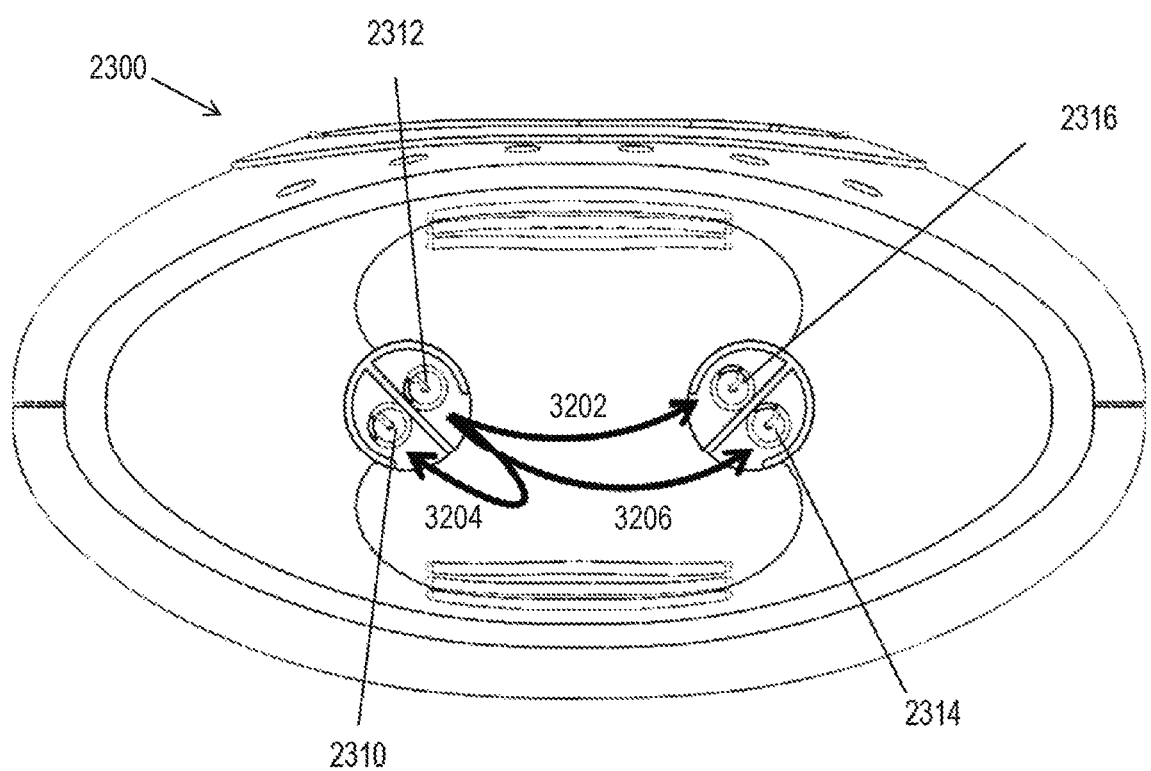
FIG. 33 shows a cut-away view of the stimulator of FIGS. 23A-23B with depictions of how current may be directed between the electrodes.

Similarly, FIG. 33 shows a cut-away view of the stimulator 2300 of FIGS. 23A-23B. As shown in FIG. 33, the stimulator 2300 can be configured such that current may be steered via various pathways. For example, current flowing from electrode 2312 on the first nasal insertion prong may be driven to electrode 2316 on the second nasal insertion prong via pathway 3202; to electrode 2314 on the second nasal insertion prong via pathway 3206; or to electrode 2310 on the first nasal insertion prong via pathway 3204.

In some variations, the current may be steered sequentially via the various pathways. This type of spatial patterning may be achieved in stimulators comprising a single current source used to drive two or more electrodes versus a common ground. This may be implemented using, for example, a multiplexor. The current may also be steered simultaneously via the various pathways. This type of current steering may be achieved in stimulators comprising a plurality of independent, or electrically floating, current sources. In these variations, a multiplexor may also be used to control which electrodes receive current from each source.

While the figures discussed above show the application of current steering to a handheld nasal stimulator, it should be appreciated that current steering may be applied with use of other devices, such as implantable stimulators (e.g., stimulators implanted in ocular or nasal regions) described herein. The ability to target particular areas of tissue without moving the electrode contact points may be particularly useful in the case of implantable stimulators having a fixed position relative to tissue.

When stimulators are configured for spatial patterning of stimulus delivery, the spatial patterning may have any suitable parameters. For example, current delivery may be switched between two or more pathways at a predetermined frequency, such as about every 0.5 seconds, 1 second, 2 seconds, 5 seconds, 10 seconds, or longer. In other variations, a user may be able to switch between two or more pathways using a user interface, such as a user interface described herein. In yet other variations, the pathway may be selected by a clinician for an individual patient. For example, when the stimulator is an implantable stimulator, a clinician may be able to select a pathway after implantation, so that the stimulated tissue can be tailored after implantation without having to adjust the implantation site.

Waveforms

The electrical stimulation waveforms delivered by the stimulators described herein may be tailored for specific treatment regimens and/or specific patients. In variations of stimulators configured to deliver current via two or more pathways, different waveforms may be delivered via each pathway, and the waveform delivered via each pathway may be changed over time. Returning to FIG. 32C, a stimulator may comprise a first signal generator 3212 configured to generate a first waveform, and a second signal generator 3214 configured to generate a second waveform. A multiplexer 3230 may have corresponding first and second select lines 3218 and 3220. In combination with the switch 3222, described above, the multiplexer 3230 may allow for the waveform from either signal generator to be delivered to either electrode of the nasal insertion prong 3202, or to the return 3228. While FIG. 32C shows only two signal generators and two outputs, it should be appreciated that a similar configuration may be used for any number of signal generators and outputs. The waveform generated by each signal generator may have any suitable parameters, and may be any of the waveforms described in more detail herein.

As is described in more detail herein, when temporal patterning of electrical stimulation waveforms is employed, waveform parameters such as the shape, the frequency, the amplitude, and the pulse width may be modulated. The frequency, pulse-width, and/or amplitude of the waveform may be modulated linearly, exponentially, as a sawtooth, a sinusoidal form, etc., or they may be modulated randomly. The stimulation can also be interrupted as part of the temporal patterning. That is, the stimulation can be in an on/off condition, e.g., for durations of 1 second on/1 second off, 5 seconds on/5 seconds off, etc. Modulation of the waveform shape (e.g., rectangular vs. triangular vs. exponential) in a rhythmic or non-deterministic, non-rhythmic fashion may also be used. Thus, numerous variations in temporal waveform patterning can be achieved. It should be understood that combinations of these parameter changes over time in a repetitive manner may also be considered temporal patterning. In some instances, random temporal patterning may be employed. Temporal patterning may help to prevent patient habituation to the applied stimulation (i.e., may help to prevent the patient response to the stimulation decreasing during stimulation).

In some instances, it may be desirable to configure the stimulation waveform to minimize side effects. In some instances, it may be desirable to promote stimulation of larger-diameter nerves (e.g., afferent fibers of the trigeminal nerve), which may promote a therapeutic effect, while reducing the stimulation of smaller nerves (e.g., a-delta fibers, c fibers, sympathetic and parasympathetic fibers), which may result in pain, discomfort, or mucus production. Generally, for smaller pulse-widths, the activation threshold for larger-diameter nerves may be lower than the activation threshold for the smaller nerve fibers. Conversely, for larger pulse-widths, the activation threshold for larger-diameter nerves may be higher than the activation threshold for the smaller nerve fibers. Accordingly, in some instances, it may be desirable to select a pulse width that preferably actuates the larger-diameter nerves. In some variations, the pulse width may be between 50 µs and about 1200 µs. As another example, certain waveforms may minimize activation of the branches of the trigeminal nerve (e.g., CN V2) that travel to the teeth. These may include waveforms ranging from 30 µs to 300 µs in pulse width, 10 Hz to 150 Hz in frequency, and 0.1 mA to 5 mA in amplitude.

The stimulation may be delivered periodically at regular or irregular intervals. Stimulation bursts may be delivered periodically at regular or irregular intervals. The stimulation amplitude, pulse width, or frequency may be modified during the course of stimulation. For example, the stimulation amplitude may be ramped from a low amplitude to a higher amplitude over a period of time. In other variations, the stimulation amplitude may be ramped from a high amplitude to a lower amplitude over a period of time. The stimulation pulse width may also be ramped from a low pulse width to a higher pulse width over a period of time. The stimulation pulse width may be ramped from a high pulse width to a lower pulse width over a period of time. The ramp period may be between 1 second and 15 minutes. Alternatively, the ramp period may be between 5 seconds and 30 seconds.

The temporally patterned stimulation waveforms described herein may be used to increase the comfort of the patient and/or may be used to improve the efficacy of the stimulation, and thus, described below are waveform parameters that may be used alone or in combination to increase comfort and/or efficacy.

It should be appreciated that the waveforms described here may be delivered via a multi-polar, such as bipolar, tripolar, quad-polar, or higher-polar configuration or a monopolar configuration with distal return. The waveforms may be a sinusoidal, quasi-sinusoidal, square-wave, sawtooth, ramped, or triangular waveforms, truncated-versions thereof (e.g., where the waveform plateaus when a certain amplitude is reached), or the like, as described in more detail herein.

Shape

In some instances, the waveform shape or modulation thereof may affect the comfort and/or efficacy of the stimulation. When the stimulator (electrode device) is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). Each phase of the biphasic pulse may be either voltage-controlled or current-controlled. In some variations, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa. In some instances, a combination of current-controlled bilateral stimulation and voltage-controlled charge balancing may allow for unilateral stimulation, and by modifying the waveform shape, may allow for switching between areas of stimulation, e.g., between nostrils when electrodes are located in each nostril, as described herein.

In some variations in which the waveform comprises a biphasic pulse, it may be desirable to configure the biphasic pulse to be charge-balanced, so that the net charge delivered by the biphasic pulse is approximately zero. In some variations, a biphasic pulse may be symmetric, such that the first phase and the charge-balancing phase have the same pulse width and amplitude. Having a symmetric biphasic pulse may allow the same type of stimulus to be delivered, e.g., to each nasal cavity. The pulses of a first phase may stimulate a first side of the nose (while providing a charge-balancing phase to a second side of the nose), while the pulses of the opposite phase may stimulate the second side of the nose (while providing a charge-balancing phase to the first side of the nose).

In other variations in which the waveform comprises a biphasic pulse, a biphasic pulse may be asymmetric, where the amplitude and/or pulse width of the first pulse may differ from that of the charge-balancing phase. Even if the biphasic pulse is asymmetric, the biphasic pulse may be charge-balanced. For example, the cathodic pulse may have lower amplitude but longer duration than the anodic pulse, or the cathodic pulse may have higher amplitude but shorter duration than the anodic pulse. In both instances, the charge injection (amplitude times duration) may be equal for each pulse, such that the net charge delivered by the biphasic pulse is approximately zero.

The shape of the waveform may be changed to preferentially activate the tissue near an electrode. For example, FIGS. 5A-5C illustrate exemplary waveforms configured to preferentially activate tissue near one of two electrodes, and where the preferential activation may move from near one electrode to the other over time. In variations in which the stimulator is a handheld stimulator configured to have an electrode in each nostril, for example, this preferential activation may allow for preferential activation of tissue in one of the two nostrils, which may change over time. For example, FIG. 5A shows a variation of a biphasic charge-balanced waveform 518 in which the aspect ratios (amplitude:duration) of the pulses changes over time. Shown there is a waveform that has a first pattern wherein a leading cathodic pulse has a greater amplitude and shorter duration in comparison to the following anodic pulse. This pattern is found in the time periods indicated by 510 and 514. The waveform has a second pattern where the leading cathodic pulse has a lesser amplitude and longer duration in comparison to the following anodic pulse. This pattern is found in the time periods indicated by 512 and 516. It should be appreciated that each time period may have any suitable duration and thus comprise any suitable number of pulses. As one example, each time period may last for about 1 second. In other examples, each time period may last for less than 1 second, about 1 to about 5 seconds, about 5 to about 10 seconds, about 10 to about 20 seconds, or longer.

In some variations the waveform may transition between two aspect ratios in an abrupt fashion. In other variations the transition may be gradual, where the aspect ratio of the cathodic pulse may increase over time and then decrease over time, while the aspect ratio of the anodic pulse may decrease over time and then increase over time. FIG. 5B shows an example of a waveform 520 that gradually transitions between aspect ratios. These increases and decreases may have any suitable form, such as linear increases and decreases or sinusoidal increases and decreases. In other variations, the transition may have a sawtooth shape, in which the aspect ratio of the cathodic pulse increases gradually over time while the aspect ratio of the anodic pulse decreases gradually over time, and then the aspect ratio of the cathodic pulse decreases abruptly while the aspect ratio of the anodic pulse increases abruptly.

In some variations, the polarity is switched back and forth between a pattern in which the cathodic pulse is first and a pattern in which the anodic pulse is first. For example, FIG. 5C shows an illustrative version of such a stimulation waveform 522. As shown there, the time periods indicated by 502 and 506 may have a cathodic pulse and then an anodic pulse, while the time periods indicated by 504 and 508 may have an anodic pulse and then a cathodic pulse. It should be appreciated that each time period may have any suitable duration. As one example, each time period may last for about 1 second. In other examples, each time period may last for less than 1 second, about 1-5 seconds, about 5-10 seconds, about 10-20 seconds, or longer. In some variations, each time period may last for a single pair of pulses, such that the stimulation waveform comprises a repeating pattern of two anodic pulses and two cathodic pulses.

Although the patterns having variable amplitude:duration aspect ratios may have uniform charge injection, they may preferentially activate the tissue near one of the two electrodes. That is, when the leading cathodic pulse has a greater amplitude and shorter duration than the anodic pulse, the waveform may preferentially activate tissue near a cathodic electrode; when the leading cathodic pulse has a lesser amplitude and longer duration than the anodic pulse, the waveform may preferentially activate tissue near an anodic electrode. Changing aspect ratios and switching polarities as described herein may increase the lacrimation response and/or change tear composition resulting from stimulation. This may be because switching polarities leads to non-linear addition of the stimuli as perceived by the central nervous system, as well as because switching polarities may reduce a patient's accommodation to the stimuli. Additionally, some stimulators described herein may be configured such that a user may be able to change the aspect ratios of a biphasic waveform in order to change the location or extent of preferential activation, such as by using a user interface. For some patients, adjusting the aspect ratio may result in a perception of a more symmetrical waveform and/or result in a more symmetrically bilateral treatment effect. In some instances, it may be desirable to have an asymmetrical bilateral treatment effect, or a unilateral treatment effect, for example in a patient having more severe dry eye in one eye than the other. In these instances, a patient may use a user interface to adjust the aspect ratio to achieve the desired asymmetrical effect.

Frequency

In order to treat dry eye or otherwise produce a tearing response by stimulating tissue, the stimulators described herein may be configured to generate one of more waveforms at frequencies suitable for stimulating targeted tissue (e.g., a nerve). The frequency may affect the comfort and/or efficacy of the stimulation. Generally, the frequency is preferably between about 0.1 Hz and about 200 Hz. In some of these variations, the frequency is preferably between about 10 Hz and about 200 Hz. In some of these variations, the frequency is preferably between about 30 Hz and about 150 Hz. In others of these variations, the frequency is preferably between about 50 Hz and about 80 Hz. In others of these variations, the frequency is preferably between about 30 Hz and about 60 Hz. In some variations, the frequency may be about 1.5 Hz, about 10.25 Hz, about 70 Hz, about 150 Hz, about 25 Hz, about 27.5 Hz, about 30 Hz, about 32.5 Hz, about 35 Hz, about 37.5 Hz, about 40 Hz, about 42.5 Hz, about 45 Hz, about 47.5 Hz, about 50 Hz, about 52.5 Hz, about 55 Hz, about 57.5 Hz, about 60 Hz, about 62.5 Hz, or about 65 Hz. In some variations, high frequencies, such as those between about 145 Hz and about 155 Hz may be too high for each pulse to stimulate/activate the target tissues. As a result, the stimulation may be interpreted by the patient to have an element of randomness, which in turn may help to reduce patient habituation. The frequencies described herein may be suitable for stimulating the targeted tissue to initiate a reflex circuit that activates the lacrimal gland to produce tears, and/or suitable for directly driving efferent fibers innervating the lacrimal gland. In some instances, the frequency may be chosen for preferential activation of certain anatomical targets, as described herein.

Amplitude

In order to treat dry eye or otherwise produce a tearing response by stimulating tissue, the stimulators described herein may be configured to deliver a current suitable for stimulating targeted tissue (e.g., a nerve). The maximum amplitude or modulation thereof may affect the comfort and/or efficacy of the stimulation. When the stimulus comprises a biphasic pulse and the first phase of the biphasic pulse is current-controlled, the first phase may preferably have an amplitude between about 1.0 mA and about 10 mA. Amplitudes within these ranges may be high enough to stimulate targeted tissue, but sufficiently low as to avoid any significant heating of tissue, ablation of tissue, or the like. In some variations the amplitude may be between about 1.0 mA and about 5.0 mA. In other variations, the first phase may have an amplitude of about 0.1 mA, about 0.2 mA, about 0.3 mA, about 0.4 mA, about 0.5 mA, about 0.6 mA, about 0.7 mA, about 0.8 mA, about 0.9 mA, or about 1.0 mA. In some variations, the amplitude may be variable. For example, the amplitude may vary between about 1.3 mA and about 1.5 mA, about 2.2 mA and about 2.5 mA, about 3.2 mA and about 3.7 mA, about 4.3 mA and about 5.0 mA. When the first phase of a biphasic pulse is voltage-controlled, the first phase may preferably have an amplitude between about 10 mV and about 100 V.

Figure 6A:
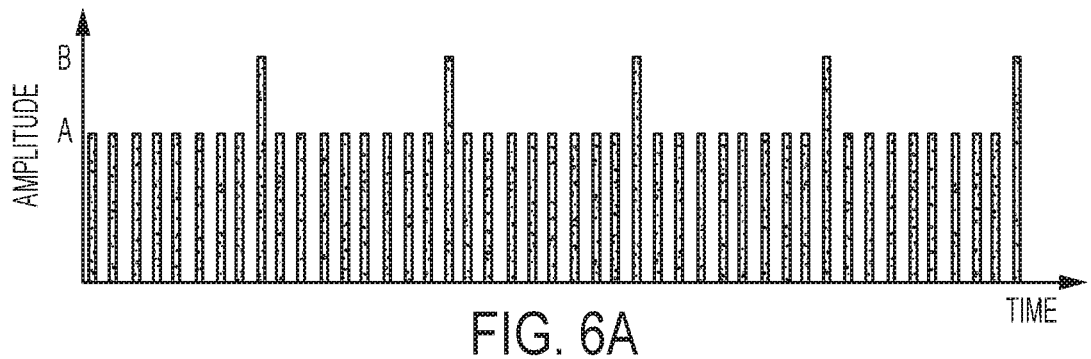
FIGS. 6A-6D illustrate exemplary amplitude variations over time.
Figure 6B:
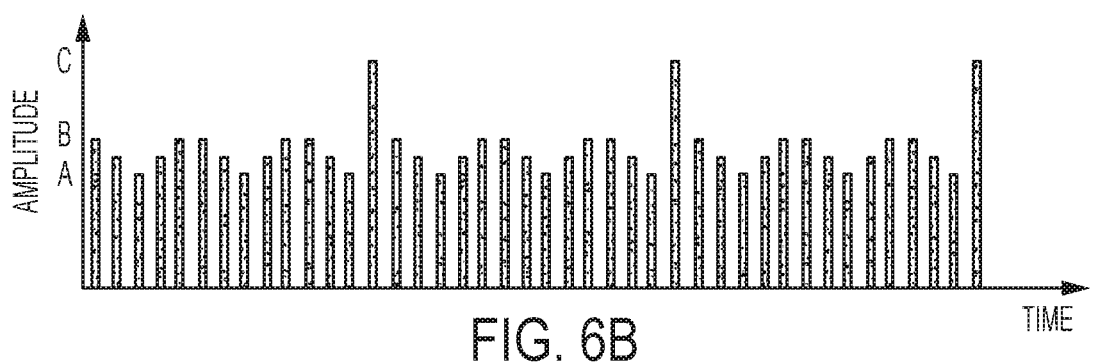
Figure 6C:
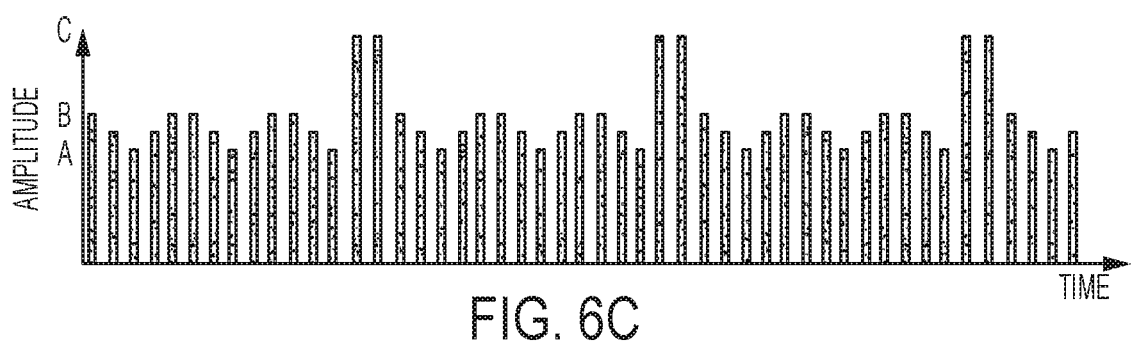
Figure 6D:
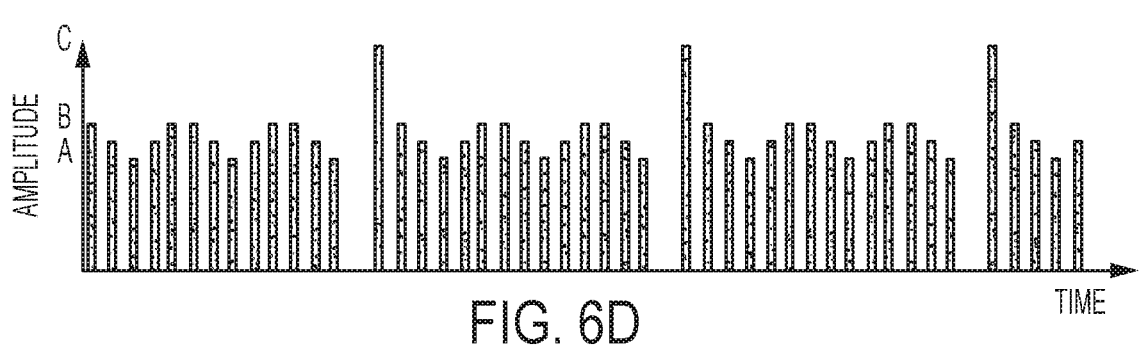

When a stimulator is configured to deliver a pulse-based waveform, in some variations, the amplitude of the pulses may be constant over time. In other variations, the amplitude of the pulses may vary over time. This may reduce patient accommodation. In some variations, the amplitude of pulses may increase (linearly, exponentially, etc.) from a minimum value to a maximum value, drop to the minimum value, and repeat as necessary. In some variations, the amplitude of the pulses may vary according to a sinusoidal profile. In another variation, as illustrated in FIG. 6A, the amplitude may periodically increase from a baseline amplitude (A) to a higher amplitude (B) for a single pulse. In yet another variation, as illustrated in FIGS. 6B-6C, the amplitude of the pulses may follow a periodically increasing and decreasing pattern between two lower amplitudes (A, B), and periodically increase to a higher amplitude (C) for a single pulse (FIG. 6B) or for a plurality of pulses (e.g., two pulses) (FIG. 6C). In yet another variation, as illustrated in FIG. 6D, a higher amplitude pulse (or pulses) may be preceded by a brief pause (i.e., no current delivery). Each of these types of amplitude modulation may be implemented alone or in combination with any other type of amplitude modulation, and may reduce patient accommodation.

In some variations in which the amplitude varies over time, the amplitude may vary at a frequency suitable for reducing patient accommodation or increasing patient comfort such as between about 0.1 Hz and about 5 Hz, between about 1 Hz and about 5 Hz, between about 1 Hz and 2 Hz, between about 2 Hz and 3Hz, between about 3 Hz and 4 Hz, or about 4 Hz and about 5 Hz. In some variation, the amplitude may vary at a frequency of about 1.0 Hz, about 1.1 Hz, about 1.2 Hz, about 1.3 Hz, about 1.4 Hz, about 1.5 Hz, about 1.6 Hz, about 1.7 Hz, about 1.8 Hz, about 1.9 Hz, about 2.0 Hz, about 2.1 Hz, about 2.2 Hz, about 2.3 Hz, about 2.4 Hz, about 2.5 Hz, about 2.6 Hz, about 2.7 Hz, about 2.8 Hz, about 2.9 Hz, about 3.0 Hz, about 3.1 Hz, about 3.2 Hz, about 3.3 Hz about 3.4 Hz, about 3.5 Hz, about 3.6 Hz, about 3.7 Hz, about 3.8 Hz, about 3.9 Hz, or about 4.0 Hz. In other variations, the stimulation waveform may be a modulated high frequency signal (e.g., sinusoidal), which may be modulated at a beat frequency of the ranges described above. In such variations, the carrier frequency may be between about 100 Hz and about 100 kHz.

Pulse Width

In order to treat dry eye or otherwise produce a tearing response by stimulating tissue, the stimulators described herein may be configured to deliver a waveform in which the first phase may preferably have a pulse width between about 1 μs and about 10 ms. In some of these variations, the pulse width may be between about 10 μs and about 100 μs. In other variations, the pulse width may be between about 100 μs and about 1 ms. In yet other variations, the pulse width may be between about 0 μs and about 300 μs. In yet other variations, the pulse width may be between about 0 μs and 500μs. As described above, it may be desirable to select a pulse width that preferably actuates larger-diameter nerves. In some variations, the pulse width may be between 50 μs and about 1200 μs. As another example, pulse widths of 30 μs to 300 μs may minimize activation of the branches of the trigeminal nerve (e.g., CN V2) that travel to the teeth.

Figure 7A:
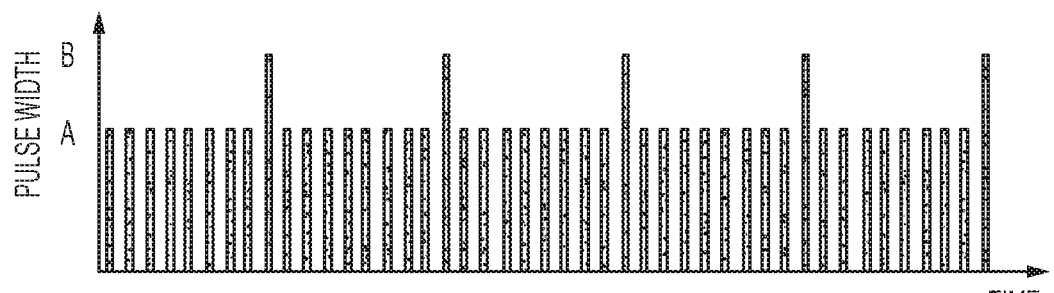
FIGS. 7A-7D illustrate exemplary pulse width variations over time.
Figure 7B:
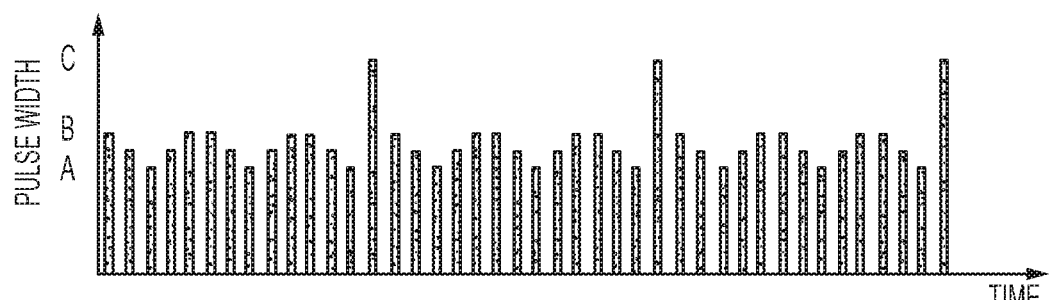
Figure 7C:
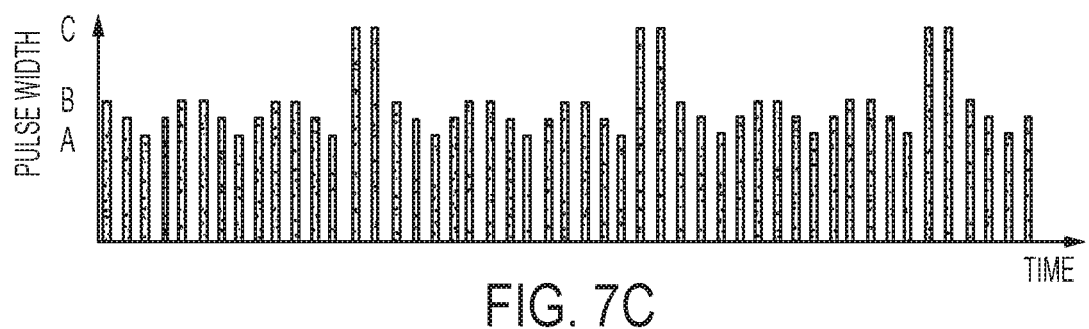
Figure 7D:
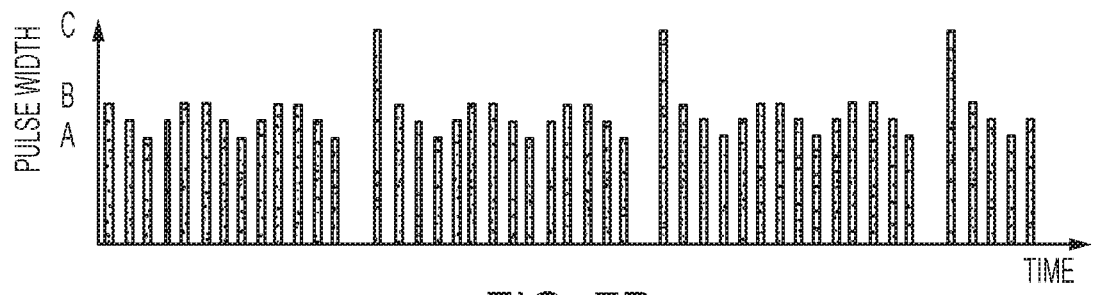

In some variations, the pulse width may be constant over time. In other variations, the pulse width may vary over time. Pulse width modulation over time may increase the efficacy and/or comfort of the stimulation. In some variations, the pulse width may increase (linearly, exponentially, etc.) from a minimum value to a maximum value, drop to the minimum value, and repeat as necessary. In some variations, the pulse width may vary according to a sinusoidal profile. In another variation, as illustrated in FIG. 7A, the pulse width may periodically increase from a baseline pulse width (A) to a longer pulse width (B) for a single pulse. In yet another variation, as illustrated in FIGS. 7B-7C, the pulse width may follow a periodically increasing and decreasing pattern between two shorter pulse widths (A, B), and periodically lengthen to a longer pulse width (C) for a single pulse (FIG. 7B) or for a plurality of pulses (e.g., two pulses) (FIG. 7C). In yet another variation, as illustrated in FIG. 7D, a longer pulse width pulse (or pulses) may be preceded by a brief pause (i.e., no current delivery). Each of these types of pulse width modulation may be implemented alone or in combination with any other type of pulse width modulation. In any form of pulse width modulation, the pulse width may vary at any suitable frequency. In some variations the pulse width may vary at about 0.1 Hz, about 0.2 Hz, about 0.3 Hz, about 0.4 Hz, about 0.5 Hz, about 0.6 Hz, about 0.7 Hz, about 0.8 Hz, about 0.9 Hz, about 1 Hz, about 1.1 Hz, about 1.2 Hz, about 1.3 Hz, about 1.4 Hz, or about 1.5 Hz. In some variations, modulation of the pulse width at a rate between about 0.5 Hz and 1 Hz may be desirable to increase patient comfort during stimulation.

In some variations, the increase and decrease of pulse width may be defined by a function implemented by the stimulator. For example, the pulse width may be defined by a function such that the pulse width varies exponentially. In one variation, the function defining pulse width may comprise two phases—a first phase during which the pulse width of the leading pulse increases over time, and a second phase during which the pulse width of the leading pulse decreases over time. During the first phase, the pulse width of the leading pulse approaches the maximum pulse width according to an exponential function, where at time t, PW{t} is defined by the equation $$PW\{t\} = (PW_{max} - PW_{min})(1 - e^{-(\frac{t}{\tau})})$$

where $PW_{max}$ is the maximum allowed pulse width, $PW_{min}$ is the minimum allowed pulse width, and τ is a time constant.

Once a predetermined amount of time has elapsed (a multiple of time constant τ), the pulse width modulation may enter the second phase. During the second phase, the pulse width of the leading pulse exponentially decays from its maximum value to a minimum value following the exponential equation $$PW\{t\} = (PW_{max} - PW_{min})(e^{-(\frac{t}{\tau})}).$$

Figure 8:
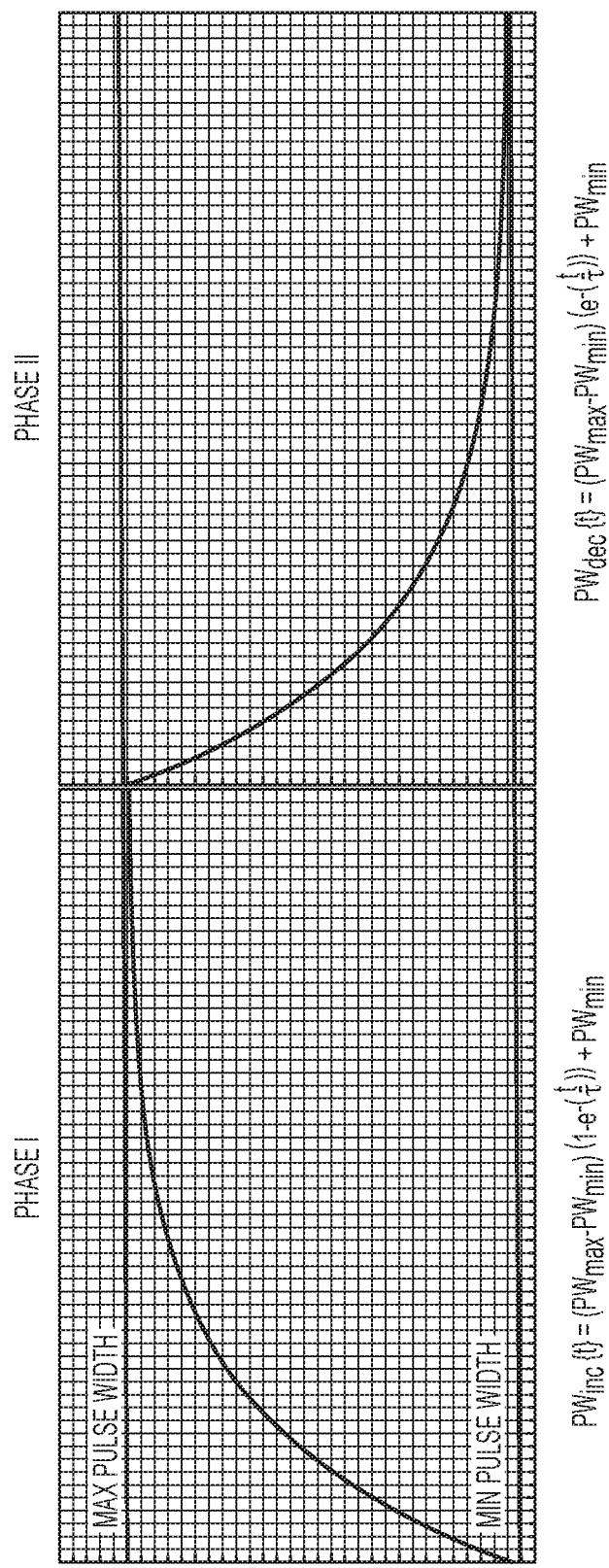
FIG. 8 shows an exemplary function defining pulse widths increasing and decaying according to an exponential function.

After a predetermined amount of time has elapsed (a multiple of time constant τ), the pulse width modulation may re-enter the first phase, and the cycle may repeat. The pulse width of the secondary (charge balancing) pulse is increased and decreased accordingly to retain charge full balancing. PWmax, PWmin, and τ may have any suitable values to achieve the pulse widths described herein, but in one example the waveform may have a PWmax of 300 μs, PWmin of 0 μs, and τ of 1/5 μs. In other variations, for example, PWmax, may be about 100 μs, about 200 μs, about 300 μs, about 400 μs, or about 500 μs; PWmin may be about 0 μs, about 10 μs, about 50 μs, or about 100 μs; and τ may be about 1/3 μs, about 1/4 μs, about 1/5 μs, or about 1/6 μs. An exemplary function defining exponentially increasing and decaying pulse widths is shown in FIG. 8.

On/Off Periods

In some instances, the waveforms described herein may be delivered in a continuous fashion, while in other instances, the waveforms may be delivered in a non-continuous fashion having on periods and off periods, which may reduce patient accommodation. Exemplary on/off durations include without limitation, 1 second on/1 second off, 1 second on/2 seconds off, 2 seconds on/1 seconds off, 5 seconds on/5 seconds off, 0.2 seconds on/0.8 seconds off, less than 1 second on/less than 10 seconds off.

Exemplary Waveforms

It should be appreciated any of the above waveform parameters and variations in parameters may be combined to generate a temporally patterned waveform as described herein, and these waveforms may be delivered by any of the stimulators described herein. For example, in variations where the waveform comprises a biphasic pulse, the biphasic pulse may have any suitable frequencies, pulse widths, and amplitudes. The stimulation amplitude, pulse width, and frequency may be the same from pulse to pulse, or may vary over time, as described in more detail herein. Combinations of these parameters may increase the efficacy and/or comfort of stimulation, and in some cases, the efficacy and/or comfort may differ by individual patient, as described in more detail herein. Exemplary waveform parameters categorized by device type are listed below in Table 1.

TABLE 1

Exemplary Waveform Parameters

| Device Type | Stimulation Target | On/Off | Frequency (Hz) | Pulse Width (PW) | Amplitude (mA) |
|---|---|---|---|---|---|
| Ocular Stimulator (implantable) | Orbital nerves (afferent & efferent) | Constant on | 30 | Fixed from 50 μs to 1200 μs | 0.1 to 10 |
| | | 1 sec on/ 1 sec off | 30 | | |
| | | 5 sec on/ 5 sec off | 30 | | |
| | | 1 sec on/ 1 sec off | 70 | | |
| | | 1 sec on/ 1 sec off | 155 | | |
| | | Constant on | Modulated from 30 to 70 in triangular fashion | | |
| | | Constant on | 30 | Triangular modulated from 50 μs to max PW at 0.5 Hz | |
| | | Constant on | 30 | Triangular modulated from 50 μs to max PW at 1 Hz | |
| | | Constant on | 70 | Triangular modulated from 50 μs to max PW at 0.5 Hz | |
| Nasal Stimulator (handheld or implantable) | Internal and external nasal nerves (e.g., anterior ethmoidal nerve) | Constant on | 30 | 0 μs to 300 μs | 0.1 to 10 |
| | | Constant on | 50 | | |
| | | Constant on | 80 | | |
| | | Constant on | 150 | | |
| | | 1 sec on/ 1 sec off | 30 | | |
| | | 1 sec on/ 1 sec off | 50 | | |
| | | 1 sec on/ 1 sec off | 80 | | |
| | | Constant on | 30 | | |
| | | 1 sec on/ 1 sec off | 70 | | |

In variations in which a waveform is an alternating monophasic pulsed waveform, each pulse delivered by the stimulator may have a single phase, and successive pulses may have alternating polarities. Generally, the alternating monophasic pulses are delivered in pairs at a given frequency (such as one or more of the frequencies listed above, such as between 30 Hz and 80 Hz), and may have an inter-pulse interval between the first and second pulse of the pair (e.g., about 100 μs, between 50 μs and 150 μs or the like). Each pulse may be current-controlled or voltage-controlled, and consecutive pulses need not be both current-controlled or both voltage-controlled. In some variations where the pulse waveform is charged-balanced, the waveform may comprise a passive charge-balancing phase after delivery of a pair of monophasic pulses, which may allow the waveform to compensate for charge differences between the pulses.

When a stimulator configured to deliver an electrical stimulation waveform is positioned to place an electrode on either side of the nasal septum, alternating monophasic pulses may promote bilateral stimulation of nasal tissue. The pulses of a first phase may stimulate a first side of the nose (while providing a charge-balancing phase to a second side of the nose), while the pulses of the opposite phase may stimulate the second side of the nose (while providing a charge-balancing phase to the first side of the nose), since nerves may respond differently to anodic and cathodic pulses. The inter-pulse interval may give time for the stimulation provided by a first phase pulse to activate/polarize the target nerves prior to being reversed by an opposite phase pulse.

Stimuli comprising the waveforms described herein may be delivered to these anatomical targets using stimulators such as those described herein according to treatment regimens described in U.S. patent application Ser. No. 13/441,806, which was previously incorporated by reference in its entirety, and in U.S. patent application Ser. No. 14/256,915, which was previously incorporated by reference in its entirety.

Patient-Optimized Waveforms

Figure 9:
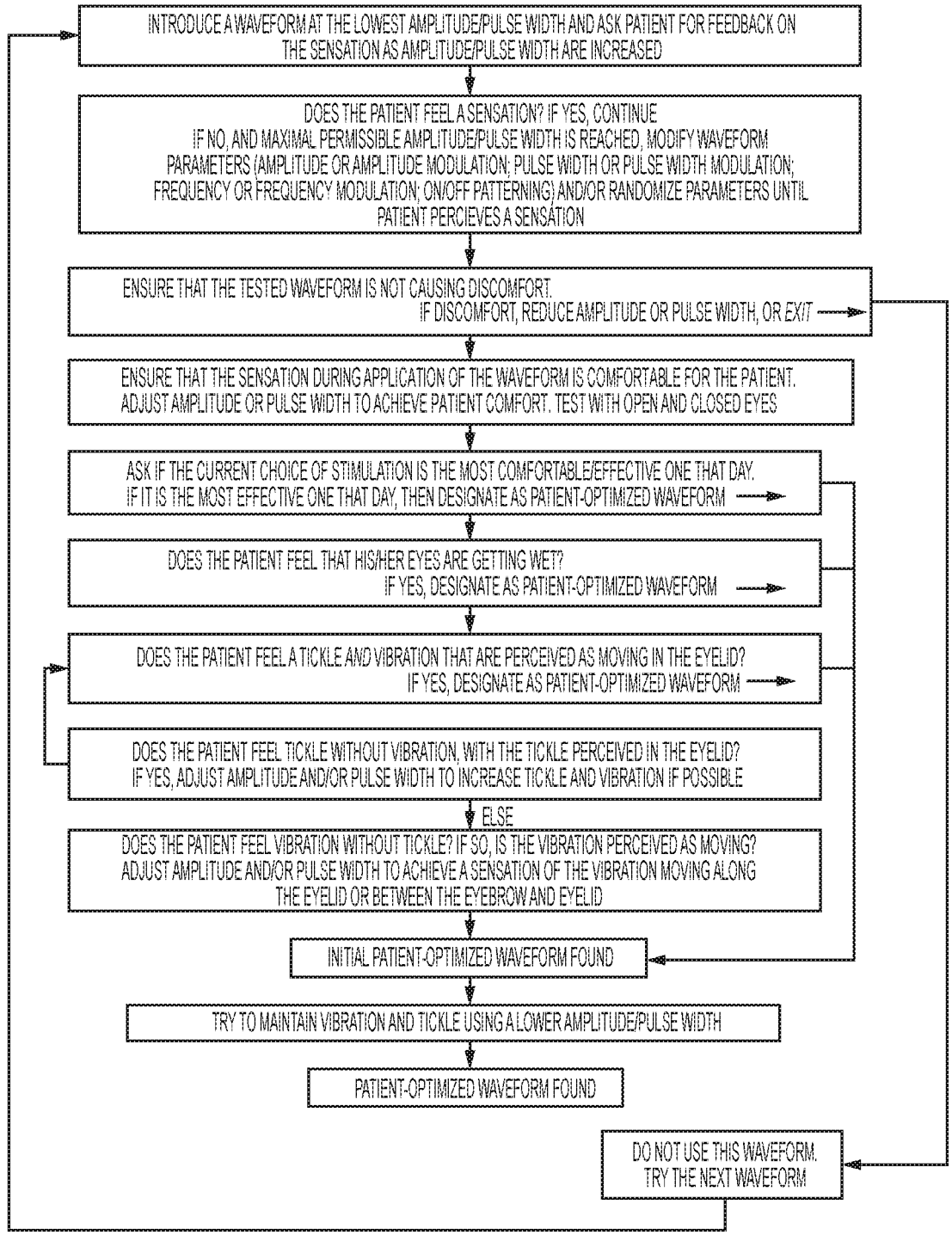
FIG. 9 shows a flowchart illustrating a method used in determining a patient-optimized waveform.

Experimentation by the inventors has found that in some instances, lacrimation caused by stimulation may be increased by identification of one or more patient-optimized waveforms for a particular patient, where the patient-optimized waveforms may comprise combinations of the waveform parameters described herein. As such, a method for identification of patient-optimized waveforms is desirable. Experimentation by the inventors has also found that sensed paresthesia is strongly associated with lacrimation, and thus patient perceptions of paresthesia may be used in identification of patient-optimized waveforms. An exemplary method for obtaining patient-optimized waveforms in a patient having a microstimulator implanted in an ocular region is illustrated in FIG. 9. It may be desirable to perform this method for each individual to increase the effectiveness of stimulation (e.g., to increase tearing). The stimulation waveform(s) and/or current steering may also be configured to optimize certain clinical indicators of effectiveness, including but not limited to growth factor levels and/or osmolarity.

As shown there, a waveform may be assessed to determine if it is a patient-optimized waveform by delivering an electrical stimulus comprising the waveform to the patient using a stimulator described herein. The method may comprise first delivering a waveform at the lowest amplitude and/or pulse width and asking the patient for feedback on the sensation as the amplitude and/or pulse width is increased. The method may then comprise assessing whether the patient feels any sensation during delivery of the electrical stimulus. If not, a different waveform may be selected (e.g., having a different combination of parameters, such as frequency, amplitude, pulse width, on/off period, or the temporal modulation of these parameters). The method may further comprise ensuring that the patient is not experiencing discomfort. If the patient is experiencing discomfort, the method may be restarted with a new waveform, or the amplitude and/or the pulse width may be reduced to alleviate discomfort. Similarly, the method may comprise ensuring that the sensation during application of the waveform is comfortable to the patient. The amplitude and/or pulse width may be adjusted to achieve patient comfort. Comfort may be assessed with the patient's eyes both open and closed.

A waveform may be designated as a patient-optimized waveform if the patient perceives the waveform as the most comfortable and/or effective waveform felt that day; and/or if the patient feels his/her eyes getting wet; and/or if the patient perceives paresthesia—more particularly, if both a tickle and a vibration are perceived as moving in the eyelid. If the patient perceives a tickle in the eyelid but no vibration, the amplitude and/or pulse width may be adjusted to achieve increased perception of tickle and/or vibration. If the patient perceives a vibration but not tickle, the amplitude and/or pulse width may be adjusted to achieve an increased sensation of movement of the vibration (e.g., between the eyelid and eyebrow). It may also be desirable that a patient feels a sensation (e.g., tickle or vibration) after delivery of the stimulus ends. In each case of an identified patient-optimized waveform, a lower amplitude and/or pulse width may be tested to determine whether the same sensation can be achieved using a lower amplitude and/or pulse width. In variations of stimulators configured to allow for spatial control of current pathways, patient-optimization may also comprise testing different current pathways or combinations of current pathways.

While the method in FIG. 9 is described with respect to a patient having an implantable stimulator located in an ocular region, it should be appreciated that a similar method may be used to identify one or more patient-optimized waveforms for an implantable stimulator in another region (e.g., a nasal region) or for a handheld stimulator. Once a patient-optimized waveform or waveforms are identified, a stimulator may be configured to deliver the waveform(s). In some variations, an external device may be used to configure the stimulator to deliver the identified waveform(s). In variations in which the system comprises a controller for use with an implantable stimulator having a passive stimulation circuit, a controller configured to generate an output signal that results in the identified stimulation waveform(s) may be used.

Devices Having a Plurality of Waveforms

Some variations of the stimulators described herein may be configured with a plurality of waveforms, such that a clinician and/or patient may select a desired waveform from the plurality of available waveforms. For example, the stimulator may include a plurality of stimulation waveforms saved on a chip. For example, 2, 3, 4, 5, 6, 7, 8, 9, 10, or more than 10 stimulation waveforms may be saved on a chip. In one variation, two to ten stimulation waveforms are saved on a chip. In other variations, two to eight stimulation waveforms, or three to five stimulation waveforms may be saved on the device chip. In some variations, a preferred set of waveforms to be saved on a stimulator may be preselected by a clinician based on initial testing of a variety of stimulation waveforms for a particular patient, such as via the method described above. It may be useful for the saved stimulation waveforms to be those that elicit strong paresthesia in the patient, because experimentation by the inventors has found that sensed paresthesia is more strongly associated with lacrimation, as described herein. In other variations, a stimulator may be preconfigured with a plurality of stimulation waveforms not unique to an individual patient.

In some variations, for every stimulation provided during the day, a different waveform may be randomly selected from the saved plurality of waveforms. By randomly selecting a different waveform each time, the risk of patient developing tolerance to any particular stimulation pattern may be lowered. In another implementation, a multiplexor might be used to provide different combinations of internally saved waveforms to form a "quasi-non-repetitive" waveform when combining pieces from different repetitive waveforms. By multiplexing different waveforms to one combined waveform, habituation to the waveform can potentially be limited further. For stimulators having a plurality of possible current pathways, the same or different waveforms may be delivered via each pathway.

In some variations, a patient may be able to selectively choose between the plurality of stimulation waveforms saved on the stimulator, for example, using a user interface such as a user interface as described herein. In variations having such a user interface, the user interface may comprise one or more operating mechanisms, which may allow the user (i.e., the patient) to control the stimulation waveform. For example, the user interface may comprise one or more structures, such as but not limited to a button, slider, lever, touch pad, knob, or deformable/squeezable portion of the housing, which may allow the user to change the stimulation waveform.

The different waveforms may be configured such that a patient may perceive them as spanning a range of intensities. In variations in which the stimulator is configured to deliver waveforms with different shapes, a patient may be able to change the tissue that is preferentially stimulated by the waveform as described herein by selecting a waveform having a different shape (e.g., switching from a waveform having a cathodic pulse first to a waveform having an anodic pulse first). In some variations, when a patient turns on the stimulator for a second or subsequent treatment period, the stimulator may initially turn on to a waveform selected previously by the patient (e.g., the waveform used during the previous treatment session, the most commonly used waveform during a plurality of treatment sessions, etc.).

For example, in the instance where a handheld nasal stimulator is employed, after the user has placed a portion of the stimulator in contact with the nasal tissue, the user may increase the perceived intensity of the stimulus by changing between the plurality of stimulation waveforms. It may be desirable for the patient to increase the intensity of the stimulus until the stimulus causes preferred paresthesia (e.g., tingling, tickling, prickling) without causing discomfort. As such, the patient may be able to self-determine the proper stimulation intensity and self-adjust the stimulus to a waveform effective to achieve the desired result (e.g., tear production). It may be desirable for the user to increase the intensity of the stimulus slowly in order to minimize discomfort. Some patients might prefer their sensation level to change over the course of time. They might want to start with a strong sensation, followed by a weak sensation. They might prefer to start with a weak sensation (e.g., light tickle) followed by a stronger temporary sensation (e.g., light discomfort for a very short time). Some patients may be able to reduce a sensation of needing to sneeze during stimulation if strong and weak sensations are varied.

In one particular example, a stimulator described herein may be configured to deliver a plurality of different waveforms each having a combination of one or more of shape modulation, maximum amplitude modulation, pulse width modulation, and frequency modulation, as described herein.

Figure 10:
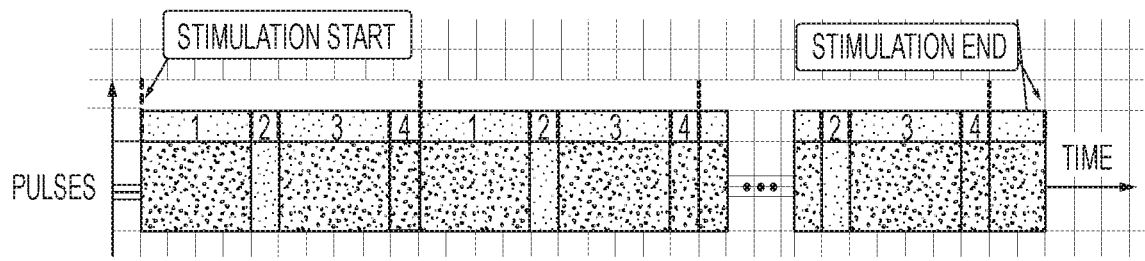
FIG. 10 illustrates exemplary shape modulation.

One or more of the waveforms may have a pulse shape that is modulated over time. In a variation illustrated in FIG. 10, the pulse shape may be cycled between four periods. The first period may comprise a two-phase current-controlled waveform with symmetrical phases. The second period may comprise a current-controlled first phase, followed by a voltage-controlled second phase. This may help to preferentially stimulate a location closer to one electrode. The first phase may have a current sourced by a first electrode and sunk by a second electrode, while the second phase may have a current sourced by the second electrode and sunk by the first electrode. The third period may comprise a two-phase current-controlled waveform with symmetrical phases (i.e., the third period may be the same as the first period). The fourth period may comprise a current-controlled first phase, followed by a voltage-controlled second phase. The first phase may have a current sourced by the second electrode and sunk by the first electrode, while the second phase may have a current sourced by the first electrode and sunk by the second electrode. In each period, the pulses may be charged-balanced. The pulse shape may be modulated at any suitable frequency, such as about 0.1 Hz.

Figure 11:
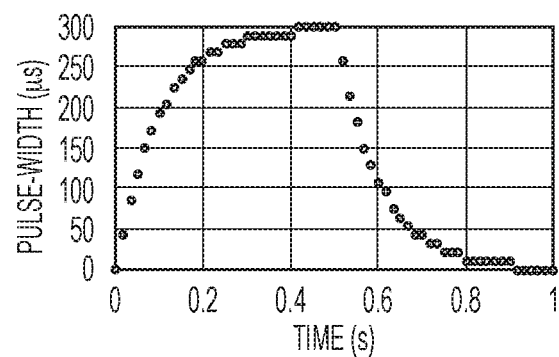
FIG. 11 illustrates exemplary pulse width modulation.

One or more of the waveforms may have a pulse width that is modulated over time. In one variation, the pulse width of the current-controlled phases may be modulated from 0 μs to 300 μs. The modulation may follow an exponential function that describes the increase and decrease of the pulse width over time, as illustrated in FIG. 11 and as described in more detail with respect to FIG. 8.

Figure 12A:
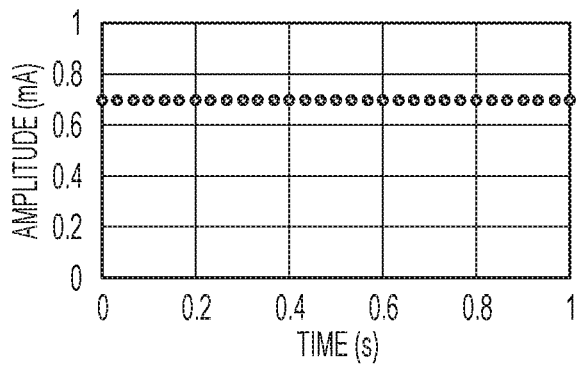
FIGS. 12A-12E illustrate exemplary modulations of amplitude and frequency waveform parameters.

One or more of the waveforms may have a maximum amplitude that is modulated over time. The amplitude modulation of the current-controlled phases may approximate a triangular shape, a rectangular shape, or any other suitable shape. Exemplary amplitude modulations at various frequencies are illustrated in FIGS. 12A-12E, which show amplitude modulations having a rectangular shape (FIG. 12B) and amplitude modulations that approximate triangular shapes (12C-12E). The maximum amplitude may be modulated at any suitable frequency, such as between about 0.5 Hz and about 3 Hz. It should be appreciated that in some other variations, the maximum amplitude may be constant, as shown in FIG. 12A.

FIGS. 13A-13E depict exemplary waveforms 1310, 1320, 1330, 1340, and 1350, respectively, wherein one or more of these parameters are modulated over time, where each type of modulation is independent from and concurrent with the other types of modulation. Boxes 1302, 1304, and 1306 on FIG. 13E highlight modulation of shape, pulse width, and maximum amplitude, respectively. In some variations (e.g., those of FIGS. 13B-13E) all three of shape, pulse width, and maximum amplitude are modulated over time, but it should be appreciated that in other variations of the waveform (e.g., that of FIG. 13A), only one or two of these parameters may be modulated over time.

The five waveforms of FIGS. 13A-13E may be available on the stimulator (e.g., stimulator 400 described above with respect to FIGS. 4A-4C, or microstimulator 200 described above with respect to FIGS. 2A-2C), and the stimulator may be configured such that the patient can use a user interface (e.g., an interface comprising two buttons) to select between the five different waveforms. In some variations of the device, when the device is used for a treatment period, turned off, and turned back on for an additional treatment period, the device may automatically turn on to the last stimulation setting used.

Figure 13A:
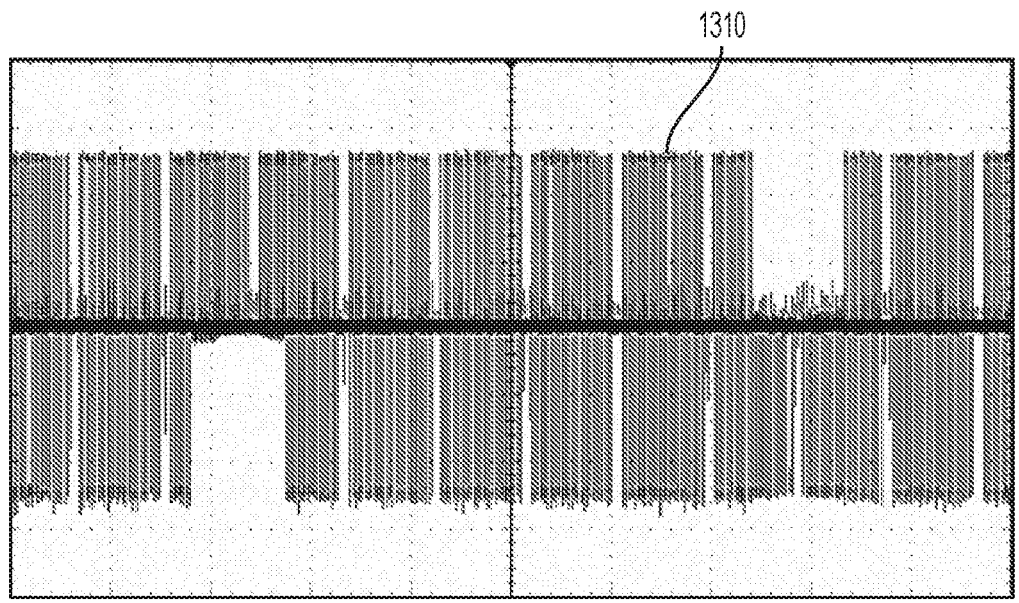
FIGS. 13A-13E depict exemplary waveforms showing multiple parameters that are concurrently modulated over time.

Setting 1, illustrated in FIG. 13A, may have a stimulation frequency of 30 Hz; a minimum stimulation current amplitude of 0.7 mA, a maximum stimulation current amplitude of 0.7 mA, and thus no variation in maximum stimulation current amplitude (as shown in FIG. 12A); a minimum pulse width of 0 μs; a maximum pulse width of 300 μs; a pulse width modulation frequency of 1 Hz (rising and falling according to an exponential function, as shown in FIG. 11); a minimum charge injection per phase (at 0 μs pulse width) of 0 μC; a maximum charge injection per phase (at 0.7 mA and 300 μs) of 0.21 μC; and a pulse shape that is modulated as described above with respect to FIG. 10.

Figure 12B:
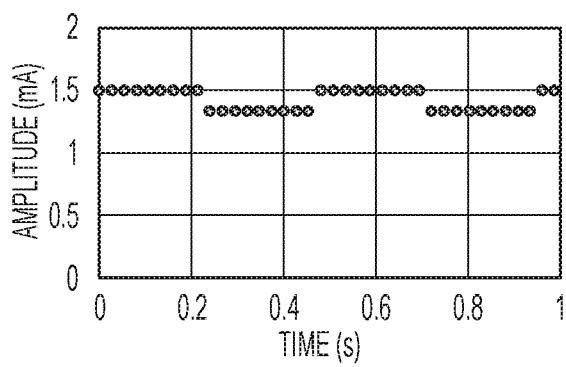
Figure 13B:
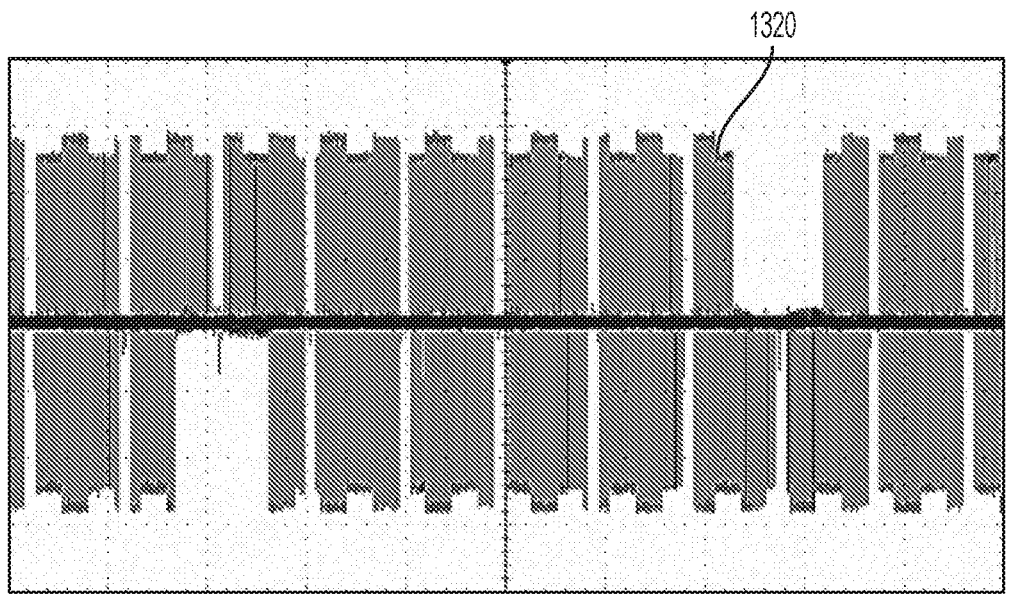

Setting 2, illustrated in FIG. 13B, may have a stimulation frequency of 37.5 Hz; a minimum stimulation current amplitude of 1.33 mA, a maximum stimulation current amplitude of 1.5 mA, a variation in maximum stimulation current amplitude of 0.17 mA, and an amplitude modulation frequency of 2.1 Hz (as shown in FIG. 12B); a minimum pulse width of 0 μs; a maximum pulse width of 300 μs; a pulse width modulation frequency of 1 Hz (rising and falling according to an exponential function, as shown in FIG. 11); a minimum charge injection per phase (at 0 μs pulse width) of 0 μC; a maximum charge injection per phase (at 1.5 mA and 300 μts) of 0.45 μC; and a pulse shape that is modulated as described above with respect to FIG. 10.

Figure 12C:
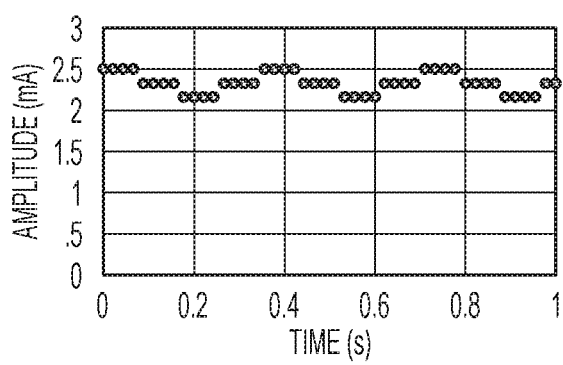
Figure 13C:
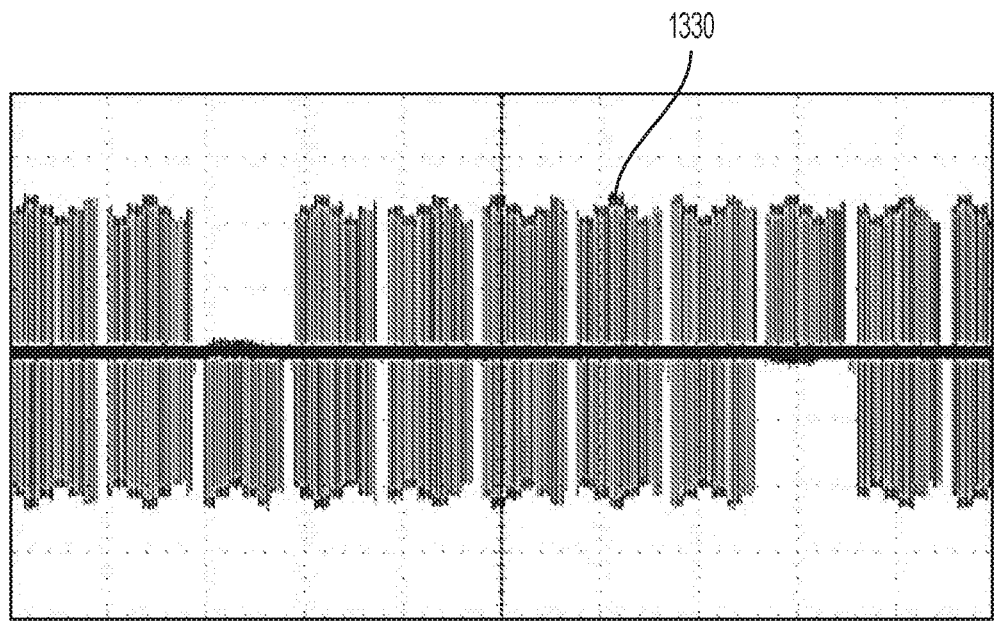

Setting 3, illustrated in FIG. 13C, may have a stimulation frequency of 45 Hz; a minimum stimulation current amplitude of 2.17 mA, a maximum stimulation current amplitude of 2.5 mA, a variation in maximum stimulation current amplitude of 0.33 mA, and an amplitude modulation frequency of 2.6 Hz (as shown in FIG. 12C); a minimum pulse width of 0 μs; a maximum pulse width of 300 μs; a pulse width modulation frequency of 1 Hz (rising and falling according to an exponential function, as shown in FIG. 11); a minimum charge injection per phase (at 0 μs pulse width) of 0 μC; a maximum charge injection per phase (at 2.5 mA and 300 μs) of 0.75 μC; and a pulse shape that is modulated as described above with respect to FIG. 10.

Figure 12D:
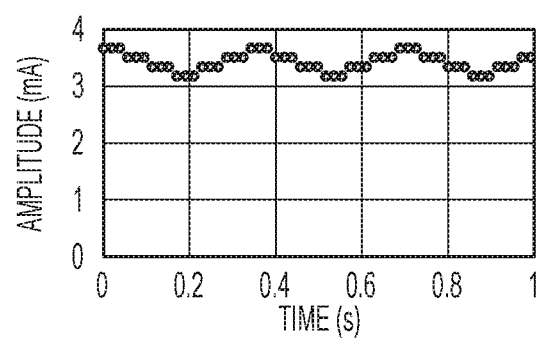
Figure 13D:
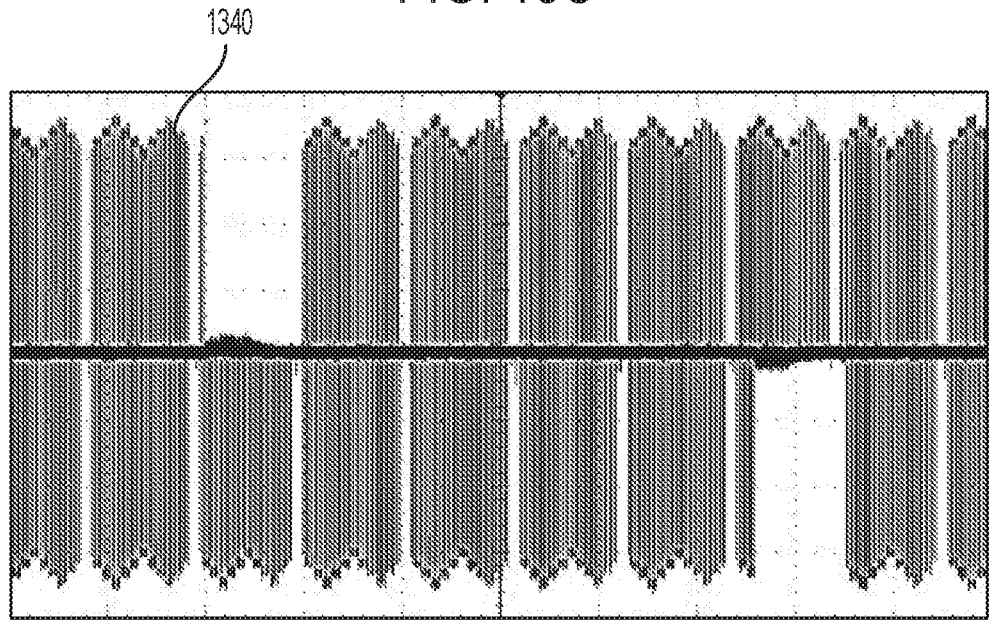

Setting 4, illustrated in FIG. 13D, may have a stimulation frequency of 52.5 Hz; a minimum stimulation current amplitude of 3.2 mA, a maximum stimulation current amplitude of 3.7 mA, a variation in maximum stimulation current amplitude of 0.5 mA, and an amplitude modulation frequency of 2.8 Hz (as shown in FIG. 12D); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 3.7 mA and 300 µs) of 1.11 µC; and a pulse shape that is modulated as described above with respect to FIG. 10.

Figure 12E:
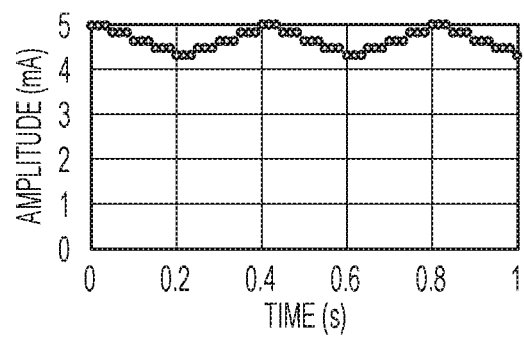
Figure 13E:
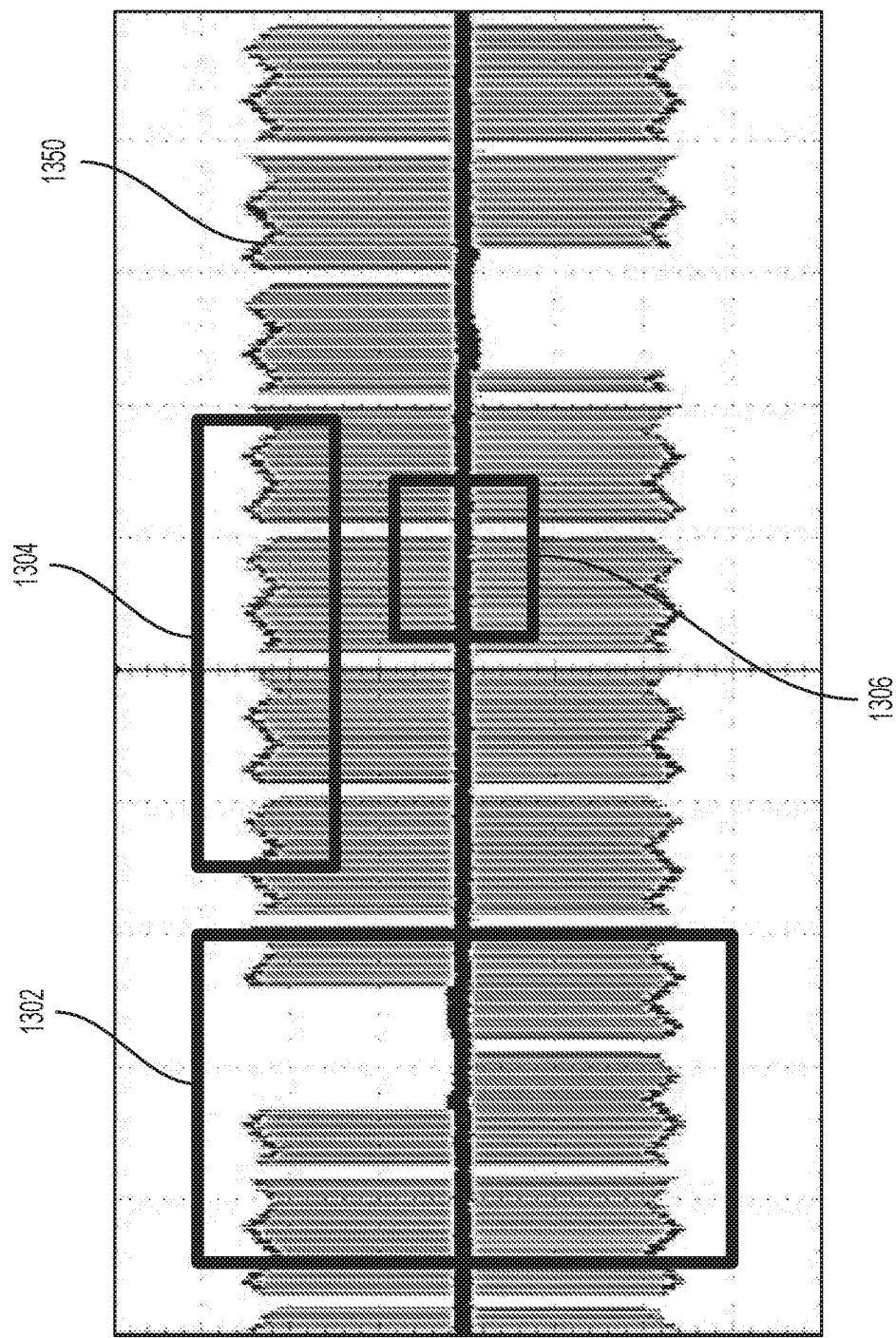

Setting 5, illustrated in FIG. 13E, may have a stimulation frequency of 60 Hz; a minimum stimulation current amplitude of 4.3 mA, a maximum stimulation current amplitude of 5.0 mA, a variation in maximum stimulation current amplitude of 0.67 mA, and an amplitude modulation frequency of 2.5 Hz (as shown in FIG. 12E); a minimum pulse width of 0 µs; a maximum pulse width of 300 µs; a pulse width modulation frequency of 1 Hz (rising and falling according to an exponential function, as shown in FIG. 11); a minimum charge injection per phase (at 0 µs pulse width) of 0 µC; a maximum charge injection per phase (at 5.0 mA and 300 µs) of 1.5 µC; and a pulse shape that is modulated as described above with respect to FIG. 10.

Through waveforms having these parameter combinations, a large parameter space may be provided on a single device with a simple user interface and a limited number of settings. This may increase the ability of a single device having a limited number of preset waveforms to deliver a waveform that is as effective or nearly as effective for an individual patient as a waveform in which parameters are individually tuned for each patient.

EXAMPLES

The following examples further illustrate the electrical stimulation patterns and their effects as disclosed herein, and should not be construed in any way as limiting their scope.

Example 1

Stimulation Using a Lacrimal Implant

Patients having microstimulators implanted in an ocular region were tested with 30 Hz non-patterned stimulation (control) and with on/off patterns (1 second on /1 second off, 2 seconds on/2 seconds off, and 5 seconds on/5 seconds off) at different frequencies (30 Hz, 70 Hz, and 155 Hz). The implanted microstimulators had the features shown in FIGS. 2A-2C and described herein.

Patient perception of the stimulus differed between the 30 Hz non-patterned waveform control and temporally patterned waveforms. Specifically, whereas 3 patients receiving the 30 Hz non-patterned waveform felt that their perception of the waveform faded over the stimulation period, when receiving temporally patterned waveforms, no patients reported perception of the waveform fading over the stimulation period. When the stimulus was a 30 Hz, 1 second on/off waveform ("Pattern 1"), 3 patients perceived the waveform as continuous, while 15 perceived the waveform as intermittent. When the stimulus was a 30 Hz, 5 second on/off waveform ("Pattern 2"), all patients perceived the waveform as intermittent. When the stimulus was a 70 Hz, 1 second on/off waveform ("Pattern 3"), 2 patients perceived the waveform as continuous, and 10 perceived the waveform as intermittent. Patients reported that they perceived Pattern 3 as "stronger," "faster," and "sharper" than the other waveforms. When the stimulus was a 155 Hz, 1 second on/off waveform ("Pattern 4"), whether patients perceived the waveform as continuous or intermittent was amplitude-dependent, and qualitative perceptions ranged, including reports of the waveform as "weaker," "strong," or a "pinch."

Figure 14A:
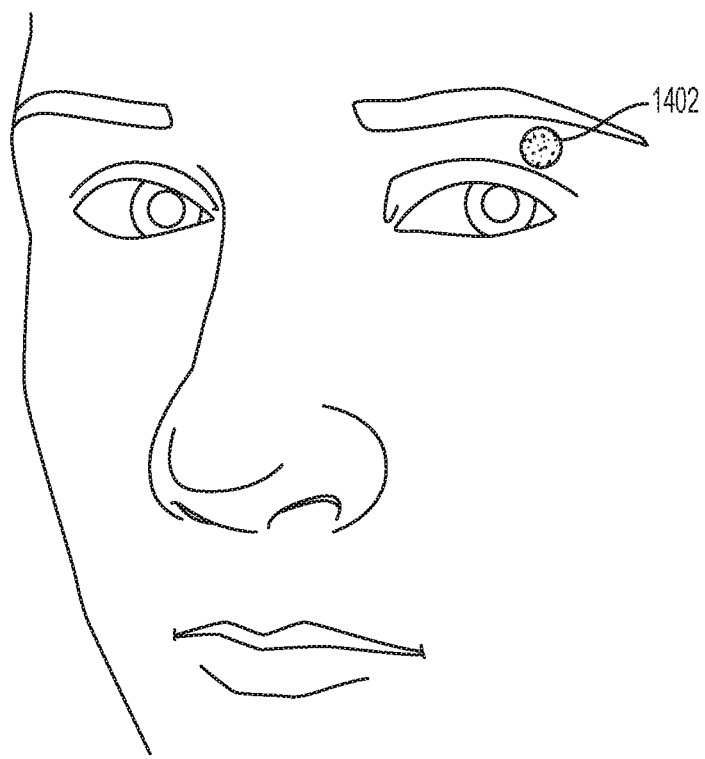
FIG. 14A depicts paresthesia felt with stimulation applied at 30 Hz (non-patterned).
Figure 14B:
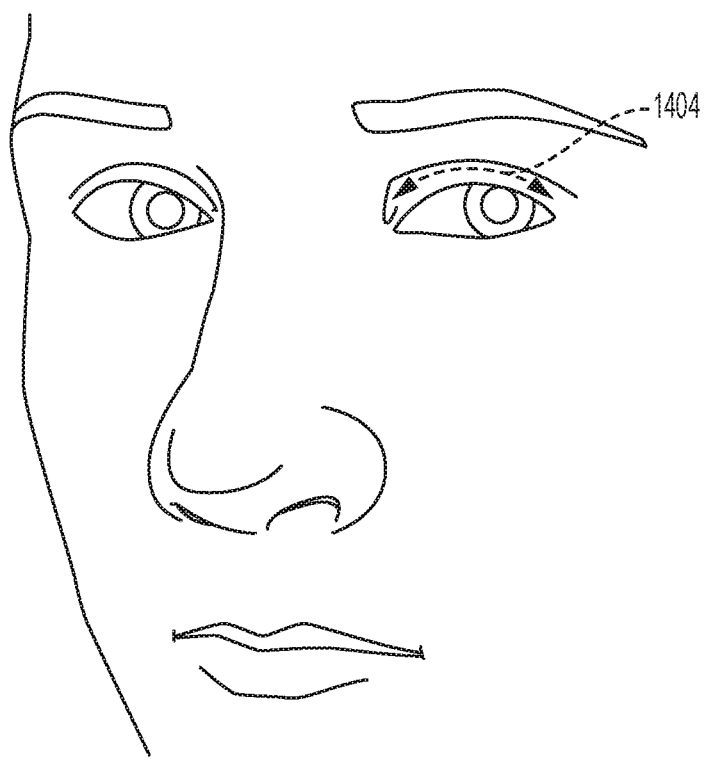
FIG. 14B illustrates an exemplary moving paresthesia obtained with waveform patterning.
Figure 14C:
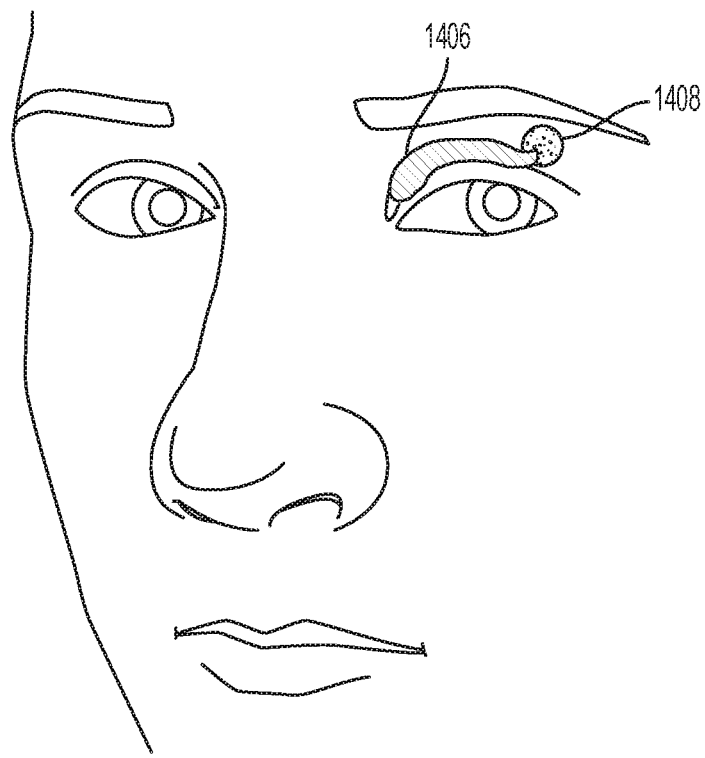
FIG. 14C illustrates another exemplary moving paresthesia obtained with waveform patterning.
Figure 14D:
FIG. 14D depicts paresthesia felt by waveform patterning.

Moreover, patients reported a change in the quality and/or location of paresthesia. FIG. 14A depicts the area 1402 of paresthesia felt with stimulation using the 30 Hz non-patterned waveform. With the temporally patterned waveforms, patients felt movement of the paresthesia (in the form of vibration and/or tickle), as shown in FIG. 14B (the vibration and/or the tingle moved along their eyelid in the directions of the arrows 1404). Some patients felt continuously present vibration in one area 1408 and continuously present or partially appearing and reappearing sensation or tickle in other areas 1406, as shown in FIG. 14C. Other patients experienced an increase in affected area with paresthesia with temporally patterned waveforms, shown in FIG. 14D as area 1410 extending along one or both of the eyebrows and/or along or in the nose.

Patient perceptions after cessation of stimulation also differed between the 30 Hz non-patterned waveform and the temporally patterned waveforms. Whereas patients did not perceive paresthesia after cessation of the control, patients reported perceiving paresthesia in the form of a tingling sensation after cessation of Patterns 1, 3, and 4.

Schirmer scores increased with temporally patterned waveforms as compared to the 30 Hz non-patterned waveform control. With Pattern 1, one third of patients had Schirmer scores that increased by 50%. With Pattern 3, three quarters of patients had Schirmer scores that increased by 50-100%. With Pattern 4, three eighths of patients had Schirmer scores that increased by 100% or more.

Some of the temporally patterned waveforms also provided additional advantages. For example, Pattern 1 used less power than the control while also reducing patient accommodation; and Pattern 4 allowed for both nerve stimulation and block.

Example 2

Stimulation Using a Lacrimal Implant (2)

Figure 15:
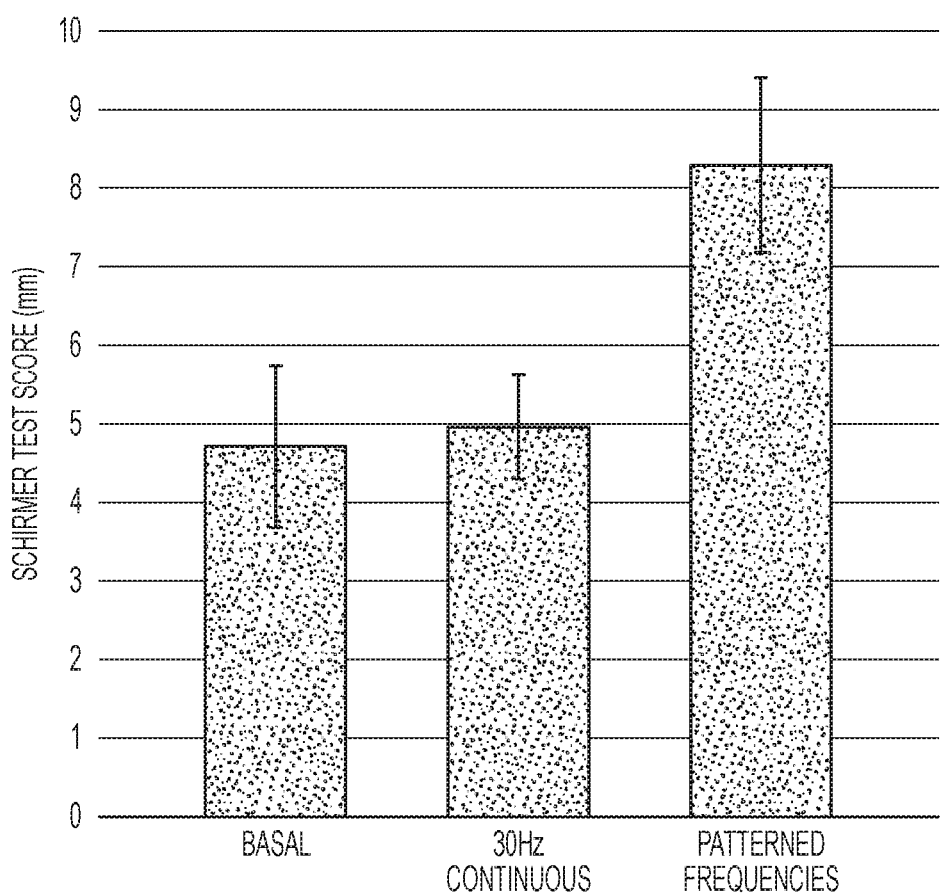
FIG. 15 is a bar-chart diagram comparing tearing results from basal tearing (left, no stimulation) to 30 Hz non-patterned waveform stimulation (middle) to patterned, patient-optimized stimulation waveforms (right).

In patients having a microstimulator implanted in an ocular region, use of temporally patterned waveforms generated an increase in lacrimation as measured by Schirmer's test in comparison to basal tearing (control 1=no electric stimulation) and in comparison to stimulation at 30 Hz (non-patterned) (control 2). The implanted microstimulators had the features shown in FIGS. 2A-2C and described herein. The data is provided below in Table 2, and a bar-chart diagram comparing averaged tearing results from basal tearing (left, no stimulation) to 30 Hz non-patterned waveform stimulation (middle) to temporally patterned, patient-optimized stimulation waveforms (right) is shown in FIG. 15. Based on the data in Table 2, the averaged value for basal tearing was 4.71 mm, the averaged value was 4.96 mm for non-patterned stimulation at 30 Hz, and the average value was 8.29 mm when temporally patterned stimulation was used. Overall, the increase in average Schirmer score using non-patterned stimulation at 30 Hz was about 5% as compared to basal tearing, and the increase in average Schirmer score using temporally patterned waveforms was about 76% as compared to basal tearing. Thus, patient-optimized patterned waveforms were able to increase tearing by a much greater amount (in this case, over 70 percentage points) than a 30 Hz non-patterned waveform.

TABLE 2

Schirmer Scores from 12 Patients.

| Implanted Side | Basal Schirmer Score (mm) | | | 30 Hz Non-Patterned Schirmer Score (mm) | | | Patterned Schirmer Score (mm) | | | Patterned Waveform |
|---|---|---|---|---|---|---|---|---|---|---|
| | L | R | Ave | L | R | Ave | L | R | Ave | |
| R | 8 | 5 | 6.5 | 3 | 4 | 3.5 | 8 | 5 | 6.5 | 30 Hz amplitude modulated by about 30% |
| L | 3 | 8 | 5.5 | 3 | 5 | 4 | 5 | 8 | 6.5 | 70 Hz amplitude modulated by about 30% |
| L | 3 | 2 | 2.5 | 3 | 5 | 4 | 3 | 8 | 5.5 | 70 Hz 1 sec on, 1 sec off |
| L | 2 | 3 | 2.5 | 5 | 5 | 5 | 5 | 3 | 4 | 70 Hz amplitude modulated by about 30% |
| L | 12 | 18 | 15 | 10 | 9 | 9.5 | 13 | 19 | 16 | 30 Hz amplitude modulated by 100% |
| L | 4 | 3 | 3.5 | 6 | 6 | 6 | 7 | 7 | 7 | 70 Hz amplitude modulated by about 30% |
| R | 2 | 3 | 2.5 | 3 | 3 | 3 | 8 | 7 | 7.5 | 30 Hz 1 sec on, 1 sec off |
| L | 5 | 7 | 6 | 5 | 5 | 5 | 8 | 8 | 8 | 70 Hz 1 sec on, 1 sec off |
| L | 2 | 2 | 2 | 2 | 1 | 1.5 | 5 | 5 | 5 | 70 Hz amplitude modulated by about 30% |
| R | 4 | 2 | 3 | 12 | 6 | 9 | 18 | 12 | 15 | 30 Hz 5 sec on, 5 sec off |
| L | 4 | 2 | 3 | 7 | 2 | 4.5 | 7 | 7 | 7 | 30 Hz 1 sec on, 1 sec off |
| L | 4 | 5 | 4.5 | 5 | 4 | 4.5 | 7 | 16 | 11.5 | frequency-modulated 30 Hz to 70 Hz randomized |

The temporally patterned waveforms were also capable of generating paresthesia in patients in whom paresthesia was not felt during stimulation or who only experienced short-lived paresthesia (e.g., less than 30 seconds, often only less than 10 seconds, of paresthesia felt even though stimulation was supplied continuously). The newly acquired or re-acquired paresthesia was further accompanied by increases in lacrimation and improved patient satisfaction.

Patients often reported the feeling of vibration during stimulation and tingle during stimulation pauses (for example, during off portions of waveforms having a 1 second on/1 second off pattern), and in certain cases for seconds or minutes after the stimulation had stopped after application. There were several reports of patients feeling that the vibration or the tingle moved physically along their eyelid and eyebrow, in two cases even in their nasal area (outside and/or inside the nose). Patient reception was generally very positive.

Example 3

Stimulation Using a Lacrimal Implant (3)

Nineteen patients had microstimulators implanted in an ocular region. (Twelve of these patients are the same patients as in Example 2.) For each patient, a patient-optimized temporally patterned waveform was determined by modulating waveform frequency, pulse width, and on/off periods while gathering patient feedback in order to maximize the reported paresthesia in the area of the orbit, as described above.

Each waveform was provided using the same controller/energizer for each patient. The waveforms tested for each patient included:
  30 Hz
  30 Hz, 1 second on, 1 second off
  30 Hz, 5 seconds on, 5 seconds off
  70 Hz, 1 second on, 1 second off
  30 Hz, pulse-width modulated from 100% to 0% and back to 100% in 1 sec
  30 Hz, pulse-width modulated from 100% to 70% and back to 100% in 1 sec
  70 Hz, pulse-width modulated from 100% to 70% and back to 100% in 1 sec
  frequency modulated from 30 Hz to 70 Hz in an approximately linear fashion by steps of 5 Hz (i.e., for the increasing portion of the frequency modulation, 30 Hz, 35 Hz, 40 Hz, 50 Hz, 55 Hz, 60 Hz, 65 Hz, 70 Hz), modulated up and down in 1 sec (from 70 to 30 and back to 70 in one second)
  frequency modulated from 30 Hz to 70 Hz in a random fashion, with frequencies 5 Hz apart (30 Hz, 35 Hz, 40 Hz, 45 Hz, 55 Hz, 60 Hz, 65 Hz, 70 Hz)

Patients were asked a series of questions for each waveform, including:
  whether the waveform was causing discomfort;
  how they would compare the sensation from the waveform to other waveforms, including 30 Hz non-patterned waveform, and any other waveforms previously tested on the same day;
  whether they had the sensation of their eyes getting wet;
  whether they felt a combination of a tickle and vibration;
  whether the sensation (tickle and/or vibration) felt as though it was moving (this suggests less likelihood of accommodation); and
  the location of the sensation.

It was desirable that the patient feel sensation in the upper eyelid, since this was considered likely to correspond with activating the lacrimal and the frontal nerves in the orbit. The closer the sensation was to the eye itself and the larger the area of paresthesia, the more optimal a waveform was rated. Additionally, waveforms that were perceived as a mixture of tickle and vibration sensations in locations that corresponded with the sensory pathways of the ophthalmic branch of the trigeminal nerve (CN V1) were desirable. These locations included not only the eyelid, but also the eyebrow, the temple area of the forehead, the nose (especially the inside of the nose), and certain areas of the forehead.

For each patient, three Schirmer scores were recorded: a basal Schirmer score without any stimulation ("basal Schirmer"), an acute Schirmer score during application of a 30 Hz non-patterned waveform ("30 Hz Schirmer"), and an acute Schirmer score during application of the patient-optimized patterned waveform for each patient ("patterned Schirmer").

Figure 16A:
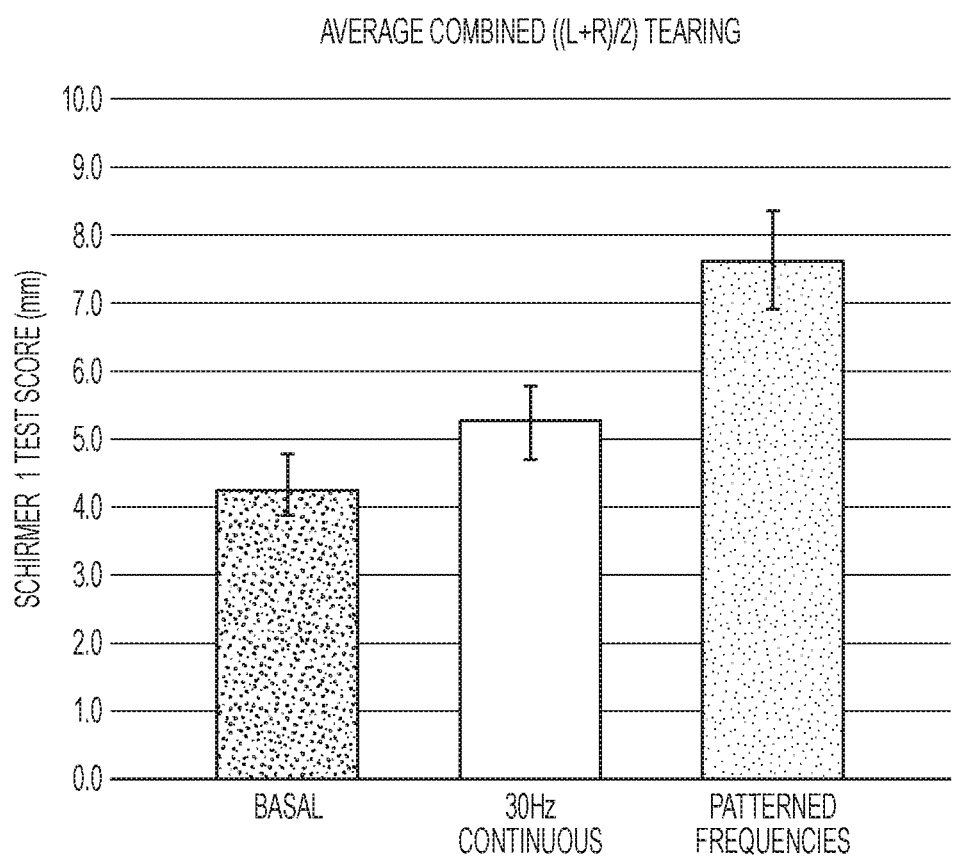
FIG. 16A shows bilateral Schirmer scores with no stimulation, 30 Hz non-patterned stimulation, and patient-specific patterned waveforms.

Average bilateral 30 Hz Schirmer scores and average bilateral patterned Schirmer scores were both higher than average bilateral basal Schirmer scores. Average bilateral patterned Schirmer scores were higher than average bilateral 30 Hz Schirmer scores. Specific data for average bilateral Schirmer scores are shown in FIG. 16A. As shown there, the 15 patients with severe DED (defined as having basal Schirmer scores <10mm) averaged a 22% increase over basal Schirmer scores for 30 Hz Schirmer scores and a 78% increase over basal Schirmer scores for patterned Schirmer scores.

Figure 17A:
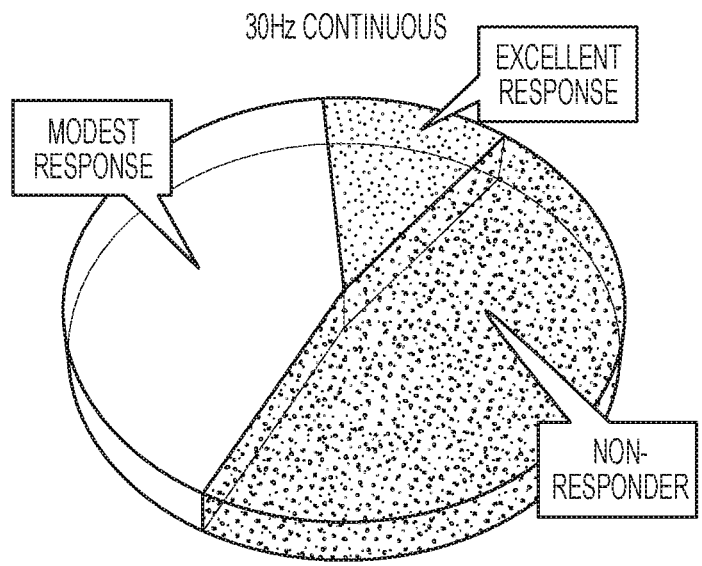
FIGS. 17A-17B show bilateral responses to 30 Hz non-patterned stimulation (17A) and patient-specific patterned waveforms (17B).
Figure 17B:
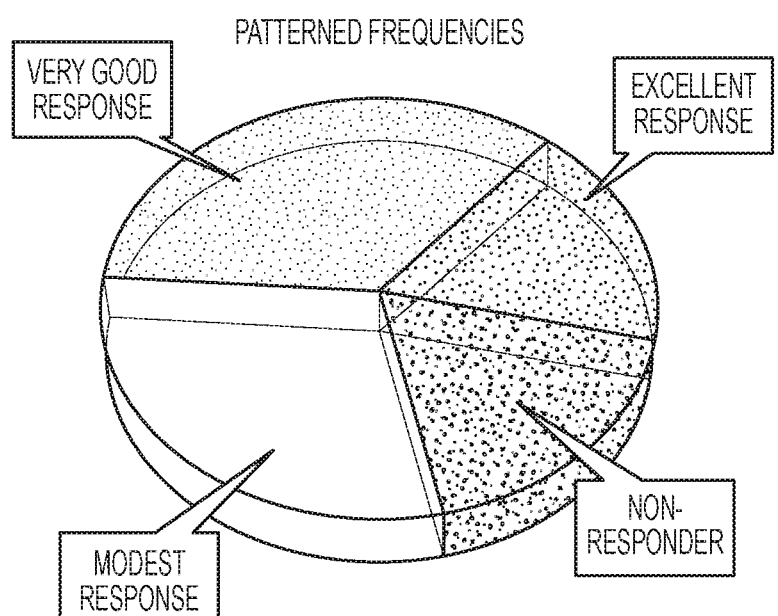

More patients showed increased bilateral Schirmer scores when stimulated using the patient-optimized temporally patterned waveform than the 30 Hz non-patterned waveform. As shown in FIGS. 17A-17B, amongst the 15 patients with severe DED, the number of non-responders decreased from 47% (as shown in FIG. 17A) using the 30 Hz waveform to 20% (as shown in FIG. 17B) using the patient-optimized temporally patterned waveform.

The comparison of ipsilateral (i.e., the eye on the same side as ocular implant), contralateral (i.e., the eye opposite the ocular implant), and bilateral (i.e., the average of both eyes) Schirmer scores indicated that stimulation from a single ocular implant resulted in bilateral tear production, but the effect was more pronounced for patient-optimized temporally patterned waveform stimulation. Ipsilateral 30 Hz Schirmer scores were found to be higher than bilateral 30 Hz Schirmer scores, indicating that 30 Hz stimulation resulted in more tear production in the ipsilateral eye than the contralateral eye; and conversely, contralateral 30 Hz Schirmer scores were found to be lower than bilateral 30 Hz Schirmer scores, indicating that 30 Hz stimulation resulted in less tear production in the contralateral eye than the ipsilateral eye.

Figure 16B:
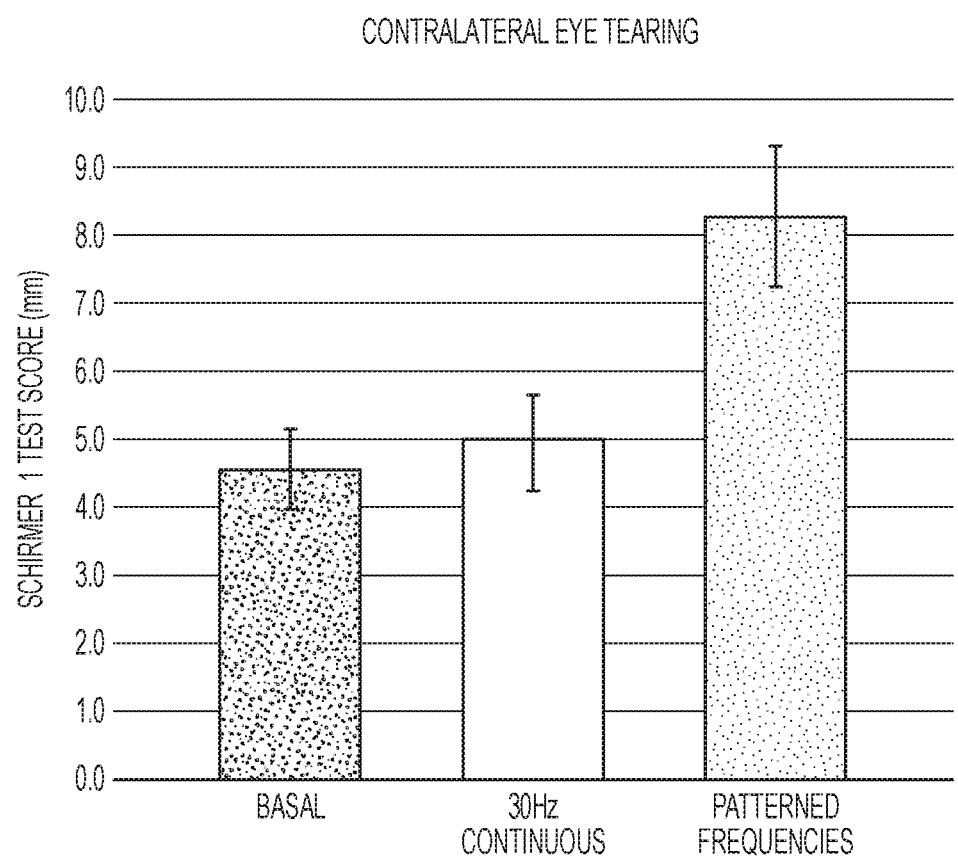
FIG. 16B shows contralateral Schirmer scores with no stimulation, 30 Hz non-patterned stimulation, and patient-specific patterned waveforms.

In contrast, both ipsilateral and contralateral patterned Schirmer scores were found to be similar to bilateral patterned Schirmer scores. This suggested that temporally patterned stimulation better stimulated tear production in the contralateral eye than the 30 Hz stimulation, such that the patient-optimized temporally patterned waveform was equally effective in stimulating tear production in both the ipsilateral and contralateral eyes. It was hypothesized that this was a result of the reflexive drive (activated by stimulating the lacrimal and frontal nerves) adding to the direct drive (lacrimal nerve only). FIG. 16B shows contralateral Schirmer scores for the 15 patients with severe DED. As shown there, the patients averaged a 9% increase over basal Schirmer scores for 30 Hz Schirmer scores and an 82% increase over basal Schirmer scores for patterned Schirmer scores.

By switching frequencies, either linearly or randomly, patients experienced a mixture of vibration and tickle. By changing to the higher frequency of 70 Hz at 1 second on/1 second off, modulating the frequency (30 to 70 Hz in 5 Hz increments), and/or changing the pulse width, specific patients reported the sense of tickle in addition to vibration, tickle alone or the impression of a moving vibration, often in the combination with a moving sensation of tickle. It was also found that stimulation with a patient-optimized temporally patterned waveform allowed patients to find the location for holding the energizers/controllers in order to couple to the implant more quickly and repeatedly.

Example 4

Electrical Stimulation of the Nasal Mucosa

A patterned waveform was delivered to the nasal mucosa of subjects using a device as described with respect to FIGS. 4A-4C. The temporally patterned waveforms delivered included the waveforms shown in FIGS. 13A-13E and described herein, as well as waveforms at 30 Hz, 70 Hz, and 155 Hz with on/off periods of 1 second on/off and 5 seconds on/off. Tear output at the same level as non-patterned stimulation was able to be achieved while reducing subject tendency to sneeze. Subjects also reported the feeling of a nasal massage that was in most cases seen as improved sensory impression. Subjects furthermore were able to use increased stimulation amplitudes during nasal stimulation leading to increased tearing without discomfort, as the maximal amplitude of charge used to stimulate was only applied for a short time. Subject reception was generally very positive.

Example 5

Frontal Nerve Stimulation (Rabbit)

Figure 18:
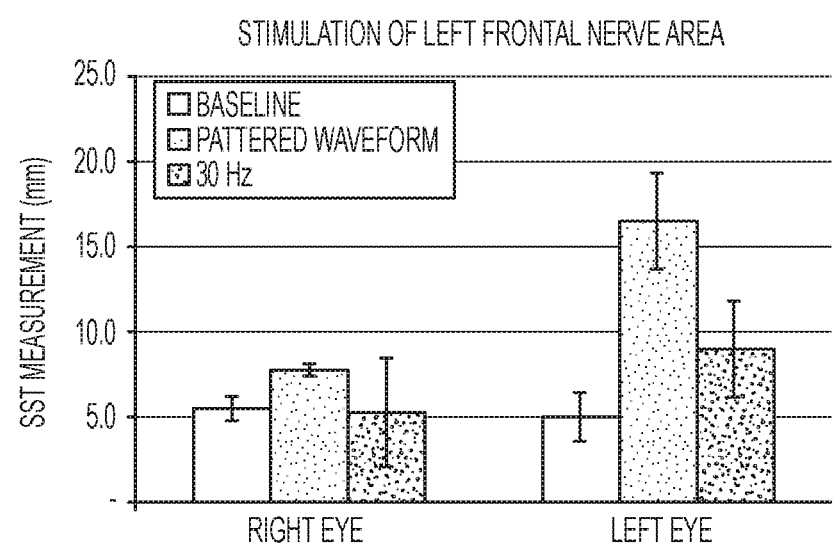
FIG. 18 shows Schirmer scores for stimulation of left frontal nerve areas in rabbits.

A rabbit was implanted with fine wire electrodes into its left frontal nerve area, and stimulation was applied at 30 Hz with amplitudes between 0.1 mA and 5.0 mA. Stimulation and baseline measurements were repeated 3 times each. As shown in Table 3 below and FIG. 18, while increased lacrimation was observed with the 30 Hz (non-patterned) waveform, the increase in lacrimation was more pronounced using a temporally patterned stimulation with on and off periods of 10 seconds each, as measured by Schirmer scores taken during stimulus delivery.

TABLE 3

|  |  | Baseline | | Patterned Waveform | | 30 Hz | |
| --- | --- | --- | --- | --- | --- | --- | --- |
|  |  | AVG | ST DEV | AVG | ST DEV | AVG | ST DEV |
| No Stim | Right Eye | 5.5 | 0.7 | 7.8 | 0.4 | 5.3 | 3.2 |
| Stim Eye | Left Eye | 5.0 | 1.4 | 16.5 | 2.8 | 9.0 | 2.8 |

The invention claimed is:

1. A device for delivering an electrical stimulus to nasal mucosa of a patient, comprising:
 a stimulator probe comprising a nasal insertion prong, wherein the nasal insertion prong comprises a first electrode and a second electrode, wherein the first electrode is configured to deliver current;
 a return contact located at a base of the nasal insertion prong, the return contact configured to receive at least a portion of the delivered current; and
 a user interface configured to allow the patient to adjust an amount of current delivered between the first electrode and the second electrode and between the first electrode and the return contact.

2. The device of claim 1, wherein the first electrode and the second electrode comprise a hydrogel.

3. The device of claim 2, wherein the return contact comprises a hydrogel.

4. The device of claim 1, wherein the return contact has an annular shape and is configured to contact tissue at a nostril.

5. The device of claim 1, wherein the user interface comprises one or more operating mechanisms configured to adjust one or more parameters of the delivered current.

6. The device of claim 1, wherein the current is configured to be delivered between the first electrode and the return contact through tissue of the patient.

7. The device of claim 1, wherein the current is configured to be delivered between the first electrode and the second electrode through tissue of the patient.

8. The device of claim 1, further comprising a stimulator body configured to be held by the patient during delivery of the current.

9. The device of claim 8, wherein the user interface is positioned on the stimulator body.

10. The device of claim 8, wherein the stimulator probe is detachable from the stimulator body.

11. The device of claim 10, wherein the stimulator probe is disposable, and wherein the stimulator body is reusable.

12. The device of claim 1, wherein the return contact is configured to contact tissue of the patient while the patient is holding the stimulator body.

13. The device of claim 1, wherein the first electrode and the second electrode are spaced radially around a circumference of the nasal insertion prong.

14. The device of claim 1, wherein the first electrode and the second electrode are spaced longitudinally along a length of the nasal insertion prong.

15. The handheld device of claim 14, wherein the stimulating portion is releasably coupled to the body portion.

16. The device of claim 1, wherein the nasal insertion prong comprises an elongated extension configured to extend into a nasal cavity.

17. The device of claim 16, wherein the first electrode is positioned along a distal portion of the nasal insertion prong.

18. The device of claim 16, wherein the first electrode is configured to contact the nasal mucosa and stimulate a nerve in the nasal mucosa.

19. A device for delivering an electrical stimulus to facial tissue of a patient, comprising:
 a stimulating portion comprising an electrode, wherein the electrode is configured to deliver current, the simulating portion comprising a return contact positioned on a base member of the stimulating portion and configured to receive the delivered current, the return contact positioned to contact tissue of the patient;
 a body portion configured to be held by the patient while delivering current from the electrode; and
 a user interface configured to allow the patient to adjust an amount of current delivered between the electrode and the return contact.

* * * * *